US011135388B2

(12) United States Patent
Ronayne

(10) Patent No.: US 11,135,388 B2
(45) Date of Patent: Oct. 5, 2021

(54) PATIENT INTERFACE, SYSTEM AND METHOD

(71) Applicant: Fisher & Paykel Healthcare Limited, Auckland (NZ)

(72) Inventor: Michael Paul Ronayne, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 362 days.

(21) Appl. No.: 16/329,162

(22) PCT Filed: Aug. 31, 2017

(86) PCT No.: PCT/IB2017/055229
§ 371 (c)(1),
(2) Date: Feb. 27, 2019

(87) PCT Pub. No.: WO2018/042355
PCT Pub. Date: Mar. 8, 2018

(65) Prior Publication Data
US 2019/0232009 A1 Aug. 1, 2019

Related U.S. Application Data

(60) Provisional application No. 62/381,754, filed on Aug. 31, 2016.

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0051* (2013.01); *A61M 16/0066* (2013.01);
(Continued)

(58) Field of Classification Search
CPC .. A61M 16/00; A61M 16/06; A61M 16/0666; A61M 16/0672; A61M 16/0688;
(Continued)

(56) References Cited

U.S. PATENT DOCUMENTS 4,273,124 A * 6/1981 Zimmerman ..... A61M 16/0666
128/207.18
6,986,353 B2 1/2006 Wright
(Continued)

FOREIGN PATENT DOCUMENTS

WO WO 89/009565 10/1989
WO WO 98/048876 11/1998
(Continued)

OTHER PUBLICATIONS

International Search Report and Written Opinion for PCT/IB2017/055229 dated Oct. 12, 2017 in 9 pages.
(Continued)

*Primary Examiner* — Joseph D. Boecker
(74) *Attorney, Agent, or Firm* — Knobbe, Martens, Olson & Bear, LLP

(57) ABSTRACT

This invention relates to a patient interface, a system and/or method for providing a dedicated or sole inspiratory line or conduit for provision of inspiratory gases to a patient, and a dedicated or sole expiratory line or conduit for provision of expiratory 5 gases to a downstream device, where the inspiratory line or conduit is sealing engageable with the first of a user's nares and the expiratory line or conduit is sealing engageable with the second of the user's nares.

20 Claims, 19 Drawing Sheets

(51) Int. Cl.
  *A61M 16/08* (2006.01)
  *A61M 16/16* (2006.01)
  *A61M 16/20* (2006.01)
  *A61M 16/10* (2006.01)
(52) U.S. Cl.
  CPC ........ *A61M 16/06* (2013.01); *A61M 16/0616* (2014.02); *A61M 16/0672* (2014.02); *A61M 16/0688* (2014.02); *A61M 16/0816* (2013.01); *A61M 16/0891* (2014.02); *A61M 16/161* (2014.02); *A61M 16/201* (2014.02); *A61M 16/0683* (2013.01); *A61M 16/109* (2014.02); *A61M 16/16* (2013.01); *A61M 16/209* (2014.02); *A61M 2016/0027* (2013.01); *A61M 2016/0033* (2013.01); *A61M 2205/15* (2013.01); *A61M 2205/3334* (2013.01); *A61M 2205/3368* (2013.01); *A61M 2205/581* (2013.01); *A61M 2205/584* (2013.01); *A61M 2230/432* (2013.01); *A61M 2240/00* (2013.01)
(58) Field of Classification Search
  CPC .............. A61M 16/08; A61M 16/0816; A61M 16/0833; A61M 16/0841; A61M 16/085; A61M 16/201
  See application file for complete search history.

(56) References Cited

U.S. PATENT DOCUMENTS

| | | | | |
|---|---|---|---|---|
| 2002/0053346 | A1* | 5/2002 | Curti | A61M 16/085 128/207.18 |
| 2004/0139973 | A1* | 7/2004 | Wright | A61M 16/085 128/207.18 |
| 2004/0173210 | A1 | 9/2004 | Campbell | |
| 2005/0005942 | A1* | 1/2005 | Aylsworth | A61B 5/097 128/207.18 |
| 2008/0190436 | A1* | 8/2008 | Jaffe | A61M 16/024 128/207.18 |
| 2010/0113956 | A1* | 5/2010 | Curti | A61M 16/0666 600/538 |
| 2011/0108033 | A1* | 5/2011 | Schaetzl | A61M 16/0666 128/204.21 |
| 2011/0259331 | A1* | 10/2011 | Witt | A61M 16/205 128/204.18 |
| 2012/0222678 | A1* | 9/2012 | Colbaugh | A61M 16/0666 128/205.25 |
| 2014/0276169 | A1* | 9/2014 | Chua | A61B 5/097 600/531 |
| 2016/0213281 | A1* | 7/2016 | Eckerbom | A61B 5/097 |
| 2016/0271353 | A1* | 9/2016 | Cheung | A61M 16/0672 |
| 2017/0049986 | A1* | 2/2017 | Scampoli | A61M 16/085 |
| 2017/0203070 | A1* | 7/2017 | Lei | A61M 16/0616 |
| 2018/0078719 | A1* | 3/2018 | Spence | A61M 16/16 |
| 2021/0016036 | A1* | 1/2021 | Guy | A61M 16/0463 |
| 2021/0046271 | A1* | 2/2021 | Sobel | A61M 16/0666 |

FOREIGN PATENT DOCUMENTS

| | | | |
|---|---|---|---|
| WO | WO 00/72905 | 12/2000 | |
| WO | WO 2007/084940 | 7/2007 | |
| WO | WO 2008/019294 | 2/2008 | |
| WO | WO 2011/061648 | 5/2011 | |
| WO | WO 2014/143847 | 9/2014 | |
| WO | WO 2015/156690 | 10/2015 | |
| WO | WO-2015156690 A1 * | 10/2015 | ........ A61M 16/0677 |

OTHER PUBLICATIONS

International Search Report and Written Opinion for PCT/IB2017/055229 dated Mar. 23, 2020 in 10 pages.

* cited by examiner

PATIENT INTERFACE, SYSTEM AND METHOD

FIELD OF THE INVENTION

The present invention relates to a patient interface, system and method, more particularly, though not solely, to a patient interface, system and method operable to provide for a gases therapy to a user or for when part of a medical breathing circuit or system.

BACKGROUND TO THE INVENTION

Patient interfaces are utilised in medical breathing circuits to provide a either a particular or range of gases therapies to a user (e.g. a patient receiving the gases therapy).

A patient interface, or a patient interface when provided as part of a breathing circuit, that is capable of being providing for specialised gases therapies may provide the user of the interface or circuit, as well as medical professionals, with alternative options for delivering desired gases therapy.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is therefore an object of the present invention to provide a patient interface and/or a patient interface as part of a medical breathing circuit, which will go at least some way towards addressing the foregoing problems or which will at least provide the public with a useful choice.

In a first aspect, this disclosure relates to a patient interface comprising:

a first nasal interfacing component to be provided in fluid communication with a user's first nare, and an associated first conduit provided for an independent and/or dedicated fluid connection with the first nasal interfacing component;

a second nasal interfacing component to be provided in fluid communication with a user's second nare, and an associated second conduit provided for an independent and/or dedicated fluid connection with the second nasal interfacing component;

wherein one of either:

the first nasal interfacing component with said associated first conduit, or the second nasal interfacing component with said associated second conduit is configured as a sole inspiratory line or conduit for delivery of a source of gases to one or a first of the user's nares, and the other of the one of the first nasal interfacing component with said associated first conduit or the second nasal interfacing component with said associated second conduit, may be configured as a sole expiratory line or conduit for receiving gases from the other one or a second of the user's nares.

The first nasal interface component may be configured for interfacing with or partial insertion into the user's first nare.

The second nasal interface component may be configured for interfacing with or partial insertion into the user's second nare.

One or both of said first and/or second nasal interface components may be configured for a non-sealing interfacing with the user's nares.

Alternatively, said first nasal interface component may be configured for either a sealing or a non-sealing interface or engagement with a user's nare.

Alternatively, said second nasal interface component may be configured for either a sealing or a non-sealing interface or engagement with a user's nare.

Alternatively, one of said first and/or second nasal interface components may be configured for either a sealing or a non-sealing interface or engagement with a user's nare, and the other of said first and/or second nasal interface components may be configured for either a sealing or a non-sealing interface or engagement with a user's nare, one or both of said first and/or second nasal interface components may be of a different nare sealing capability or non-sealing capability or are of the same nare sealing capability or non-sealing capability.

The first nasal interface component may be configured for interfacing with or partial insertion with the user's first nare and the second nasal interface component is configured for interfacing with or partial insertion with the user's second nare.

The first nasal interface component may be configured for substantially sealingly engaging or interfacing with the user's first nare.

The second nasal interface component may be configured for substantially sealingly engaging or interfacing with the user's second nare.

The first nasal interface component may be configured for substantially sealingly engaging or interfacing with the user's first nare and the second nasal interface component is configured for substantially sealingly engaging or interfacing with the user's second nare.

The first and second nasal interface components may each comprise of a sealing member for substantially sealing with the nares of a user. Optionally, a sealing member may be provided in the form of nasal pillows associated with one or each of said nasal interface components.

The first and second nasal interface components may each comprise a seal.

Each of the first and second nasal interface components may be shaped or formed to substantially provide for a seal with the nares of a user.

The first and second nasal interface components may be nasal prongs, or may be nasal interface components comprising of a seal, such as nasal pillows.

The patient interface may comprise a partition between the first nasal interfacing component and the second nasal interfacing component.

The partition may provide for a fluid disconnection (this may be mechanical) between a fluid flow path of the first nasal interfacing component and a fluid flow path of the second nasal interfacing component.

The partition may provide for an adjustable or controllable mechanical fluid connection and/or disconnection between a fluid flow path of the first nasal interfacing component and a fluid flow path of the second nasal interfacing component.

The partition may comprise a valve. The valve may be a gate valve or a butterfly valve, or an optionally collapsible section of tubing.

The partition may provide for an adjustment of a bias flow of the source of gases to said first and/or said second nasal interface components.

A diverter valve may fluidly connect the source of gases to one of: the first conduit and the first nasal interface component, or the second conduit and the second nasal interface component to provide the inspiratory line or conduit.

The diverter valve may fluidly connect gases received from one of the first or second nasal interface components via an associated first or second conduit to provide the expiratory line or conduit.

The associated conduit for an inspiratory line or conduit may be connectable to an air source or another gases source, and the associated conduit for an expiratory line or conduit is connectable to a downstream component or device.

A diverter valve may be operable to divert the source of gases to one of the first conduit and the first nasal interface component or the second conduit and the second nasal interface component.

The diverter valve may be operable to divert a received gases from a user via one of the first nasal interface component and the first conduit or the second nasal interface component and the second conduit.

A diverter valve may be provided for alternatively selectively directing the source of gases to either one of the first conduit and the first nasal interface component or the second conduit and the second nasal interface component to operate as an inspiratory line or conduit, and for selectively allowing the other one of the first conduit and the first nasal interface component or the second conduit and the second nasal interface component to operate as an expiratory line or conduit.

The diverter valve may be used to selectively determine:
either the first conduit or the second conduit as the inspiratory line or conduit for delivery of a source of gases to either the first nasal interface component or the second nasal interface component, and
either the first conduit or the second conduit as the expiratory line or conduit for subsequent receipt of gases from either the first nasal interface component or the second nasal interface component.

The diverter valve may be operable to allow the alternation of the delivery of the source of gases to one of either a user's first nare or a user's second nare.

The diverter valve may be operable to allow the delivery of the source of gases in a synchronised manner with a user's nasal cycle (such as a user's natural alternation of increased or reduced congestion between each of the user's nares).

The diverter valve may fluidly connect the expiratory line or conduit with a downstream device (such as a CPAP bubbler or other device creating a back-pressure of the gases in the expiratory line or conduit), or connects to a return port of a gases source.

A detector of a pressure or a flow of gases in the expiratory line or conduit may be used as an indicator of a leak or a loss of gases therapy being provided to the user.

A pressure or flow sensor may be provided in the expiratory line or conduit.

A signal responsive to a pressure or flow of gases in the expiratory line or conduit may be generated by said pressure or flow sensor.

The signal may be indicative of a leak or a loss of gases therapy being provided to the user.

One or both of the first conduit and second conduit may be non-self-supporting or may be collapsible in the absence of a minimum gases pressure within said conduit or when the gases pressure within said conduit is below a predetermined threshold value, such as the conduit of an expiratory line or conduit.

A conduit in fluid communication with the expiratory line or conduit, or the first conduit or the second conduit when provided as, or as part of, the expiratory line or conduit, may comprise an indicator. The indicator may be capable of changing colour to provide a visual indicator of one or more of the following characteristics or qualities of an expiratory gases: carbon dioxide, temperature, humidity, pressure.

An inflatable balloon or diaphragm (or bladder) may be fluidly coupled to the expiratory line or conduit, the relative inflation of the balloon or diaphragm providing an indicator or indication of gases therapy being provided to the user.

A pressure sensor (such as a pressure gauge) may be coupled to the expiratory line or conduit to provide a signal or indicator of the pressure provided to a user or a user's airway or of the gases in the expiratory line or conduit.

The indicator may be a visual indicator of the pressure in the expiratory line or conduit.

The signal may generate one or more of: a visual output, an audible output, an alarm if a sensed pressure is above or below a threshold pressure value.

A first sensor comprising of a pressure sensor may be associated with the inspiratory line or conduit and a second sensor comprising of a pressure sensor is associated with the expiratory line or conduit.

A difference in pressure between gases in the inspiratory line or conduit and gases in the expiratory line or conduit, or a measure of average pressure across the user's nares, may be determined/measured.

A single pressure sensor may be provided for sampling the pressure in an inspiratory line or conduit and an expiratory line or conduit or from a bias flow substantially at a bridge portion of said interface, said sampled pressure providing for an approximation of a patient airway pressure.

The patient interface may comprise a retention system for retaining said interface upon a user's face.

The retention system may be an associated two-part releasable connection arrangement, such that said interface can be positioned upon the user's face and removed and re-positioned as needed.

A first part of the two-part releasable connection arrangement may be a dermal patch to be located upon a user's face, and a second part of the two-part releasable connection arrangement is an interface patch to be located on a user-facing side of the patient interface.

The interface patch may be connected or attached to a user-facing side of the interface, the user-facing side of the interface patch comprising of a part of the two-part releasable connection arrangement being releasably connectable or attachable to an interface-facing side of the dermal patch, the interface-facing side of the dermal patch comprising the other of the two-part releasable connection arrangement and being receivable of the user-facing side of the interface patch.

The two-part releasable connection system provides for attachment mechanism.

The attachment mechanism can be configured for securing a user interface and/or user interface tubing to a patient.

The attachment mechanism may support a nasal cannula on a patient or user face, and/or may be adapted or modified to support a patient interface or parts associated with a patient interface (such as an adaptor which may be utilised on combination with a patient interface) such as by including an extension portion attachable to a patch.

The attachment mechanism may provide for a more rapid and/or improved or simplified ease of installation of a user interface into an operational position on a user. Such benefits may also contribute to improved or simplified ease of application of alternative user interfaces or removal of a user interface from a user when cycling a user between different therapies (such as gas and/or medicament treatments, e.g. CPAP, high-flow, or medicament/aerosolized surfactant delivery applications).

In various embodiments provided by the two-part releasable connection system or an attachment mechanism, such a system or mechanism may provide for quick location of an interface to a user, and may provide for the secured positioning of the interface.

The two-part releasable connection system or attachment mechanism may provide for a first level of securement of a user interface to a user.

Where a user requires additional or heightened security of user interface positioning or securement, a secondary level of interface securement can be utilized.

Optionally, such an additional level may include application of an over patch. Optionally, such an over patch may be an adhesive patch and may be installed over the top of the user interface and/or tubing or conduit or lines associated with the patient or user interface and can be adhered to a portion of the dermal patch.

The two-part releasable connection system or attachment mechanism may comprise a two-part releasable attachment or connection arrangement.

The releasable connection arrangement can act between a pair of patches that are affixed to the patient or user and the user interface respectively.

A first patch can be a dermal patch that is adhered or otherwise attached to the patient's skin.

The dermal patch comprises a user side that faces the user's skin and an interface side that faces the user interface.

The user side of the dermal patch may be attached to the skin of a user by a dermatologically sensitive adhesive, for example such as a hydrocolloid.

The user interface side of the dermal patch can be provided with the first part of the two-part releasable attachment or connection system.

A second patch may be a user interface patch.

The user interface patch may comprise a patient or user side and an interface or user interface side.

The patient or user side of the user interface patch may be disposed adjacent the dermal patch when the attachment mechanism or two part releasable connection system is engaged.

The or a complimentary second part of the two-part releasable attachment or connection system may be affixed to the patient or user side of the user interface patch, such that respective parts of the two-part releasable attachment or connection system are engageable when the patches are brought together.

The interface or user interface side of the user interface patch can be affixed to the user interface.

The user interface patch may be integrated with or suitably adhered to the user interface.

A part or corner of the user interface patch may include a region that does not attach to the dermal patch. Optionally, such a region (or tab) may be provided as a grip by a user or carer for removing or detaching the interface from the dermal patch.

The two-part releasable attachment or connection arrangement or system may comprise one or more of: a hook and loop material (such as Velcro™) a magnet or an array of magnets disposed on the respective patches with the poles suitably arranged, an adhesive arrangement that is activated when the patches are urged together (such as a pressure sensitive adhesive) or another suitable releasable suitable coupling.

The interface side of the dermal patch may comprise one of a hook or a loop material, and the patient or use side of the user interface patch may comprise the other of the hook or loop material, such that the dermal and user interface patches are releasably attachable or connectable to each other.

When a hook and loop material is referenced, a hook and loop material can mean any one of a wide variety of area type mechanical fasteners. For example, the Velcro™ product range can include hook and loop product where the hook component includes upstanding nylon hooks (formed as cut loops through a woven backing web) which engage with any complimentary loop pile material. The Velcro™ range can also include extruded hook products, typically of a smaller size and which mate with "fluffy" non-woven fibre backing materials. These hook materials are designed to work with a range of loop substrates and in some cases, these hook materials act as loop substrates as well. Other similar systems include the Dual-Lock™ reclosable fastener system from 3M of St Paul, Minn. USA. The common feature of these releasable fastening systems is that they engage at any part of the contact between the two parts of the system. Precise alignment of individual connectors is not required because a multitude of connectors are distributed across the area of the product. A wide range of releasable fastener systems within this field may be used in the releasable attachment mechanism for providing releasable attachment between the dermal patch and the user interface.

The first part of the two-part releasable attachment or connection system may be adhered to the user interface side of the dermal patch with a suitable adhesive and may occupy up to 100% or less than about 90%, or about 85%, or about 75%, or about 60% or about 50% or about 40% or about 30% or about 20% or about 10% of the interface side surface area of the dermal patch.

In some embodiments, the dermal patch may be a generally planar pad having a thickness less than both its width and its length.

In some embodiments, the pad has an overall oval shape, but may take other shapes.

The pad may comprise a first part of the two-part releasable attachment mechanism or connection system.

In some embodiments, the construction of the dermal patch may be such that the first part of the releasable attachment mechanism or connection system may comprise a substrate and a multitude of fastener elements (e.g. with effective hooks, effective loops or other elements) provided substantially across the area of the substrate.

The substrate may be secured to the body of the dermal patch.

In some embodiments, the substrate may be secured by an adhesive or by a direct bonding during forming of the dermal patch.

In some embodiments, the substrate may be smaller in area than the dermal patch and may be located on the dermal patch so that the substrate does not reach any edge of the dermal patch. In this way, for example, the edge of the substrate can be spread from the edge of the dermal patch all around the perimeter of the substrate.

In some embodiments, the substrate for the first part of the two-part releasable attachment mechanism or connection system can be flexible such that the plane of the substrate may bend to follow a surface that is curved in one direction.

The pad of the dermal patch may be stretchable and conformable to surfaces curved in more than one direction, such as may be required to conform to the contours of the location of placement on the patient or for example a user's face.

According to various embodiments described herein, a first part of the two-part releasable mechanism or connection system may be in or of a form wherein the portion of substrate may be divided by at least one slit or at least one slot into regions, such that that different parts of the substrate portion may bend substantially independently and thus the overall form of the substrate portion may deform to substantially match a surface curved in two directions.

In another embodiment, the attachment mechanism or two-part releasable connection system may comprise a dermal patch and a securing patch.

The securing patch may extend substantially over the user interface and/or tubing or conduit or lines and may adhere to the dermal patch to substantially secure the interface and/or tubing or conduit or lines to the patient or user.

The dermal patch may define a securement footprint that is attached to the patient or user.

The user side of the dermal patch may be configured to attach or adhere to the patient or user's skin.

The securing patch may extend substantially over the user interface and/or associated user interface tubing or conduit or lines and affixes to the dermal patch to secure the user interface to the patient or user.

The securing patch and the dermal patch may be configured such that the securing patch may be contained within or substantially bounded by the securement footprint of the dermal patch when the securement system is applied to a patient or user with a suitable or compatible user interface.

The dermal patch may comprise the same or a greater surface area than the securing patch.

The dermal patch may comprise one part of a two-part mechanical fastener system across its surface or parts of its surface, with the securing patch comprising the other part of the fastening system.

The dermal patch may be sized to reduce the likelihood of the taping or any additional taping to extend onto the skin of the user.

It should be appreciated there are a number of disadvantages and problems associated with the re-positioning of an interface, particularly an infant interface. Included is "snub nosing", epidermal abrasion, or dermal allergies from traditional taping techniques for application of user interfaces (e.g. nasal cannula) to users. Such problems are also incurred during the cycling of a user between different treatment options and, traditionally, the subsequent removal of headgear or tapes or user interfaces and then the installation of new equipment and user interfaces or interface positioning headgear or other gear. Therefore, provision of a securement system which, when applied to a user, is in a ready-to-receive mode for receiving a user interface is a useful step in progressing toward reducing the problems users have previously been faced with. Further, improving the ease of installation, both in terms of complexity as well as time and effort by a carer (e.g. nurse), is of further benefit.

A securement patch may be shaped or otherwise configured to accommodate geometric or other features of the patient or user interface and/or associated user interface tubing or conduit or lines.

The securement patch may comprise a plurality of wings that accommodate the user interface tubing or conduit or lines and can increase the contact surface of the securing patch exposed to the dermal patch.

The securing patch may comprise a pair of wings arranged at one end of the patch.

The wings may be configured to secure to the dermal patch on either side of a patient or user interface and/or associated user interface tubing or conduit or lines. Optionally, this may assist in reducing the potential for the securing patch to bunch about the interface and/or tubing or conduit or lines.

The securement patch may comprise a tube end wing. Optionally, the tube end wing may be configured to extend substantially under the patient or user interface tubing or conduit or lines and substantially affix to the dermal patch, thereby to link the ends of the securing patch.

The attachment mechanism as defined above may be used to secure tubing or conduit or lines to any part of a patient's body, including but not limited to a patient's face, in particular, adjacent the user's upper lip and/or cheek. Neonatal applications may be of particular relevance.

The user side of the dermal patches may comprise of a dermatologically sensitive adhesive (such as a hydrocolloid) that adheres the patch to a user's skin.

The dermal patch may have sufficient surface area to distribute the adhesive and interface retention forces over an adequate area of the user's skin, such as a user's face, to reduce localized pressure build up.

In some embodiments, there is provided a securement system for retaining, holding, or securing pressure and/or a medicament lumen, such as a surfactant lumen or nasogastric lumen, in position on a patient's face or body.

In some embodiments, a pressure lumen may be configured to be fluidly connected to a pressure tube or pressure port of a patient interface, and a medicament delivery port, such as a surfactant delivery port, may be configured to be fluidly connected to the medicament delivery tube, such as a surfactant delivery tube or nasogastric tube.

In some embodiments, the securement system comprises a two-part releasable attachment or connection arrangement.

The releasable connection arrangement can act between a pair of components that are affixed to the user or patient and the pressure and/or medicament tube respectively.

The two-part releasable attachment mechanism may optionally further comprise structures to retain the pressure and/or medicament tube. In some embodiments, these structures may be a holder, clips, flaps, etc.

The two-part releasable attachment mechanism may comprise a panel configured to be folded onto a dermal patch so as to retain a tube.

The dermal patch and the panel may be coupled together at an edge region.

To couple the first and second parts of the two-part releasable attachment system together, the panel may be folded onto the dermal patch to bring the patient or user side of the panel adjacent to the user or patient interface side of the dermal patch to couple first and second parts of a two-part connection system together, optionally to capture or sandwich a tube or conduit or line there between.

The two-part releasable attachment mechanism may further comprise a clip for securing a pressure and/or medicament delivery tube, such as a surfactant tube.

The dermal patch for adhering to the skin of the user or patient may comprise a securement clip that is attached to or integrally formed with the dermal patch.

The securement clip may comprise a recess or cavity or channel for receiving the tube. Optionally, the recess may open so that a section of a tube or conduit or line may be pushed in a lateral direction with respect to a longitudinal axis of the tube into the clip.

The recess may comprises of a lateral dimension similar to or less than a diameter of a tube or conduit or line so that said tube or conduit or line may be gripped firmly by the clip.

In one embodiment, the clip may be releasable from the dermal patch. For example, a two-part connection system or attachment mechanism as described previously may be applied between the clip and the dermal patch. Alternatively, the clip may be releasably attached to a patient or user interface.

In various embodiments, the two-part releasable attachment mechanism or connection system may comprise a wing portion configured to wrap about and secure a pressure and/or a medicament delivery tube or conduit or line, such as a surfactant delivery tube.

Such a securement system may comprise a dermal patch for attaching to the face of a patient or user. Optionally, the dermal patch may comprise a wing portion for wrapping about a tube or conduit or line once said tube or conduit or line has been correctly positioned in a user or patient's nostril.

The retention system may be a headgear. The headgear may be size adjustable for a user's head.

One or more medicaments may be deliverable to the inspiratory line or conduit or to a nasal interfacing component when provided as part of an inspiratory line or conduit. The one or more medicaments may be atomized or nebulized or aerosolized for delivery into a flow of gases in the inspiratory line or conduit or into a gases flow path of a nasal interfacing component when operable as part of an inspiratory line or conduit.

One or more medicaments may be provided into a flow of gases being supplied as an inspiratory flow to a user or patient.

A medicament delivery port may be provided in fluid connection or communication with one or both of the nasal interfacing elements.

A medicament delivery port may be provided in fluid connection or communication with a single or one of said nasal interfacing elements, and a said diverter valve operated or correctly matched so as to provide a said source or supply of gases to the nasal interfacing element associated with the medicament delivery port, to thereby ensure one or more medicaments is delivered or administered into a said flow of gases being delivered as an inspiratory flow to the user or patient.

Alternatively, a medicament delivery port may be provided in fluid connection or communication with two (or both) nasal interfacing elements, and a medicament diverter valve is operated or correctly matched so as to divert the one or more medicaments to be delivered or administered to a user or patient to a nasal interfacing element or the associated line or conduit being supplied with a source of supply of gases to the nasal interfacing element, thereby to ensure the medicament is delivered into the flow of gases being delivered as an inspiratory flow to the user or patient.

The one or more medicaments may be provided into a flow of gases being supplied to a nasal interfacing element selected as an inspiratory nasal interfacing element. Optionally, a nasal interfacing element selection may be achieved by the use of a diverter valve upstream of the nasal interfacing elements.

The one or more medicaments may be provided into a flow of gases being supplied to a nasal interfacing element selected as an inspiratory nasal interfacing element. Optionally, a nasal interfacing element selection may be achieved by the use of a medicament diverter valve to selectively divert a delivery or administration of one or more medicaments via a port to a selected inspiratory nasal interfacing element.

Wherein a particular one of a pair of nasal interfacing elements of a patient interface may be selected as an inspiratory nasal interfacing element by a diverter valve, the diverter valve may be suitably associated with or coupled to a mechanism, such as a medicament diverter valve, associated with a medicament port to selectively divert or direct medicament administered via a port to the selected inspiratory nasal interfacing element.

Alternatively, a valve or a diverter valve or a selector may be operably adjustable at a port or elsewhere on the patient interface for selecting one of the nasal interfacing elements, or an associated conduit with one of the nasal interfacing elements, to be fluidly connected with the port to receive a medicament administered via the port. Optionally, a valve or diverter valve or selector allows for a matching or fluid coupling of a line or conduit connected to the port with a nasal interfacing element selected as the inspiratory line or conduit, for delivery of a medicament via the port to the user or patient.

The patient interface may be provided as part of a closed breathing circuit.

The patient interface may be configurable to provide a continuous positive airway pressure (CPAP) gases therapy to said user. Optionally, gases therapy to the user may include, but are not limited to, the following: non-invasive positive pressure ventilation (NIPPV), Bi-level (BiPAP) or other ventilation strategies may be employed.

It should be appreciated the following additional types of gases therapies may be used or incorporated for provision of a therapy to the user, including but not limited to:

Pressure controlled ventilators, such as those manufactured by Drager/Maquet/Hamilton.

Flow Driven (SiPAP) Ventilators with pressure feedback, such as that using a flow driver.

Various (humidified) gases source with appropriate pressure control on an expiratory line or conduit or associated conduit or limb of such a part of a medical breathing circuit or system (e.g. bubble, PEEP valve), including gases blenders, Oxygen/medical gases bottle, high flow devices (including for example the system manufactured by Fisher & Paykel Healthcare Limited known as Airvo™, or CPAP blowers (including for example the system manufactured by Fisher & Paykel Healthcare Limited known as Icon™)

Humidifiers or other suitable gases conditioning may be provided for the gases being delivered to the user.

The patient interface and system within which said interface may be associated or provided in fluid connection therewith may be supplied or provided with a source of humidification for said gases being delivered to the user. Advantageously, the supply or provision of a source of humidification is important to assist with reduction of drying or desiccation of the airway, for example in situations with a constant uni-directional flow across the nasal mucosa.

The sole expiratory line or conduit may be fluidly coupled to a downstream device configured to provide for a predetermined or an adjustable back-pressure or a PEEP substantially at the opening of said nasal interfacing component provided as the sole expiratory line or conduit for said user.

Each nasal interfacing component may comprise of a fluid pathway, the fluid pathway to be connected at one end by a said conduit providing for the independent/dedicated fluid connection and at the other end by an opening for fluid connection with a user's nare with which a said nasal interfacing component is to be sealingly interfaced.

The source of gases may be a pressurized source or the source is pressurized by an upstream device configured for providing an adjustable or controllable pressure of gases to the opening of a said nasal interfacing component configured as a sole inspiratory line or conduit.

In a second aspect, this disclosure relates to a patient interface comprising:

a pair of nasal interfacing components, one of the pair configured for sole inspiratory gases delivery to one of a user's nares and the other of the pair configured for sole expiratory gases received from the other of the user's nares;

a valve operable to selectively control which one of the pair of nasal interfacing components is to provide the inspiratory gases to the user and which one of the pair of nasal interfacing components is to receive expiratory gases from the user.

In a first mode, the valve may be operable to allow inspiratory gases to be delivered to a first of a pair of nasal interfacing components and allows a second of the pair of nasal interfacing components to receive expiratory gases from the user;

and in a second mode, the valve may be operable to allow inspiratory gases to be delivered to a second of a pair of nasal interfacing components and allows a first of the pair of nasal interfacing components to receive expiratory gases from the user.

In a third aspect, this disclosure relates to a patient interface comprising:

a pair of nasal interfacing components, one of the pair configured for sole inspiratory gases delivery to one of a user's nares and the other of the pair configured for sole expiratory gases received from the other of the user's nares;

a valve, such as a diverter valve as described above, operable to selectively control which one of the pair of nasal interfacing components is to provide the inspiratory gases to the user and which one of the pair of nasal interfacing components is to receive expiratory gases from the user;

wherein in a first mode, the valve allows inspiratory gases to be delivered to a first of the pair of nasal interfacing components and allows a second of the pair of nasal interfacing components to receive expiratory gases from the user;

and in a second mode, the valve allows inspiratory gases to be delivered to a second of the pair of nasal interfacing components and allows a first of the pair of nasal interfacing components to receive expiratory gases from the user.

In a fourth aspect, this disclosure relates to a patient interface comprising:

a pair of nasal interfacing components, to be provided in fluid communication with the nares of a user;

a bridge portion mechanically joining the nasal interfacing components;

wherein the bridge portion comprises a bridge valve, such as the valve described above in relation to allowing for a bias flow, configured to fluidly connect each of the pair of nasal interfacing components.

Each nasal interfacing component may comprise of a gases pathway, at one end of the gases pathway is an opening for fluid communication with the nare of a user, and at the other end of the gases pathway is an associated conduit for extending the gases pathway.

The bridge valve may be operable to adjust or control a bias flow of gases being delivered to a user.

A valve may be operable to selectively control which one of the pair of nasal interfacing components is to provide the inspiratory gases to the user and which one of the pair of nasal interfacing components is to receive expiratory gases from the user;

wherein in a first mode, the valve allows inspiratory gases to be delivered to a first of pair of the nasal interfacing components and allows a second of the pair of nasal interfacing components to receive expiratory gases from the user;

and in a second mode, the valve allows inspiratory gases to be delivered to a second of pair of the nasal interfacing components and allows a first of the pair of nasal interfacing components to receive expiratory gases from the user.

One of the pair of nasal interfacing components may be configured for sole inspiratory gases delivery to one of a user's nares and the other of the pair configured for sole expiratory gases received from the other of the user's nares.

In a fifth aspect, this disclosure relates to a patient interface comprising:

a first nasal interface component to provide a fluid connection with a user's first nare, an inspiratory gases pathway in fluid communication between the first nasal interface component and a gases source to provide inspiratory gases to the user's first nare, a second nasal interface component to provide a fluid connection with the user's second nare, and an expiratory gases pathway to receive expiratory gases from the user's second nare, wherein the inspiratory gases pathway is mechanically disconnected from fluid communication with the second nasal component.

In a sixth aspect, this disclosure relates to a patient interface comprising:

a first nasal interface component to provide a substantially sealed fluid connection with a user's first nare, an inspiratory gases pathway in fluid communication between the first nasal interface component and a gases source to provide inspiratory gases to the user's first nare, a second nasal interface component to provide a substantially sealed fluid connection with the user's second nare, and an expiratory gases pathway to receive expiratory gases from the user's second nare, wherein the inspiratory gases pathway is not in fluid communication with the second nasal component.

In a seventh aspect, this disclosure relates to a method of delivering a unidirectional gases flow through a dedicated inlet nasal interfacing component and communicating an exhaled flow away via a dedicated outlet nasal interfacing structure, such that the gases flow turns or changes direction within a user's nasal passage(s).

Both of the nasal interfacing components may be configured for sealing with a user's nares.

The unidirectional gases flow may be selectively directed to either a first nasal interfacing component or a second interfacing component, the nasal interfacing component selected becoming the dedicated inlet nasal interfacing component, and the other of the nasal interfacing components becoming the dedicated outlet nasal interfacing component.

A flow diverter may be operable to selectively divert the gases flow to either of the first nasal interfacing component or the second interfacing component.

A partition or fluid path controller may be operable to facilitate a fluid connection between each of the first nasal interfacing component and the second interfacing component.

The partition or fluid path controller may be operable to control or adjust a bias flow of the gases flow being delivered to the nasal interfacing components.

In an eighth aspect, this disclosure relates to a method of administering a gases therapy to a user comprising:

delivering a first flow of gases to a first nasal interfacing component as an inspiratory flow, said first nasal interfacing component provided in fluid communication with a first of a user's nares;

receiving a second flow of gases from a second nasal interfacing component as an expiratory flow, said second nasal interfacing component provided in fluid communication with a second of a user's nares;

controlling the expiratory flow.

The expiratory flow may be controlled according to any one or more of the following gases parameters: pressure, flow rate.

The expiratory flow may be controlled to provide for an upstream parameter according to any one or more of: pressure, flow rate.

The parameter to be controlled may be that used to influences the gases pressure provided to or experienced by a user's airway.

The gases therapy delivered to the user may be a CPAP gases therapy.

The expiratory flow (or optionally the inspiratory flow) may be controlled by or directed to one or more of:

a bubbler or a bubble CPAP device or another pressure regulator (such as a Positive End Expiratory Pressure ("PEEP") valve), for regulation of the pressure provided to a user or experienced by a user's airway;

a ventilation or resuscitation device, such as for provision of any one or more of the following gases therapies for the user, including but not limited to, a continuous positive airway pressure (CPAP), BiPAP, NiPPV;

a flow generation device or flow driver, such as for provision of a desired gases therapy for the user, including but not limited to, a SiPAP.

In a further aspect, there is disclosed a patient interface, a system and/or method for providing a dedicated or sole inspiratory line or conduit for provision of inspiratory gases to a patient, and a dedicated or sole expiratory line or conduit for provision of expiratory gases to a downstream device, where the inspiratory line or conduit is sealing engageable with the first of a user's nares and the expiratory line or conduit is sealing engageable with the second of the user's nares.

In various embodiments, a patient or user interface may be modified or configured to receive and/or secure an adaptor and any necessary tubing, such as medicament delivery tubing or nasogastric tubing.

The tubing may extend from one or both side(s) of the user's face.

In some embodiments, the user or patient interfaces as described above and the securement systems may comprise a dynamic interface to absorb the patient's facial movements.

Such a dynamic interface may dampen the effect of facial movements on the positioning of the patient interface about the patient's nose.

In some embodiments, a dynamic interface may comprise or incorporate one or more hinges along the interface (or device) that react to facial movements, both natural and forced, and external forces exerted on the interface.

As used herein, the term 'hinges' refers generally to portions on the interface that are configured to bend in one or more directions. The hinges can be configured to bend in a predefined direction or directions, and in some embodiments the hinges can be restricted from bending in certain directions.

In another aspect, a use or patient interface suitable for use with the various aspects above, may broadly consist in a patient interface, such as a nasal cannula, comprising a body to be positioned upon a user (preferably such as a user's face), the body including at least one (and preferably a pair of) nasal prong(s), the or each nasal prong including a lumen capable of being fluidly connected thereto for fluid communication with a supply of breathable gas, the or each nasal prong to be in a configuration either inserted into, or to direct a flow of gas toward, a nare or the nares of the user's nose, wherein the body includes at least one element (optionally mechanically) responsive to force(s) or movement(s), or both, experienced by at least a first region of the patient interface; optionally or alternatively wherein the body includes at least one element (optionally mechanically) responsive to force(s) or movement(s), or both, experienced by at least a first region of the patient interface from being transferred to at least one other region of the patient interface.

The element may facilitate the reduction in transfer of a force or movement, or both, applied to at least a first region of the interface from being transferred to at least another region of the interface.

The element may respond in a manner to localise the force or the movement, or both, experienced by the at least first region.

The element may respond to minimise or prevent transfer of the force or the movement, or both, from the at least first region to at least one other region of the patient interface.

The element may respond in a manner to maintain the at least one (and preferably the pair of) nasal prong(s) in the configuration of insertion in a nare or nares of the user's nose, or in the configuration of directing a flow of gas toward a nare or nares of the user's nose.

The response may be such that the at least one (or preferably the pair of) nasal prong(s) maintain a stable position within or adjacent to the nares of a user's nose to which the prong(s) is directed.

The response may be such that the interface maintains an operational position upon the user.

The force or movement, or both, experienced by at least a first region of the interface may be either, or both, of:

an applied force(s) or a movement(s) between the nasal prong(s) and body of the patient interface, or an applied force(s) or a movement(s) between the body of the patient interface and the nasal prong(s).

The element may be deformable or deformed in response to the force or movement, or both, being experienced by at least the first region of the interface.

The element may have a predetermined or preferential mode of deformation in response to an applied force or movement, or both, being experienced by at least a first region of the interface.

The element may be deformable by one or a combination of a compression or a tension or a torsion or bending or other flexion.

The element may respond to the force or movement, or both, experienced by at least the first region of the interface by one or a combination of: changing shape, changing position, changing configuration or deforming.

The element may comprise one or a combination of any of the following:

hinges, pivots, articulated joints or articulately connected portions of the body or portions associated with the body, swivels, ball-and-socket type joints, pin-in-barrel type joints, materials which are relatively less flexible than other portions of the interface, materials which are relatively more flexible than other portions of the interface, materials of characteristics which change upon application of a force or movement, such as by increasing their resistance to the applied force or movement (or both), or by reducing their resistance to the applied force or movement (or both), or materials which are elastically deformable in response to the applied force or movement (or both), or materials which are preferentially deformable in particular or predetermined geometries and yet which may optionally resistant to deformation in other particular or predetermined geometries.

The element may be one or more of the following:

a pivot (or swivel) or region capable of pivoting (or swiveling), or a hinge or a hinged region or region capable of being hinged relative to another component of the interface or another region of the interface, or an articulation or articulated joint or region capable of being articulated.

The element may provide for a de-coupling of forces or movement (or both) which is applied to at least the first region of the interface from being transferred to at least one other region of the interface.

The element may be provided or is operable or works to prevent or minimise transfer of force of movement from the at least first region of the interface to at least one other region of the interface.

The element may be a structure or a mechanism of the interface or may be a region of the interface.

The element may be deformable about at least one axis or at least one plane.

The element may be deformable about a preferential first geometry.

The element may be deformable by one or a combination of a compression or a tension or a torsion or bending or other flexion.

There may be two or more elements located about the interface.

The elements may be connected together in a manner so as to provide for a combined response to the force or movement (or both).

The element may respond to the force or movement (or both) in a different mode, thereby providing for a combined response.

The elements may be operatively coupled to each other, or to other portions of the interface to provide for a or the combined response.

At least one of the elements, or each such element, may be provided as one or more of:

an isolator or a region of isolation, an absorber or a region of absorption, a dampener or a region of dampening, or the any other structure or mechanism providing for a reactive response to a force(s) or movement(s) imparted to at least a first region of the patient interface from being transferred to at least a second or another region of the patient interface.

The response of one or each element may be at least one (or a combination) of an isolation or an absorption or a dampening or a reduction of the force(s) or movement(s) imparted to at least the first region from being transferred to at least one other region of the patient interface during use by a user.

Such force(s) or movement(s) may be resultant from a user of the interface changing their facial geometry to which the interface is retained or located or positioned, or such as by a user pulling or applying a force or movement on or to the interface or an associated headgear thereof, or a breathing circuit or other componentry of the interface applying a force or movement, such as by weighing down upon, a portion of the interface or a headgear associated thereof.

The applied forces or movement between the nasal prong(s) and body of the patient interface, or between the body of the patient interface and the nasal prong may be resultant from changes in user facial geometry, such as during speech, eating, sleeping or other facial distortions between relaxed and exaggerated conditions.

The at least one element, or at least one of the elements, may be located in a bridge region of a nasal cannula patient interface, to facilitate movement of the bridge region in response to a force or movement or both (in addition, may be such as substantially adjacent the septum region of a user).

The interface may comprise a plurality of elements utilised on their own or in combination with other elements to provide for the response.

The at least one element may be a hinged portion located or positioned as a bridge between a left body portion and a right body portion, each of the body portions together forming the body of an interface to be located upon a user's face, such a hinged portion providing for a preferential region of deformation in response to at least a first region of the body or a portion of the body, experiencing a force or movement (or both) resulting from a change in the facial geometry of the user.

The patient interface may be substantially conformed or conformable to the geometry of a user's face, such that the element responds to the force or movement (or both) to substantially maintain the interface in a preferred therapy delivery configuration for a user.

In a further aspect, the patient interface as may be utilised with the various aspects described above, may broadly consist in a patient interface, such as a nasal cannula, comprising: a pair of respective left and right body portions, to be located, in-use upon a face of a user, and a bridge portion extending between each of the left and right body portions, a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, the bridge portion allowing movement of the respective body portions with the inner-more ends of the body portions being brought toward each another, yet resisting movement of the respective body portions with the inner-more ends being moved away from each other.

A displacement of the position of one or both of the left and/or right body portions, when the patient interface is in-situ upon a user's face, may be transmitted to the bridge in a manner so as to minimise movement of the prong or prongs in relation to the user's nare(s).

The bridge portion may extend and connect inner-more ends of the respective body portions.

The bridge portion may be a material that, in a direction extending between the respective inner-more ends of the body portions, is able to undergo a compression and resists or withstands a tension applied thereto.

The direction extending between the respective inner-more ends of the body portions is a longitudinal direction extending along the respective body portions.

The bridge portion may comprise a textile material.

The bridge portion may be axially expandable/stretchable but resilient to resist movement of the respective body portions with the inner-more ends being moved away from each other.

A length of the bridge portion between a connection point on the left body portion and a connection point on the right body portion may be larger than a distance between the nasal prongs.

The bridge portion may comprise a flexible polymeric material.

In a further aspect, the patient interface as may be utilised with the various aspects described above, may broadly consist in a patient interface, such as a nasal cannula, comprising: a pair of respective left and right body portions, to be located, in-use upon a face of a user, a bridge portion extending between each of the left and right body portions, and a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, wherein one, and preferably both, of the respective body portions include a user facial contacting surface oriented relative to the respective nasal prong such that, when in situ, a torsional force applied to the left and/or right body portions substantially retains the nasal prong(s) in, or in a position to direct a flow of gas into, the nare(s) of the user's nose.

Rotation of the body portion, or rotation of both body portions, towards a user's face, may maximise a contact surface area between the facial contacting surface(s) and the face of the user and locates the nasal prong(s) into, or in the position for directing the flow of gases into, the nare(s) of the user's nose.

The bridge section may be of a relatively smaller diameter than the left and right body portions.

Each body portion may comprise a channel fluidly connected to the respective nasal prong at one end and open for fluidly coupling a gas flow path of a breathing circuit at an opposing end.

At least one, or each, of the left and right body portions may include an axially twisted facial contacting surface moveable between a relaxed position and a torsioned position in which a surface area for locating adjacent the user's face is increased.

The facial contacting surface may be axially twisted along a length of the body portion from an inner end of the body portion to an outer end of the body portion.

The facial contacting surface may extend helically along the length of the body portion.

The facial contacting surface, in the relaxed position, may face away from a direction of extension of the nasal prong(s) at the distal end, and in the torsioned position, may face in the direction of extension of the nasal prong(s) and is substantially planar along a substantial length of the body portion.

The nasal prong or the nasal prongs may be angled relative to the respective left and right body portions to exert torsion on the body portion upon insertion of the nasal prong(s) into the nare(s) of the user's nose.

The facial contacting surface of the respective left and/or right body portion may be contoured to engage the user's facial cheek.

In a further aspect, the patient interface as may be utilised with the various aspects described above, may broadly consist in a patient interface, such as a nasal cannula, comprising: a pair of respective left and right body portions, to be located, in-use upon a face of a user, and a bridge portion extending between each of the left and right body portions, a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, and a series of discrete and separate facial contacting surface(s) movable relative to each other to respond to force(s) or movement(s), or both, experienced by facial contacting surface(s) and at least partially alleviate the transfer of such force(s) and/or movement(s) to the nasal prong(s).

In a further aspect, the patient interface as may be utilised with the various aspects described above, may broadly consist in a patient interface, such as a nasal cannula, comprising: a pair of respective left and right body portions, each body portion to be located, in-use upon a face of a user, and a bridge portion extending between the left and right body portions, and a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, wherein the cannula includes at least one hinged region pivotable relative to another region of the cannula about at least a pair of substantially orthogonal axes, or along a pair of substantially orthogonal planes, or both, to respond to force(s) or movement(s), or both, experienced by the other region and at least partially alleviate the transfer of such force(s) and/or movement(s) to the nasal prong(s).

At least one hinged region may be pivotable about three substantially orthogonal axes, or along three substantially orthogonal planes, or both.

The bridge may comprise a bridge hinge adjacent the nasal prong or between the pair of nasal prongs.

The bridge hinge may be predisposed to have an acute curvature.

The bridge hinge may be predisposed to bend inward toward the user, and downward away from the nare(s) in situ.

The bridge may further comprise a second hinge on one side of the bridge hinge, or a pair of opposed second hinges on either side of the bridge hinge and adjacent the nasal prong or nasal prongs.

The second hinge or each hinge of the pair of second hinges may be predisposed to have an acute curvature.

The second hinge, or each hinge of the pair of second hinges may be predisposed to bend upwardly towards the nare(s) of the user and outwardly away from the user in situ.

The bridge may comprise a third hinge adjacent the left or the right body portion, or a pair of third hinges disposed adjacent the respective left and right body portions.

The third hinge or each of the pair of third hinges may be predisposed to have an acute curvature.

The third hinge or each of the pair of third hinges may be predisposed to bend downward away from the nare(s) and outward away from the user in situ.

One end of the bridge portion may extend substantially orthogonally from the third hinge, or either end of the bridge portion extends substantially orthogonally from either one of the pair of third hinges and inwardly towards the facial cheek(s) of the user in situ.

Each body portion may comprise a facial pad contoured to engage a region of the user's face.

Either end of the bridge portion may extend along at least a portion of the facial pad.

The bridge portion may be substantially hollow at least at either end of the bridge portion to transport a flow of gases there through.

Either end of the bridge portion may be configured to couple a gas flow path of a breathing circuit.

The nasal prong, or each nasal prong, may extends from, and may be fluidly coupled to, a respective end of the bridge portion.

The bridge portion may comprise an annular cross section along at least a substantially portion of the length of the bridge portion.

The bridge may further comprise a fourth hinge adjacent the third hinge, or a pair of fourth hinges adjacent the respective pair of third hinges.

The fourth hinge or each hinge of the pair of fourth hinges may be predisposed to have an acute curvature.

The fourth hinge, or each hinge of the pair of fourth hinges may be predisposed to bend downwardly away from the nare(s) of the user and inwardly toward the facial cheek(s) of the user in situ.

Each body portion may comprise a facial pad contoured to engage upon a region of the user's face.

In a further aspect, the patient interface as may be utilised with the various aspects described above, may broadly consist in a nasal interface configured to stabilize prongs on a patient's face when forces are exerted on the interface, the nasal interface comprising: an elongate body having an overall curvature that generally corresponds to a patient's facial profile, the body configured to be coupled to a gases flow source and comprising at least one lumen extending at least partially through the body; a pair of prongs extending from the body and in fluid communication with the at least one lumen; and one or more hinges, at least one hinge disposed between the pair of prongs that is predisposed to bend in a predefined direction.

The patient interface may further comprise one or more facial pads configured to rest on a patient's face.

The at least one hinge disposed between the pair of prongs may have a curvature that is generally inverted from the overall curvature of the elongate body.

The at least one hinge disposed between the pair of prongs may be configured to bend inward towards the patient's face.

The nasal interface may have a generally gullwing shape.

The nasal interface may have a wavy shape.

The nasal interface may have a curved space frame-like support structure.

The nasal interface may bend in more than one dimension.

The one or more hinges may comprise one or more of a notch, a variable cross-sectional area, a variable thickness, two or more materials with different flexibilities, an elastic hinge that is configured to be pre-stressed before application to a patient, a barrel and pin, and/or a ball and socket.

In a further aspect, the patient interface as may be utilised with the various aspects described above, may broadly consist in a nasal interface comprising: an elongate body comprising at least one lumen extending at least partially through the body, the body configured to be coupled to a gases flow source; one or more prongs extending from the body and in fluid communication with the at least one lumen; and one or more hinges that are predisposed to bend in predefined directions; wherein the one or more hinges are configured to stabilize a position of the one or more prongs on a patient's face when forces are exerted on the nasal interface.

The nasal interface may further comprise one or more facial pads configured to rest on a patient's face.

At least one of the one or more hinges may be located adjacent to or between the one or more prongs.

At least one of the one or more hinges may be configured to bend inward towards the patient's face.

At least one of the one or more hinges may be configured to bend downward.

The nasal interface may have a generally gullwing shape.

The nasal interface may have a wavy shape.

The nasal interface may have a curved space frame-like support structure.

The nasal interface may bend in more than one dimension.

The nasal interface may comprise two separate sides that are coupled by an over-strap bridge.

The one or more hinges may comprise one or more of a notch, a variable cross-sectional area, a variable thickness, two or more materials with different flexibilities, an elastic hinge that is configured to be pre-stressed before application to a patient, a barrel and pin, and/or a ball and socket.

In a further aspect, the patient interface as may be utilised with the various aspects described above, may broadly consist in a nasal interface comprising: an elongate body comprising at least one lumen extending at least partially through the body, the body configured to be coupled to a gases flow source; and one or more prongs coupled to the body and in fluid communication with the at least one lumen; wherein the elongate body has a shape that generally corresponds to an anatomical contour of a patient's or a group of patients' facial profile.

The group of patients may be one of premature babies, neonates, infant, paediatrics or adults.

The tubular body may be initially malleable.

The shape of the tubular body may be set through a hardening process.

With reference to the above various patient or user interfaces (including nasal interfaces), where a first and a second nasal prong or nasal interfacing element are noted as being provided in fluid connection, it will be appreciated that the description herein provides for a modification in which a valve or a 'bridge valve' may be implemented to control flow or passage of gas between each of the nasal prongs or nasal interfacing elements. In this way, a bias flow between the nasal prongs or nasal interfacing elements can be controlled. For example, such a valve at the bridge can be used to strop or prevent any flow or passage of gas between the nasal prongs or the valve be operated to allow for a flow or passage of gas between the nasal prongs. In this way, a bias flow can be controlled for such interfaces.

The term "gullwing" as used in this specification means a shape that comprising of two crests (or crest-like regions) and a trough (or trough-like region) located between such crests, or two troughs (or trough-like regions) and a crest (or crest-like region) located between such troughs, when viewed either as a top or bottom view of the patient interface (for example when the sequence of respective crests or troughs are drawn as a line diagram). Such crests or troughs may transition between each other in a relatively arcuate or curved manner. Optionally, such crests or troughs may be shaped or curved to substantially match or assimilate to facial contours or profile of a typical user's face.

The term "wavy" as used in this specification means a shape that comprises of a plurality of crests (or crest-like regions) and troughs (or trough-like regions), and comprising of at least one trough (or trough-like region) or of at least one crest (or crest-like region) disposed between respectively a pair of crests (or crest-like regions) or at least one trough (or trough-like region) disposed between respectively a pair of crests (or crest-like regions), when viewed from when viewed either as a top or bottom view of the patient interface (for example when the sequence of respective crests or troughs are drawn as a line diagram). Such crests or troughs may transition between each other in a relatively arcuate or curved manner. Optionally, such crests or troughs may be shaped or curved to substantially match or assimilate to facial contours or profile of a typical user's face.

The term "space frame" as used in this specification means a structure that provides for a substantially hollow scaffolding or supporting structure upon or to which a gas delivery line or conduit may be connected or otherwise attached or supported for delivery a gas to a user or a gas outlet of a patient interface (e.g. a nasal prong or pair of nasal prongs).

Where reference is made to a "pre-form", such a preformed element means an element that is manufactured or moulded or constructed or assembled so as to provide for a shape or configuration capable of providing for a deformed or displaceable response in a preferential geometry.

Where reference is made to a "preferential geometry", this means a predetermined or preferred plane (or planes) or axis (or axes) of hinging or bending or deforming or displacement.

Where reference is made to a "de-coupling", this means that there is at least a partial isolation or dampening or absorption (or some other mode), preferably a mechanical mode but not limited to this mode, in which forces or movements (or both) experienced or applied to a first region or part of the interface are at least minimised from being entirely transferred to another region or part of the interface.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

Figure 1:
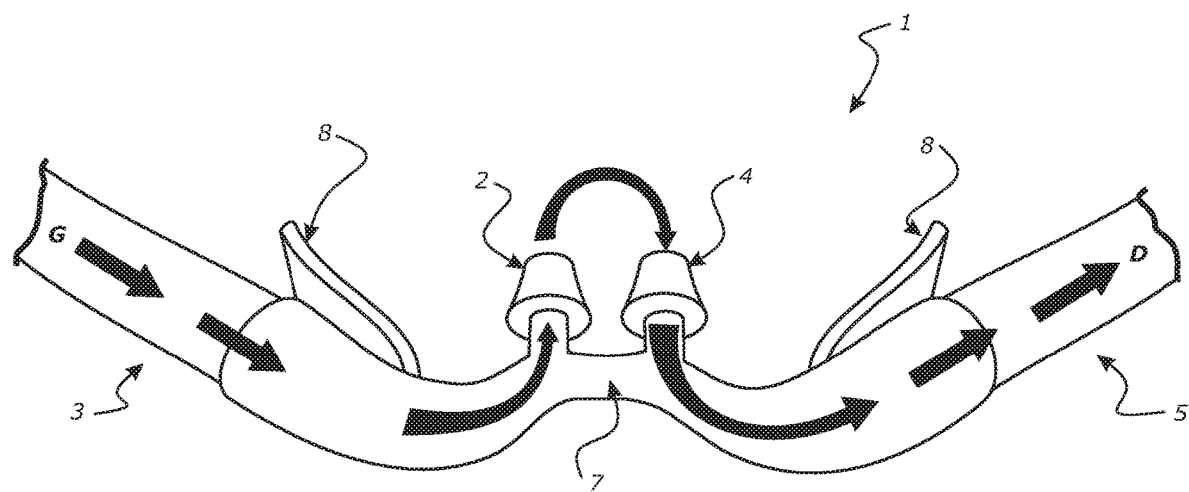
FIG. 1 illustrates one embodiment of a patient interface.

The following description is made with reference to the accompanying figures.

This disclosure relates to a system and/or apparatus and/or method providing a gases therapy to a user. In particular, though not limited to, application of a gases therapy using a patient interface provided with capabilities of directing or delivering a flow of gases from a source to one of a user's nare as an inspiratory flow, and collecting and directing a flow of gases from the other of the user's nares as an expiratory flow.

Advantageously, such a patient interface and/or system and/or method may facilitate one or more of the following:

clearance of airway dead space, reduction in airway dead space (i.e. a user's physiological airway dead space), reduction or substantial elimination of the dead space in a patient interface (i.e. the interface's structural dead space due to internal geometries or flow path of gases through the patient interface), ease of detection of gases delivery to a user or detection of an intended gases therapy being delivered or provided to the user, an alternative mode of delivering or providing a CPAP gases therapy to the user, a mechanism for delivery of a medicament to a user's airway, ability to provide, as part of a single patient interface, the ability to provide a first mode or gases therapy to a user (where two or both nasal interfacing elements are utilised to deliver a flow of gases to the user/patient), and then in another mode provide for delivery of an inspiratory gas to the user/patient via a sole or dedicated nasal interfacing element to a first of a user/patient nare, with the option to provide for a bias flow between the inspiratory nasal interfacing element and a second nasal interfacing element.

Reference to dead space in this specification can refer to either the user's physiological (i.e. their airway) dead space, or to the dead space which may exist in a patient interface. Reduction of dead space in this context of both a user's dead space and that of the patient interface providing for a particular gases therapy is desirable.

While patient interfaces, systems and methods disclosed herein may have particular relevance to neonatal users, it will be appreciated that the end users (or patients) may vary from neonate users to paediatric users to adult users. As such, the various components such as conduit or nasal interfacing components or other elements of a patient interface or the components or devices provided as part of a system or for provision of an intended method of particular gases therapy can be selected to provide for appropriate gases flows, gases pressures, sealing forces (e.g. an adult user may be able to more comfortably wear a patient interface or a suitable interface retention system providing higher or greater sealing forces or higher gases pressures or higher gases flows, relative to younger users). It will also be appreciated the greater gases flows or pressures which may be needed for older users may not be suitable for younger users, as such the particular controls or demands on components or devices in the patient interface or the system may be different. For example, larger bore conduit may be needed for delivering greater flow rates of gases to the user, while for younger user the flow rates may be less, so smaller bore conduit may be suitable, including but not limited to taking into account the resistance to flow (RTF) of conduit that is to be used. Each of these kind of considerations can be taken into account depending on the user requirements.

The system, apparatus or method as described above can be further modified to control for a positive airway pressure type gases therapy to be provided to a user. For example, a device provided in fluid communication with an expiratory flow or the nasal interfacing component provided as part of an expiratory line or conduit is operable to provide for a closed medical breathing circuit.

The system and/or apparatus and/or method of this disclosure also enables the selective provision or delivery of a gases source to one of the user's nares via a first nasal interfacing component, with the selective provision or receipt of collection of a flow of gases from the other of the user's nares via a second nasal interfacing component.

The system and/or apparatus and/or method of this disclosure also enables for a selective control of a bias flow of gases being directed to one nasal interfacing component of a pair of nasal interfacing components of a patient interface. For example in a bridge region of such a patient interface, a valve (referred to herein as a 'bridge valve') is operable to adjustably control a fluid communication between gases paths of each of the pair of nasal interfacing components.

Physiological (also known as anatomical) dead space is the portion of the airway that is shared by the inspiratory and expiratory flow paths and thus can potentially be filled with $CO_2$ at the end of the expiratory phase, such that this $CO_2$ will then be inhaled during the next inspiratory phase or next inspiratory portion of the breath.

Structural dead space can be reduced by mechanical design, i.e., by reducing the portion of the interface that is shared by the inspiratory and expiratory flow paths. The patient interface as disclosed herein in various embodiments can entirely eliminate the shared portion. In particular, a traditional sealing cannula will have dead space in both prongs and in the "bridge" (the gases flow path connecting the prongs to each other). As described herein, the patient interface can be configured to have no gases flow path in the bridge. In addition, as the patient interface as described herein provides for a gases flow that is unidirectional (and provided to a single nare of a user) there is no shared space in the prongs.

A patient interface and gases therapy (e.g. respiratory gases therapy) can also effectively reduce the anatomical dead space through management of the gases flow, e.g. a higher bias flow rate or the jetting effect of a traditional flow driver interface. This type of patient interface can reduce anatomical dead space by operating to effectively force all of the bias flow through the patient's airway, thus "washing out" $CO_2$ during and after the expiratory phase (as long as the bias flow rate is high enough to meet peak inspiratory demand).

The following provides additional disclosure and principles of suitable systems and/or apparatus and/or methods for implementation of the above.

Bias flow is referred to as the minimum gases flow rate through the patient interface during both inspiratory and expiratory phases. For a traditional interface, during the expiratory phase the bias flow passes straight through the interface without reaching the patient. However, with respect to the patient interface as described herein, it is possible to deliver 100% of the bias flow into the patient during both breathing phases.

The bias gases flow rate or bias flow rate is usually roughly constant for a given pressure setting and should be at or close to peak inspiratory demand (the flow rate that will support the PIP), (being peak inspiratory pressure, which is the highest negative pressure applied to the lungs during inhalation) to ensure positive pressure throughout the breath cycle. That is, if the bias flow rate is too low, then at the inspiratory peak there will be negative pressure in the gases flow.

With a traditional interface, excess bias flow (above peak inspiratory demand) has little effect on the patient. However, with respect to the patient interface as described herein, excess bias flow may increase dead space flushing, which can decrease the respiratory rate. A lower respiratory rate may also decrease peak inspiratory demand, potentially reducing the bias flow rate needed to maintain positive pressure.

On the other hand, a reduced bias flow rate (that still meets peak inspiratory demand) may be beneficial to reduce likelihood of injury to the patient's airway, and in the case of oxygen therapy reduce the likelihood of retinopathy of prematurity as a result of oxygen toxicity.

In one embodiment, there is provided a patient interface 1 that comprises a first nasal interfacing component 2 to be provided in fluid communication with a user's first nare (not shown), and an associated first conduit 3 provided for an independent/dedicated fluid connection with the first nasal interfacing component 2; and a second nasal interfacing component 4 to be provided in fluid communication with a user's second nare (not shown), and an associated second conduit 5 provided for an independent/dedicated fluid connection with the second nasal interfacing component 4. In this arrangement, configured as a sole inspiratory line or conduit for delivery of inspiratory gases flow from a gases source G (not shown) to one of the user's nares is one of either: a) the first nasal interfacing component 2 with said associated first conduit 3, or b) the second nasal interfacing component 4 with said associated second conduit 5. In this arrangement, configured as a sole expiratory line or conduit for receiving gases from the other one of the user's nares is the other of the one of the first nasal interfacing component 2 with said associated first conduit 3 or the second nasal interfacing component 4 with said associated second conduit 5. Such an embodiment may for example be of the type illustrated by FIG. 1.

Figure 8:
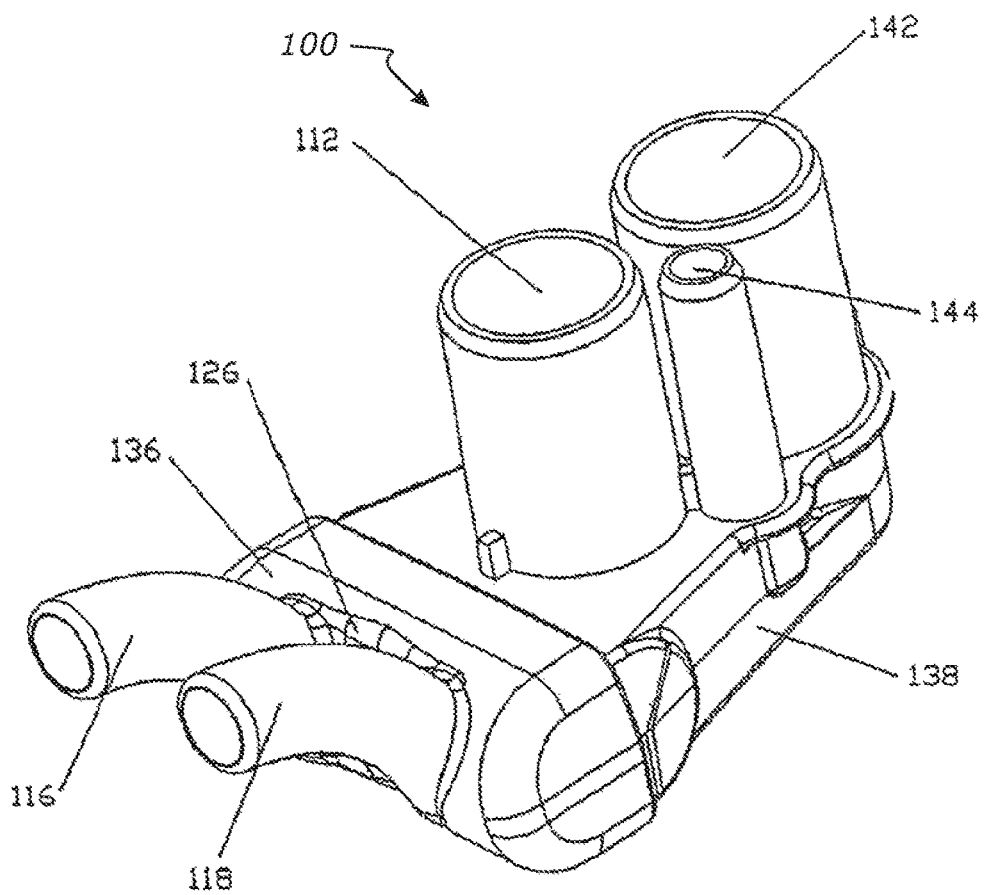
FIG. 8 illustrates an alternative nasal interfacing patient interface.
Figure 9:
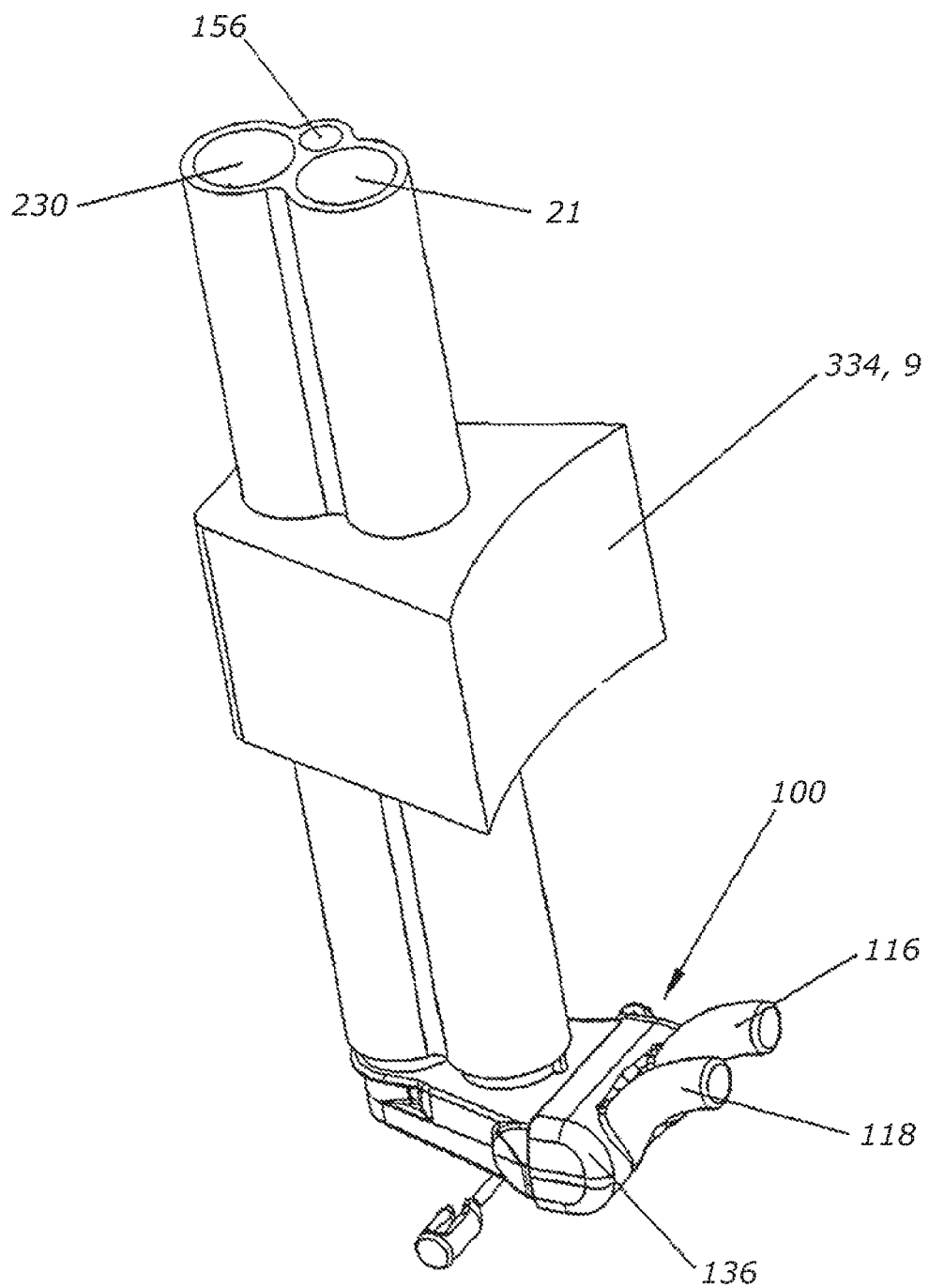
FIG. 9 illustrates the interface of FIG. 8 in more detail.
Figure 10:
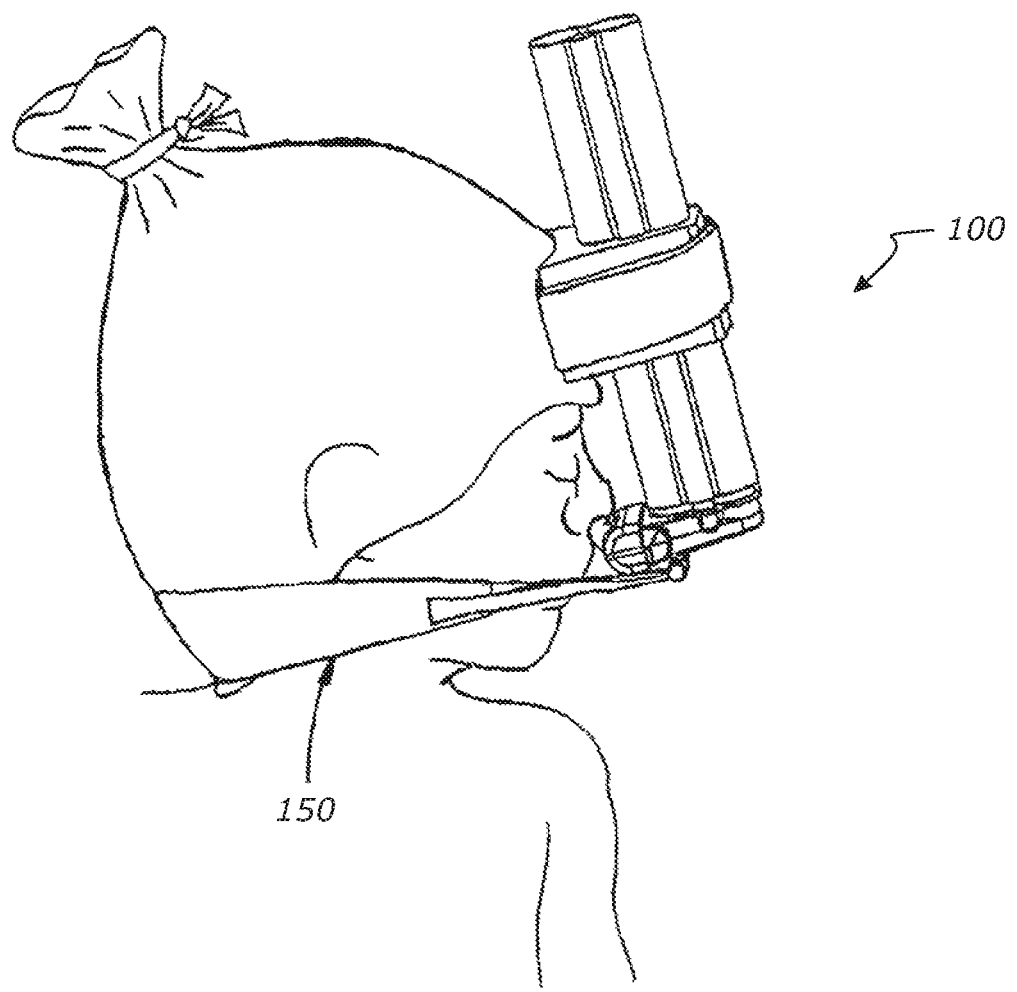
FIG. 10 illustrates the interface of FIG. 9 when worn by a user.
Figure 11:
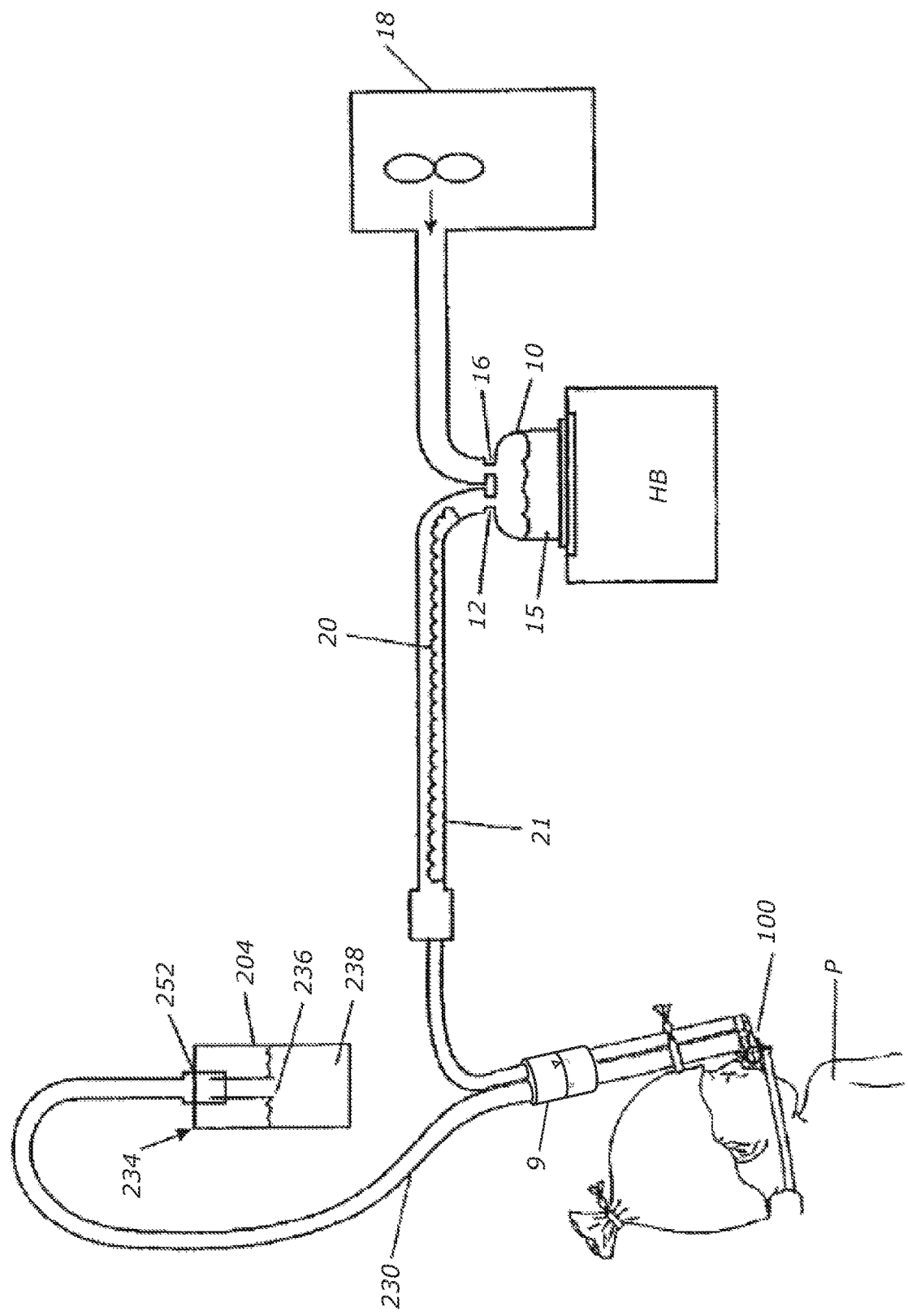
FIG. 11 illustrates a system incorporating the interface of FIG. 9.
Figure 12:
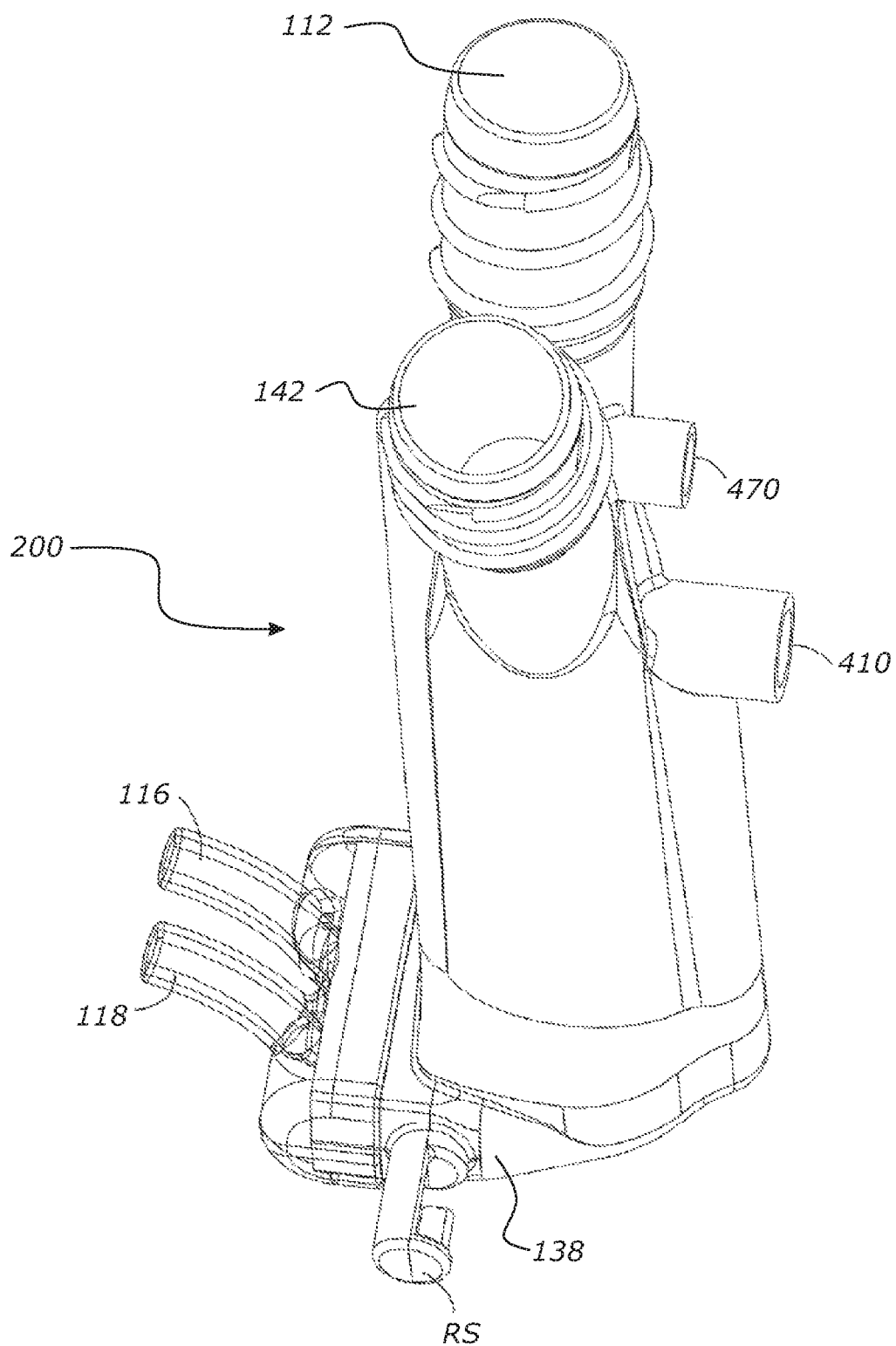
FIG. 12 illustrates a further alternative to the interface of FIGS. 8 and 9.
Figure 13:
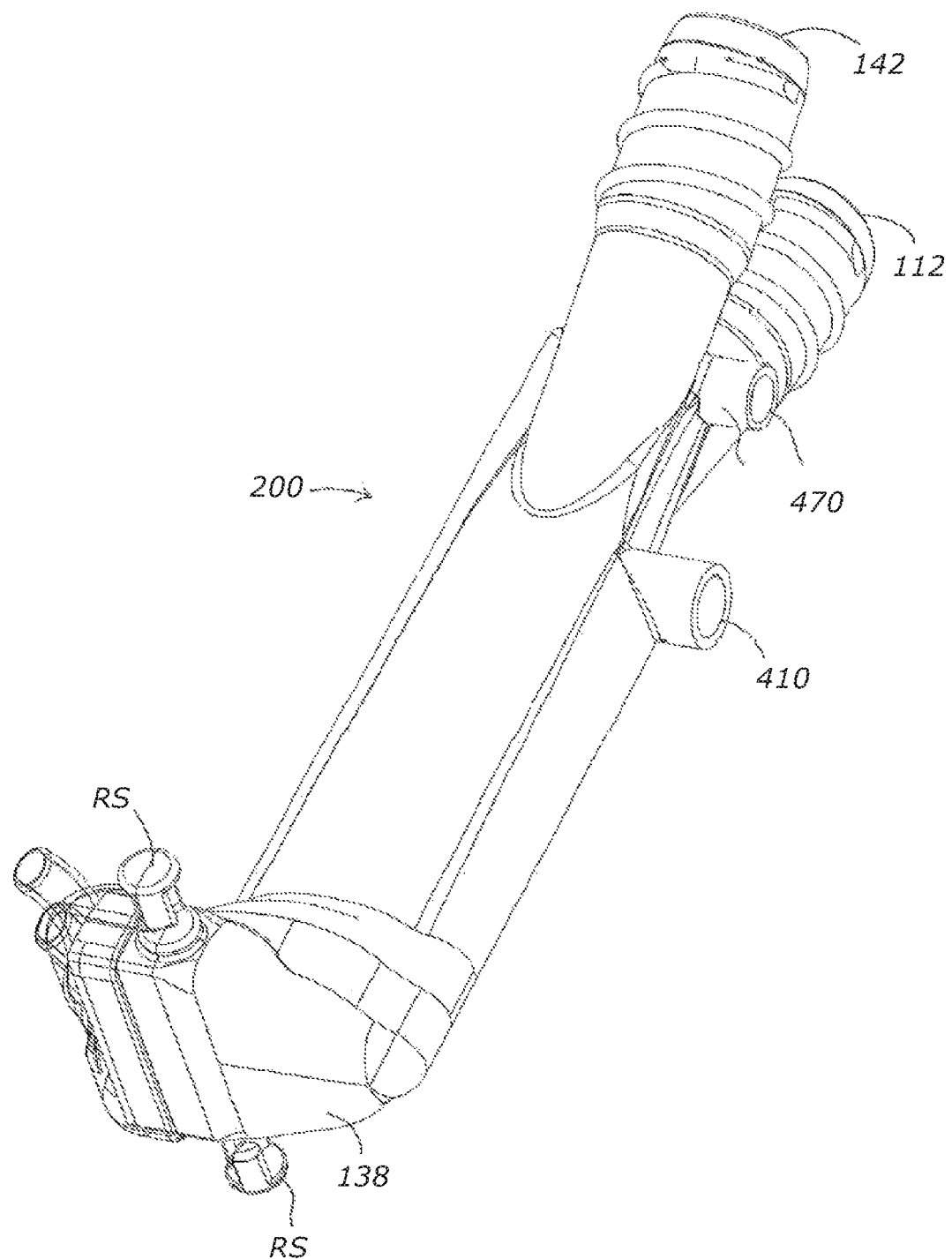
FIG. 13 illustrates another view of the interface of FIG. 12.
Figure 14:
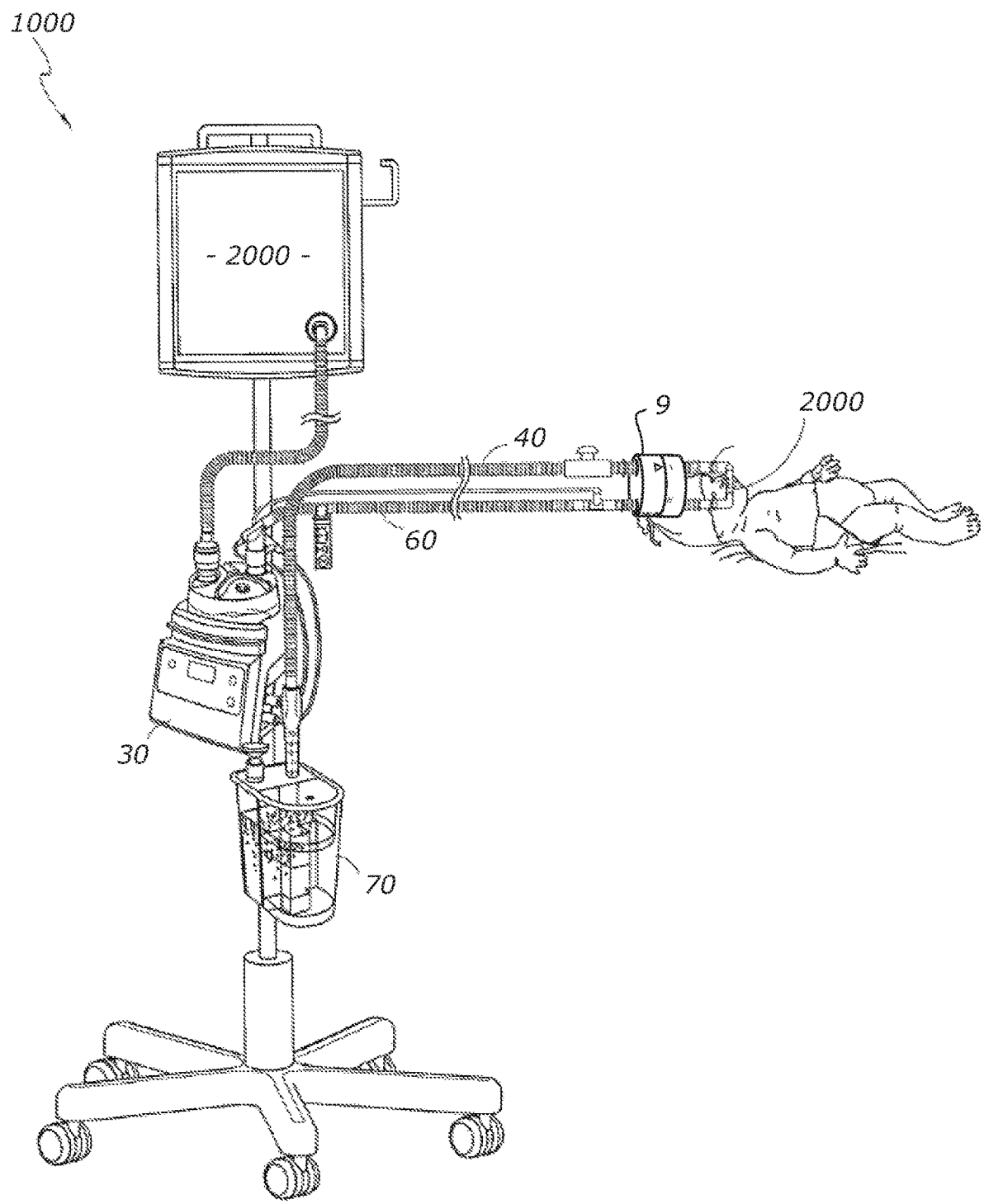
FIG. 14 illustrates a system incorporating the interface of FIG. 12.

In another embodiment, such a patient interface may be of the type as for example shown by any one of FIGS. 8-10, or when used in a system as shown for example in FIG. 11; or in another embodiment such as of the type illustrated by any one of FIGS. 12-13, or when used in a system as shown for example in FIG. 14.

FIGS. 8-10 illustrate a part of a patient interface comprising of a pair of nasal interfacing components 116, 118. The nasal interfacing components extend from a body portion 136 from a relatively flexible section 126. The nasal interfacing components are shown without a seal element for providing a sealing capability with the user's nares, but it will be appreciated as described elsewhere in this specification that there are a variety of sealing systems which may be used to modify such a component. Each of the nasal interfacing components 116, 118 are provided with an associated conduit 112, 142. The nasal interfacing structures 116 and 118 may be large enough to form a seal with the nares. Alternatively the structures 116, 118 may include other sealing structures as defined herein. For the purposes of this embodiment, it is not necessary to specify which associated conduit is fluidly connected with which nasal interfacing component (as that may be a configuration a design of the interface itself), however it will be appreciated that each of the associated conduits 112, 142 are provided in direct (and dedicated/sole) fluid communication with one nasal interfacing component each. In this manner, the housing 138 may perform as a partitioned manifold to ensure the separate and sole fluid connection between each associated conduit 112, 142 and the respective nasal interfacing components 116, 118. Alternatively, the housing 138 may serve to provide for a relatively sturdy body configured to be capable of directing the independent conduits 112, 142 to their respectively fluidly connected nasal interfacing components. In the embodiment shown, the associated conduits 112, 142 are shown one behind the other, however as a side-by-side type arrangement is also envisaged (for example see the arrangement of FIGS. 12-13). A port 144 may optionally also be provided, for example this may allow for suitable sensors, detectors (as for example described elsewhere in this specification) to be provided in fluid communication with one or other or perhaps both of the associated conduits 112, 142 or very close to the nasal interfacing components 116, 118 for pressure or flow sensing or detection purposes.

FIG. 9 illustrates the patient interface of FIG. 8 in further detail. The associated conduits 112, 142 are shown extending substantially upwardly away from the nasal interfacing components. Also shown is a head-rest or support-type block 334. Incorporated into such a block 334 may be the diverter valve 9 are described elsewhere in this specification. Such a diverter valve operable to switch the flow of inspiratory gases from a source G to either of the associated conduits 112, 142 to then selectively supply inspiratory gases flow to a single nasal interfacing component (e.g. either of nasal interfacing components 116 or 118). Such a diverter valve also then operates to selectively provide for one of the nasal interfacing components and its associated conduit to operate to receive a flow of expiratory gases from the user and direct that flow to a downstream device (D) (not shown). For the purposes of this embodiment, a source of inspiratory gases flow may be directed from a supply conduit via lumen 21 (which then enters the block 334 and the diverter valve), while expiratory gases flow is directed through expiratory conduit via lumen 230. The additional conduit and lumen identified as item 156 in FIG. 9 may be a take-off for pressure measurement purposes.

FIG. 10 illustrates the patient interface 100 of FIGS. 8, 9 when worn by a user. A retention system in this instance is shown by a headgear 150. It will be appreciated that other forms of retention as described in this specification and may be utilised in combination with the interface 100.

FIG. 11 illustrates a patient interface 100 such as that of FIGS. 8-10 used in the system as shown. Shown is a flow generator 18 for providing a flow of a source of gases G to a humidifier chamber 10 via an inlet 16 for conditioning and subsequent exit at outlet 12. The humidifier chamber 10 comprises a humidification fluid (e.g. water). Heat is provided to the humidifier chamber 10 via a heater base HB. An inspiratory limb type conduit 21 may be used to transmit the conditioned gases to the interface 100. The conduit 21 may be optionally provided with a heating system, such as a heater 20 which can be controlled according to the condition requirements of the gases for delivery to the interface 100 worn by a patient P. The inspiratory gases are provided to the patient P via a dedicated associated conduit and nasal interfacing component as described herein. The expiratory flow of gases is then directed away from the patient via a dedicated nasal interfacing component and an associated conduit that is provided in fluid communication with an expiratory limb type conduit 230. The expiratory type limb conduit 230 is provided in communication with a downstream device D, which in this example may be a bubbler 234. The bubbler 234 comprises of a gases inlet 252, and an extension tube or piece to reach below water level 236 of the water 238. Depending on the depth of the extension tube or piece the effective back-pressure on the closed system may be controlled as desired for a respiratory gases therapy to be provided to the patient P.

FIG. 12 illustrates an interface 200 similar concept to the interface of FIGS. 8-10, however in this arrangement the associated conduits 112, 142 are arranged in a side-by-side configuration. The same types of fluid connection between associated conduit and nasal interfacing components 116, 118 are provided (i.e. each are fluidly separate). Such separation can be provided by a partition (not shown) within the body or housing. The arm labelled as RS is configured for receipt of a suitable retention system, for example a headgear type arrangement. Various take-offs such as 410 and 470 are provided for sensors or other detectors for pressure or flow type sensing or detection purposes (as is described elsewhere in this specification). FIG. 13 illustrates the interface 200 of FIG. 12 from a different angle.

In various embodiments, such as for example that shown in FIGS. 12 and 13, a take-off or port, such as take-off 410 may be utilised as a port to introduce a medicament to the flow of gases being delivered to the user. Optionally, such a medicament may be an aerosolized medicament, such as aerosolized surfactant, or may be any other suitable medicament capable of being introduced into a flow of gases for delivery to a user's airway or entrance to the user's airway.

In various embodiments, where a port such as 410 is provided for a patient interface, such a port 410 may be utilised for the administration or delivery of a medicament into a flow of gases being delivered to a user or patient. For example, the medicament may be aerosolized or otherwise provided in a suitable for administration to a user or patient airway.

The medicament may be provided into a flow of gases being supplied as an inspiratory flow to a user or patient. In one embodiment, the medicament delivery port (such as port 410 shown in FIGS. 12, 13) may be in fluid connection or communication with one or both of the nasal interfacing elements 116, 118.

Where a medicament delivery port is provided in fluid connection or communication with a single nasal interfacing element, a diverter valve would need to be operated or correctly matched so as to provide the source of supply of gases to the nasal interfacing element which is associated with the medicament delivery port, thereby to ensure the medicament is delivered into the flow of gases being delivered as an inspiratory flow to the user or patient. Alternatively, where a medicament delivery port is provided in fluid connection or communication with a two (or both) nasal interfacing elements, a medicament diverter valve would need to be operated or correctly matched so as to provide the medicament which may be administered via the port (such as 410) to the nasal interfacing element or the associate line or conduit being supplied with a source of supply of gases to the nasal interfacing element, thereby to ensure the medicament is delivered into the flow of gases being delivered as an inspiratory flow to the user or patient.

The medicament may be provided into a flow of gases being supplied to a nasal interfacing element selected as an inspiratory nasal interfacing element. Such a selection may be achieved by the use of a diverter valve upstream of the inspiratory nasal interfacing element.

Where a particular one of a pair of nasal interfacing elements of a patient interface is selected as the inspiratory nasal interfacing element by a diverter valve, the diverter valve may be suitably associated with or coupled to a mechanism associated with the medicament port to direct medicament administered via a port to the selected inspiratory nasal interfacing element.

Alternatively, a valve or a diverter valve or a selector may be operably adjustable at a port or elsewhere on the patient interface for selecting one of the nasal interfacing elements, or an associated conduit with one of the nasal interfacing elements, to be fluidly connected with the port to receive a medicament administered via the port. Such a valve or diverter valve or selector allows for the matching or fluid coupling of a line or conduit connected to the port with a nasal interfacing element selected as the inspiratory line or conduit, for delivery of a medicament via the port to the user or patient.

For example, port 410 shown in FIGS. 12 and 13 provides for a line or conduit or passageway for directing a medicament which may be administered into the port 410.

In one embodiment, the line or conduit extending from the port 410 may provide for a dedicated or sole fluid connection or communication with a single nasal interfacing element (e.g. one of nasal interfacing elements 116 or 118). The nasal interfacing element to which the line or conduit from the medicament delivery port 410 is in fluid connection or communication is the inspiratory nasal interfacing element or its associated conduit. In this manner, medicament delivered via the port 410 is directed to a flow of gases being directed for delivery to the user or patient.

In another embodiment, the line or conduit extending from the port 410 may provide for a selective fluid connection or communication with each the nasal interfacing elements (e.g. one of nasal interfacing elements 116 or 118 can be selected for delivery of a medicament). The nasal interfacing element to which the line or conduit from the medicament delivery port 410 is in fluid connection or communication is the inspiratory nasal interfacing element or its associated conduit. In this manner, medicament delivered via the port 410 can de selectively directed to a flow of gases being directed for delivery to the user or patient.

According to the above embodiment, such a valve or diverter valve or selector which allows for the matching or fluid coupling of a line or conduit connected to the port with a nasal interfacing element selected as the inspiratory line or conduit, for delivery of a medicament via the port to the user or patient, may be a manually adjustable valve or may be automatically adjusted according to a selection of the associated line or conduit which is to supply the source of gases to the associated line or conduit and a nasal interfacing element as a the inspiratory line or conduit and inspiratory nasal interfacing element. That is, the ability to select which of a nasal interfacing element or its associated conduit or line to receive a delivery of a medicament can be made manually or may be made in automatically in response to the selection of the diverter valve.

FIG. 14 illustrates a further system 1000, for example in which the indicative interface 200 is utilised, similar to the arrangement of FIG. 11. Shown is interface 200 on a patient, which receives an inspiratory flow of gases G via an inspiratory conduit 60, and a flow of the expiratory gases is directed from the interface via an expiratory conduit 40 to a bubbler device 70. A diverter valve 9 is provided for allowing the configuration of selectively determining the conduit and nasal interfacing component which is to be provided as the inspiratory line or conduit or the expiratory line or conduit. A humidifier system 30 is provided, which provides for a chamber sitting atop a heater base, the chamber of which is fed with a source of gases flow from, for example, a hospital or other supply source 2000.

In each of the interfaces 100 or 200 described above, it will be appreciated that one or more of the following may be provided:

- a bridge valve type arrangement can be provided for adjusting the bias flow,
- a diverter valve can be provided for allowing the switching of the nasal interface component being used in an inspiratory configuration or an expiratory configuration,
- different retention systems for retaining the interfaces on the patient may be used,
- systems for retaining feeding tubes may be provided in combination with the interfaces,
- nasal interfacing components are to be provided with nare sealing capabilities, or may be provided without nare sealing or non-sealing capabilities.

Further, in each of the embodiments of interfaces 100 and 200 described above, the inspiratory and expiratory gases conduits would extend downwardly from the forehead toward the nose. The conduits would connect directly to the prongs or may connect to the prongs through a manifold.

The manifold may include a partition between the inspiratory nasal interfacing component and the expiratory nasal interfacing component such that all inspiratory gases (i.e. fresh gases) are delivered through one such component (e.g. a nasal prong) and all exhaled gases from the user are directed through the expiratory component (e.g. expiratory nasal prong) and to an expiratory gases conduit. The nasal interfacing components may be nasal prongs and may include sealing structures such as a bulbous end or a pillow or cascaded/nested barbs to promote sealing with each nostril. The prongs may alternatively be in the form of inflating prongs that can inflate to seal about the nostril.

In another embodiment, a system comprising a medical breathing circuit can incorporate as a gases therapy delivery apparatus the patient interface 1 as described above. Such a system is to be provided with a source of gases G. The source of gases may be conditioned, such as being optionally heated and/or humidified.

Humidification may take place in a humidification chamber provided upstream of an inspiratory line or conduit. For example, may be a chamber configured to contain or retain a humidification fluid (e.g. water), the chamber comprising a heated base which is configured to transmit heat to the humidification fluid. The source of gases flow G can be transmitted into the chamber, be conditioned and then be transmitted further to the inspiratory line or conduit of the patient interface or system as described herein. Heating of the source of gases G may be provided by the humidification chamber or may in addition be provided by a controllably heated conduit provided as part of the patient interface 1 or as part of the system operable with the patient interface 1.

The conditioned gases can then be provided to a user via a gases transport pathway. The gases transport pathway can be connectable to an associated conduit (e.g. associated conduit 3 as shown in the configuration of FIG. 1) provided as a part of an inspiratory line or conduit for providing inspiratory gases to the user.

The system is configurable to allow for the selective connection of the source of gases G to an associated first or second conduit 3, 5 which are provided in fluid communication with their respective nasal interface components 2, 4. This means that either of the nasal interfacing components 2, 4 may be selected for delivery of the inspiratory gases. FIG. 1 shows the nasal interfacing component 2 in use as the inspiratory line or conduit gases pathway, while nasal interfacing component 4 is the expiratory line or conduit gases pathway.

The selective connection may facilitate the switching of the supply of the source gases G from one of the associated first or second conduit 3, 5, thereby enabling the switching of a nasal interfacing component that, in use, is to operate as the provider of inspiratory gases to the user. The selective connection would also allow the facilitation of the switching of the associated first or second conduit 3, 5 (and the nasal interfacing component connected to it) between operation as an inspiratory line or conduit or an expiratory line or conduit.

FIG. 1 shows an example patient interface in which the nasal interfacing component 2 and its associated conduit 3 is operating as a part of an inspiratory line or conduit, while the expiratory line or conduit is provided by the nasal interfacing component 4 and its associated conduit 5. G indicates the gases flow provided from a source (optionally having been conditioned) is provided to the user interface. The arrows in FIG. 1 indicate the flow direction of the gases through the associated conduit and nasal interfacing components when the patient interface 1 is configured without any fluid communication between the flow paths of the pair of nasal interfacing components. Compare this for example to FIG. 2 in which a bridge valve 6 is provided in the bridge region of the interface, providing for the capability to provide for a fluid communication between each of the nasal interfacing components.

Figure 2:
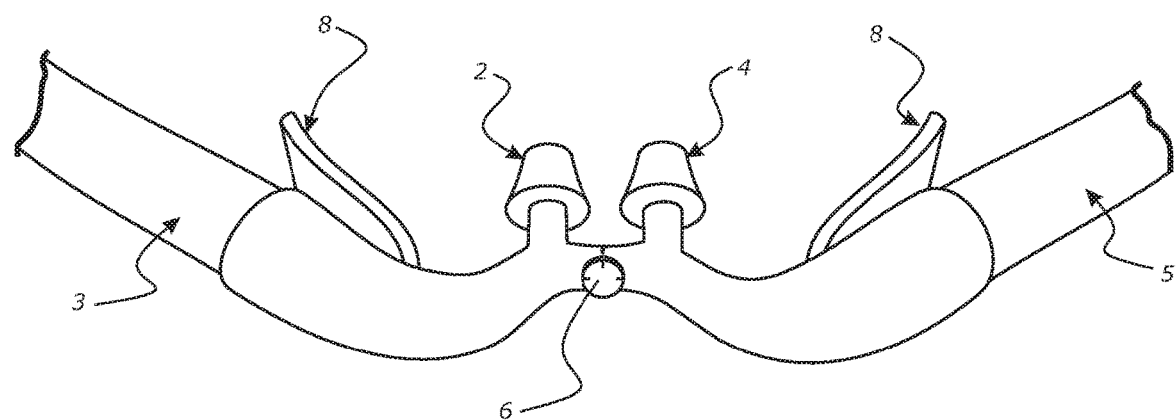
FIG. 2 illustrates an alternative embodiment of a patient interface.
Figure 3:
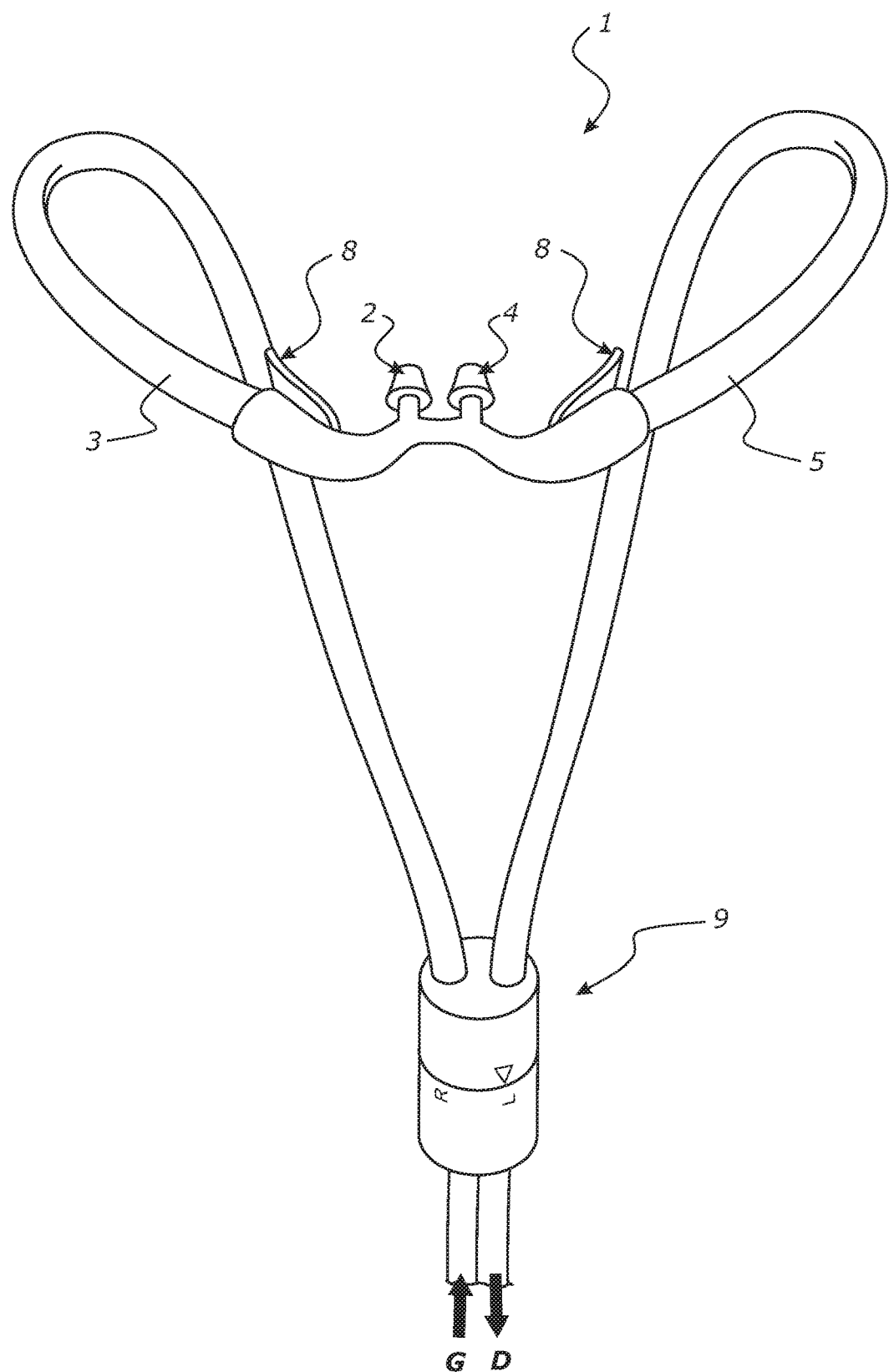
FIG. 3 illustrates an embodiment of a patient interface when provided in connection with a divert valve, and corresponding additional conduit in fluid communication with a source of gases and a downstream device.

FIGS. 1-3 also illustrate component parts of the interface 1 which may operate with a suitable retention system. For example, a pair of laterally extending wings 8 may be provided for implementation of a two-part releasable connection arrangement or securement system as described elsewhere in this specification.

In another embodiment, a method of providing a gases therapy to a user comprises delivering a gases from a source to a user via a sole inspiratory line or conduit and receiving a gases from a user via a sole expiratory line or conduit, wherein a first nasal interfacing component (configurable for engagement with the user's first nare) is operable to be provided for the delivery of inspiratory gases to the user, and a second nasal interfacing component (configurable for engagement with the user's second nare) is operable to be provided for receiving an expiratory gases from the user. In such a method of providing a gases therapy, the gases therapy can be a positive airway pressure type (PAP) therapy.

The apparatus, system and method as described above facilitates for the delivery of a gases to a user in which the delivered gases (i.e. the inspiratory gases from an inspiratory line or conduit) provides for a dedicated point of delivery to a user's airway (e.g. via a single nare), rather than allowing a delivered gases to pass through an interface from an inlet to the interface to an outlet of the interface, and avoiding the provision of that delivered gases reaching the user. Such a configuration may assist in reduction of dead space in the patient interface itself, and may provide for the provision of a detection system to determine if there may have been a loss of gases therapy being provided to the user.

The first nasal interface component may be of any suitable arrangement, shape or size, yet is configured for providing an interface with full or partial insertion with or into the user's first nare. Similarly, the second nasal interface component may be of any suitable arrangement, shape or size, yet is configured for providing an interface with full or partial insertion with or into the user's second nare.

One, or both, of the first and second nasal interface components 2, 4 can be or is/are configured for substantially sealingly engaging or interfacing with the user's nare to which each nasal interfacing component is to be provided. For example, a first nasal interfacing component can be provided for a sealing engagement with a user's first nare, while the second nasal interfacing component can be provided for a sealing engagement with a user's second nare.

In FIGS. 1-3, the nasal interfacing components are shown as nasal prongs of a nasal cannula, the prongs having a wider portion lower down the neck of the prongs, to facilitate for a substantial sealing of the prongs with the user's nares.

In this manner, the substantial sealing of the nasal interfacing components (first and second) with the nares of the user (first and second) can provide for a patient interface, system or method of providing a gases therapy to the user, which can be controlled.

For example, a substantial seal with the user's nares can be achieved, which in turn allows for the provision of particular gases therapies to the user, for example CPAP (e.g. bubble CPAP device), BiPAP, NiPPV, SiPAP (e.g. a flow driver providing for CPAP), for the controlled provision of a gases to a user. Controlled delivery of gases to a user may utilise a device associated with an expiratory line or conduit for controlling the flow of gases a user can provide to the expiratory line or conduit of such a patient interface, system comprising the patient interface or a method of providing gases therapy to the user.

There are a variety of mechanisms or systems which may be employed for providing a nasal interfacing component with a nare sealing capability. For example, a sealing member may be provided as a part of each nasal interfacing component. Such a sealing member may take the form of a seal or an arrangement which one in place with a user's nare may be operable to substantially provide for a seal (e.g. nasal pillows or other inflatable-type arrangements) or the nasal interfacing component may be suitably shaped to, once substantially inserted into a user's nare, provide for a seal with a user's nare wall.

It will however be appreciated that other seals or sealing member arrangements can be provided for a nasal interfacing component. This may take the form of a physical shape or form or arrangement of a plug-type seal system, or may take the form of an arrangement which can be operated to, in-use, provide for a seal with a user's nare (e.g. inflatable-type pillow system).

Where the nasal interfacing component is, for example, a nasal prong, for example of a nasal cannula type patient interface, then the nasal prong would have a seal or sealing member. Alternatively, where the nasal interfacing component is, for example, a part of a nasal mask type patient interface, then the portions for engagement with each of the user's nares would be provided with suitable seals or sealing member.

In yet a further alternative, other forms of nasal interfacing patient interfaces may be provided comprising of a partition to provide for a separation between a user's first nare (e.g. a left nostril/nare) and the user's second nare (e.g. a right nare), the partition facilitating the controlled delivery of the source of gases as an inspiratory gases flow to one of the user's nares and facilitating the controlled receipt of gases as an expiratory gases flow from the other of the user's nares. For example, see the patient interfaces (and associated systems) as illustrated by FIGS. 8-14. In this respect, the nasal interfacing structures 116 and 118 may be large enough to form a seal with the nares. Alternatively the structures 116, 118 may include other sealing structures as defined herein.

The patient interface can create a sealed gases pathway between a gases source and a first nare and a sealed gases pathway from the second nare to a further component.

Similarly, providing a patient interface that facilitates sealing of an inspiratory line or conduit with a first of a user's nares and a sealing of an expiratory line or conduit with a second of a user's nares can make the interface suitable for CPAP and other related pressure-controlled gases therapies.

While the nasal interfacing components are referred to as comprising of a seal, a sealing capability may be sufficiently adequate that approximately a 90% (of the cross-section) of a user's nare is occluded by the nasal interfacing component.

Further examples include nasal prongs of any shape that can seal each nare individually, e.g., inflating prongs, Christmas-tree shaped barbs, a plurality of cascaded barbs, a trapezoid pillow on a stalk type arrangement, or a dual wall pillow on a stalk type arrangement, or even high flow therapy prongs. Other type of patient interfaces can be modified to seal each nare individually, e.g., dual-chamber nasal pillows. It will be appreciated the nasal interfacing components may be large enough to form a seal with the nostrils. Alternatively the structures may include other sealing structures as defined herein.

In various embodiments, the patient interface can be configured to comprise of a partition 7 (e.g. may be a mechanical/physical partition) between each of the first and second nasal interfacing components.

The partition 7 may, for example, be a solid bridge region when in a nasal cannula type patient interface. For example, as shown in FIG. 1.

Such a partition provides for a mechanical fluid disconnection between a fluid flow path of the first nasal interfacing component and a fluid flow path of the second nasal interfacing component. In this manner, the fluid flow paths of each nasal interfacing components can be kept separate and/or remain as dedicated to either an inspiratory operation or an expiratory operation.

In an alternative configuration, the partition 7 may be configured to provide for an adjustable or controllable mechanical fluid connection and/or disconnection of fluid flow paths of the first and second nasal interfacing components. For example, the partition may comprise of, or be, a valve such as that indicated by item 6 in FIG. 2. The valve 6 can be any suitable arrangement which allows for the control gases flow between the fluid flow paths of the nasal interfacing components. Gate valves, butterfly valves or other valves suitably configured can be used. Such a controllable or adjustable partition allows for an adjustment of a bias flow of the source of gases to said first and/or said second nasal interface components (depending on which is selected or provided as the inspiratory side and which is selected or provided as the expiratory side of the patient interface).

Providing a partition 7 or a division between inspiratory and expiratory flow paths can provided for a number of end-user as well as gases therapy-related advantages, for example including but not limited to:

Allowing the gases flow to be unidirectional, so gases flowing into one side of the patient interface must flow through the user's airway (e.g. into the user's airway via an inspiratory line or conduit) to get to the other side of the interface (e.g. out of the user's airway via an expiratory line or conduit).

A valve in the bridge portion (i.e. a bridge valve, such as 6 in FIG. 2) may be optionally provided between the pair of nasal interfacing components (e.g. between a first nasal prong and a second nasal prong)—such a bridge valve may allow the patient interface to be switched between different modes, for example a unidirectional flow (e.g. a single dedicated/sole inspiratory nasal interfacing component, and toward a more traditional CPAP flow by opening the bridge valve and allowing some of the inspiratory line or conduit gases flow to reach the other of the nasal interfacing components, for example the nasal interfacing component that was, in the prior mode, being used operationally as a single dedicated/sole expiratory nasal interfacing component).

In various embodiments, a diverter valve 9 can be implemented to fluidly connect the source of gases flow G to one of: the first conduit 3 and the first nasal interface component 2, or the second conduit 5 and the second nasal interface component 4, to provide for an inspiratory line or conduit. Similarly, the diverter valve 9 when implemented can fluidly connect gases received from one of the first or second nasal interface components 2, 4 via an associated first or second conduit 3, 5 to provide for an expiratory line or conduit. The expiratory line or conduit may deliver expiratory gases flow to a device D (not shown) capable of controlling the expiratory gases so as to provide assistive control of a gases therapy being provided to the user.

For example, the device may be a bubble CPAP type arrangement providing for a back-pressure to the gases in the closed-system being provided to the user. Alternatively, or in addition, the diverter valve 9 can connect with or provide for the return of expiratory gases to a port of a gases source.

In an alternative embodiment, a diverter valve 9 may be implemented to operably divert the source of gases to one of the first conduit and the first nasal interface component (3, 2) or the second conduit and the second nasal interface component (5, 4), thereby configuring the patient interface 1, system or method of providing gases therapy to the user, by determining the nasal interfacing component to be used for the inspiratory line or conduit. Similarly, the diverter valve 9 when implemented may be operable to fluidly connect a received gases from a user via one of the first nasal interface component and the first conduit (2, 3) or the second nasal interface component and the second conduit (4, 5) (when provided as an expiratory line or conduit). The expiratory line or conduit may be provided in fluid communication with a device D (not shown) capable of controlling the expiratory gases so as to provide assistive control of a gases therapy being provided to the user, for example the device may be a bubble CPAP type arrangement providing for a back-pressure to the gases in the closed-system being provided to the user.

Where a diverter valve 9 is provided as part of a patient interface 1 (e.g. an assembly) or a system or as part of a method for providing a gases therapy to a user, such a diverter valve 9 can facilitate the selective determination or directing of the source of gases to either one of the first conduit and the first nasal interface component or the second conduit and the second nasal interface component, to operate as an inspiratory line or conduit, and for selectively allowing the other one of the first conduit and the first nasal interface component or the second conduit and the second nasal interface component, to operate as an expiratory line or conduit.

In the manner described above, the diverter valve 9 can controlled or adjusted to selectively determine:

either the first conduit or the second conduit as the inspiratory line or conduit for delivery of a source of gases to either the first nasal interface component or the second nasal interface component, and either the first conduit or the second conduit as the expiratory line or conduit for subsequent receipt of gases from either the first nasal interface component or the second nasal interface component.

For example, such a diverter valve 9 can be manually adjusted (e.g. by a medical personnel), or can be automatically adjusted or controlled based on inputs, such as user or patient parameter inputs or based on an intended variation of the nare to be provided with an inspiratory gases (and consequently also the nare to be used for the expiratory flow).

Accordingly, the adjustment or control of the diverter valve 9 may be operated to be synchronised with a user's nasal cycle (a user's natural alternation of increased or reduced congestion between each of the user's nares), or to provide relief to the user by switching or alternating the nares being used to receiving the inspiratory flow and the expiratory flow.

Advantageously, the diverter valve 9 fluidly connects the expiratory line or conduit with a downstream device D (not shown). For example, downstream devices may be those, including but not limited to, CPAP bubblers or other device creating a back-pressure of the gases in the expiratory line or conduit.

A diverter valve 9 can fluidly connect the associated conduits (operable as inspiratory and expiratory line or conduits) to either of the nasal interfacing components prongs, depending on the position of the diverter valve. In particular, a switch or other actuation mechanism can be moved, for example, between two settings (e.g., "R" and "L" to indicate that the inspiratory flow is directed to either the left or the right prong, respectively).

Figure 4:
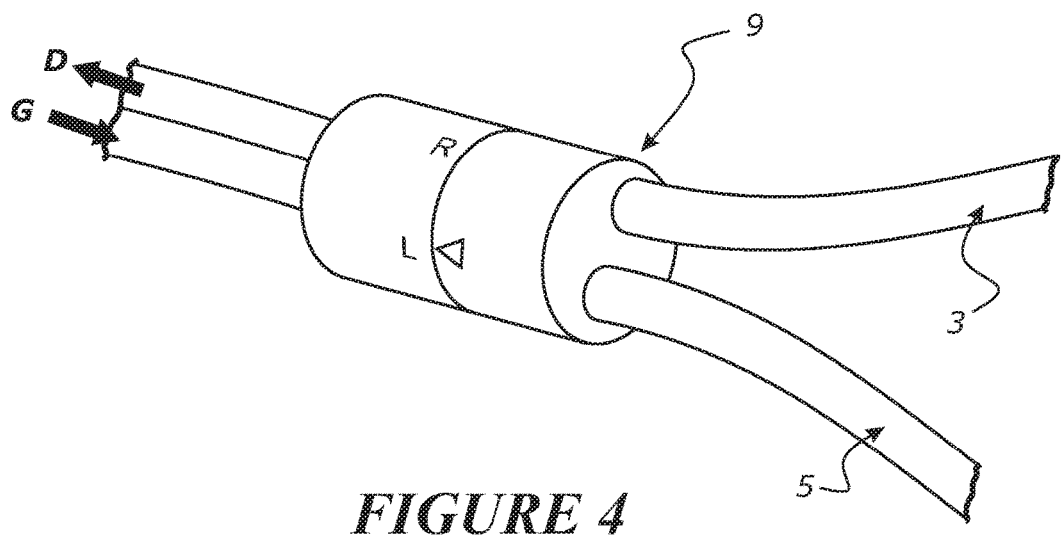
FIG. 4 illustrates a close-up view of a diverter valve.
Figure 5:
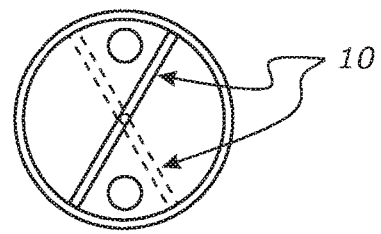
FIG. 5 is a cross-section through the diverter valve of FIG. 4 illustrating how a vane of such a valve can be re-oriented to switch the associated conduit beings supplied with a gases from a gases source G, and to switch the associated conduit being provided in fluid communication with a downstream device D.
Figure 6:
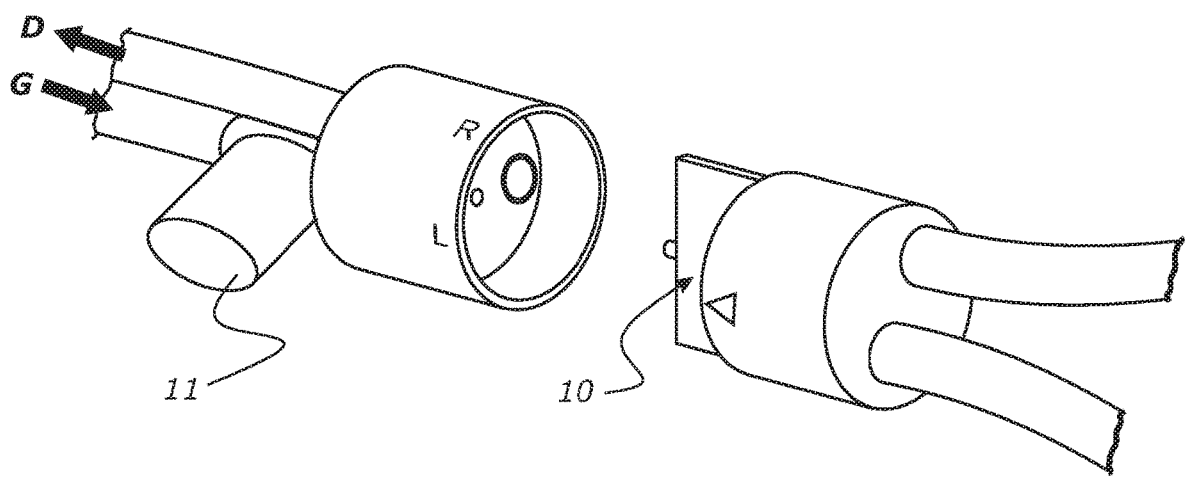
FIG. 6 is the diverter valve of FIG. 4 in a disassembled state showing how a vane is operable with the housing or body of a divert valve.

For example, FIG. 3 illustrates a diverter valve 9 configured in which the conduit to receive the inspiratory gases flow is selected as "L". FIG. 4 is the same arrangement. FIGS. 5 and 6 illustrate the diverter valve 9 in one form when disassembled, showing an internal vane 10 which separates orients the gases flow from a gases source G to be directed to the associated conduit to be used as an inspiratory line or conduit, as at the same time, segregates the other of the associate conduit to be used as an expiratory line or conduit and for directing the expiratory gases to a downstream device D (not shown). FIG. 5 is a cross-section through the diverter valve 9 showing how the vane 10 may be re-oriented inside the housing of the diverter valve in accordance with switching the associated conduit to be used as an inspiratory and expiratory line or conduits. Additionally, one of skill in the art would appreciate that any suitable diverter valve which is known in the art could be used in place of the pictured diverter valve.

FIG. 6 also illustrates the optional additional implementation of a pressure relief device 11 provided on the gases source line or conduit. Such a pressure relief device can be provided as a user safety mechanism to prevent an overpressurisation of the user's airways.

A manually actuated diverter valve 9 is for example shown by FIGS. 3-6.

An automatic variant of a divert valve 9 can be actuated using a solenoid or similar component; such a diverter valve could still be actuated manually (e.g., when a caregiver pushes a user interface button) or could be automatically actuated based on time or pressure.

The diverter valve 9 can be utilised for synchronizing with the user's nasal cycle, to prevent asymmetric development of non-ossified airways in neonates, or simply to increase user comfort.

According to the various embodiments described herein, the patient interface, system and method may additionally incorporate a detector of a pressure or a flow of gases in the expiratory line or conduit. Such a detection can be used as an indicator of a leak or a loss of gases therapy being provided to the user.

The detector may be a sensor, such as a pressure sensor or a flow sensor provided on the expiratory line or conduit (or on the inspiratory line or conduit, or on both the expiratory and inspiratory line or conduits). Such a sensor or sensors can provide a signal responsive to a pressure or flow of gases in either or both of the expiratory or inspiratory line or conduits. Optionally, the gas in the expiratory line or conduit may be sent to one or more of: a capnograph, an oxygen sensor or analyser, a nitrogen or nitrous oxide sensor or detector, or a gas sample from the expiratory line or conduit may be sent to one or more of these sensing or detecting or analysing devices through a separate sampling line or conduit fluidly connected to the expiratory line or conduit.

Optionally, the expiratory line or conduit may include sensors for sensing, detecting or analysing one or more of:

humidity, temperature, pressure, flow, or a sample of gas from the expiratory line or conduit may be sent or directed to one or more of these sensors.

The detector and detection or signal generated from a sensor can be used to correlate with or be provided as an indicator of a leak or a loss of gases therapy being provided to the user. For example, when the gases flow or the gases pressure is above or below a threshold gases flow or threshold gases pressure (depending on whether the measured/sensed/detected flow or pressure is of the inspiratory or expiratory line or conduit), the gas flow or pressure detected or sensed or signal representative of these conditions can provide an indication of a leak or loss of gases therapy being provided to the user.

The detector may be provided where one or both of the first conduit and second conduit is/are non-self-supporting or is/are collapsible in the absence of a minimum gases pressure within these conduits or when the gases pressure within these conduit is below a pre-determined threshold value, such as the conduit of an expiratory line or conduit. For example, if the gases pressure were below a threshold gases pressure, the conduit may collapse—providing for a visual or observable indicator of a lack of pressure in the expiratory line or conduit. Such an indicator or detection can provide a medical personnel to note a change in the gases therapy being provided to the user. Checks can then be performed or adjustments made to re-establish provision of gases therapy to the user. For example, a seal provided by one or both of the nasal interfacing components may have become dislodged or the seal broken with the user's nares—in this way, an adjustment of the patient interface may allow a re-sealing and the intended gases therapy can be provided to the user. Alternatively, a change in gases flow or pressure parameters may be needed to re-establish gases therapy provision to the user. Alternatively, a device in the patient interface or system may have failed or become blocked and may need maintenance or replacement.

The conduit in fluid communication with the expiratory line or conduit, or the first conduit or the second conduit when provided as, or as part of, the expiratory line or conduit, may comprise of a detector or an indicator as described above.

The detector or an indicator may be provided that is capable of changing colour to provide, for example but not limited to, a visual indicator of one or more of the following characteristics or qualities of an expiratory gases: carbon dioxide, temperature, humidity, pressure.

In one example, an inflatable balloon or diaphragm can be fluidly coupled to the expiratory line or conduit (or the inspiratory line or conduit, or both the expiratory and inspiratory line or conduits), with the relative inflation of the balloon or diaphragm providing for an indicator or indication of gases therapy being provided to the user.

In another example, a pressure sensor (such as a pressure gauge) can be fluidly coupled to the expiratory line or conduit (or in an alternative to the inspiratory line or conduit) to provide a signal or indicator of the pressure provided to a user or a user's airway or of the gases in the expiratory line or conduit (or in the alternative, to the inspiratory line or conduit; or to both the expiratory line or conduit and the inspiratory line or conduits).

The indicator can provide for a visual indication or indicator of the pressure in the expiratory line or conduit (or the inspiratory line or conduit, or both of these line or conduits).

The detector or sensor as described above may generate a signal as one or more of the following: a visual output, an audible output, an alarm if a sensed pressure is above or below a threshold pressure value, an alarm if a sensed flow is above or below a threshold flow value.

With for example the unidirectional gases flow of the patient interface as described herein, such a design can help to eliminate a bias flow through the interface. For example, the patient interface may reduce or eliminate bias flow or a bulk bias flow that flows through the interface and out of the interface without entering the nares. As such, a user must be attached and receiving a gases therapy for a positive gases flow to be present in the expiratory line or conduit. Accordingly, a pressure or flow detector provided in the expiratory part of a medical breathing circuit can provide for a leak detection capability.

Digital pressure gauge with display or analogue pressure gauge with needle may be used for indicating a pressure. An absence of bubbles in a bubble CPAP chamber may also be used as an indicator or detection of a loss of therapy.

Further, depending on implementation, the detection mechanism for loss of therapy could also provide breath detection, i.e., measurement of respiratory rate. This could be implemented by, for example, a digital (or analogue) $CO_2$ gauge or a colour changing material triggered by $CO_2$.

According to various embodiments, a first sensor comprising of a pressure sensor can be associated with the inspiratory line or conduit and a second sensor comprising of a pressure sensor can be associated with the expiratory line or conduit. The sensed pressures of each line or conduit can be used individually or compared. For example, a difference in pressure between gases in the inspiratory line or conduit and gases in the expiratory line or conduit can be determined/measured—a signal or output of this detection or sensing can be provided (e.g. alarms or warnings or other information provided in visual, audible, or haptic forms).

Traditional breathing circuits for pressure-related therapies such as CPAP often include a relatively small (in internal diameter) pressure measurement tube that can be fluidly connected to one of the breathing circuit components (e.g., the inspiratory tube, the expiratory tube in a dual limb system, the wye-piece or other interface connector, the interface tube, or the interface itself). Such a measurement tube will generally have a small enough internal diameter, compared to the breathing circuit component to which it is fluidly connected, to create a high enough RTF (resistance to flow) to minimize the gases flow that escapes through the measurement tube instead of continuing through the breathing circuit component.

The patient interface, system and method as disclosed herein can utilise a similar pressure measurement tube fluidly connected to both prongs (i.e., in a wye shape), again with a high enough RTF to minimize gases flow that escapes through the measurement tube. However, the internal diameter can be selected to minimize not only gases flow into the main branch of the measurement tube (A) but also from one nasal interfacing component to the other nasal interfacing component (B), because gases flow from one prong to the other through the tube would decrease the effects induced by the unidirectional flow design as described herein. Pressure measurement of both prongs at once, effectively averaging the inspiratory and expiratory pressures, is useful as a good estimate of the naso-pharyngeal pressure inside the patient. A traditional pressure measurement tube that is fluidly connected to an inspiratory or expiratory circuit component can only measure the inspiratory or expiratory pressure, respectively, which is not necessarily a good estimate of the naso-pharyngeal pressure. Such a setup is for example shown in FIG. 7.

Figure 7:
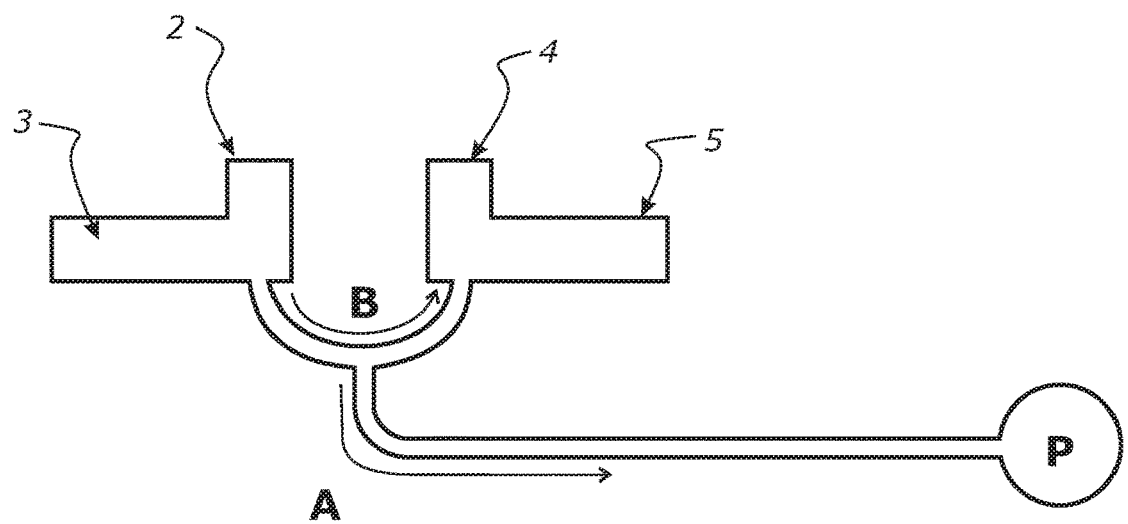
FIG. 7 illustrates a pressure measurement arrangement.

In FIG. 7, the nasal interfacing component identified as item 2 is provided as the inspiratory line or conduit, while the nasal interfacing component identified as item 4 is provided as the expiratory line or conduit.

Advantageously, the ability to measure or determine a patient pressure, without the need to position or put a sensor inside the patient's airway provides a unique development.

For example, a pressure port could be distant or located some distance away from the patient, such as at the connector to the breathing circuit, so long as the interface is either symmetrical or has a known asymmetry.

If the interface is symmetrical or substantially, then the measured pressure is provided as a useful approximation of the patient pressure.

Alternatively, if the interface has a predictable, known or predetermined asymmetry, then the measured pressure plus or minus an offset to account for the asymmetry will result in another useful approximation of the patient pressure. The specific amount of the offset may be dependent on, for example, the geometry of the interface and is calculable by one of skill in the art using known methodology.

Further, the same pressure measurement objective could be accomplished at or with a valve as shown and discussed with reference to FIG. 2. For example, the valve could be significantly, nearly or substantially closed such that an insubstantial volume of the bulk gas flow moves between the nasal interfacing components through the valve, so long as the valve still receives or gets some pressure input from both nasal interfacing components. The valve may comprise of a pressure sensor or a take-off or a port for a pressure sensor, or a port or take-off for connection with a pressure line or conduit to be provided in communication with a pressure sensor, then the pressure measurement taken at the valve, or at the pressure port or take-off of the valve, may be used as a useful approximation of the patient's naso-pharyngeal pressure.

Patient pressure may also be determined in systems or breathing circuits without an expiratory limb or a second nasal interfacing component (i.e. a user's second nare or second side of interface is open to atmosphere) by averaging the measured pressure in the inspiratory line or conduit or anywhere along in the inspiratory side of the gas flow with atmospheric pressure (either by using a pre-set value, or by measuring atmospheric pressure each time).

The discussion provided above in relation to pressure measurement calculations or determinations does not have to occur solely in a sealed system or breathing circuit with a patient interface which engages sealingly with a user's nares or airway, so long as the flow rate is high enough.

The patient interface described here can comprise of a retention system for retaining the interface upon a user's face. In this manner, the interface can be deployed and when worn in the appropriate manner, the intended gases therapy can be provided. Retention systems may improve the ability to provide the intended gases therapy to the user, and may also provide for user comfort features or used features that medical personnel can utilise without fuss (e.g. for allowing the ease of application of the interface to the user or readjustments as necessary).

In this manner, in one particular embodiment, the retention system provided for the interface can be an associated two-part releasable connection arrangement, such that the interface is positionable upon the user's face and yet can be removed and re-positioned as needed.

For example, a first part of the two-part releasable connection arrangement can be a dermal patch to be located upon a user's face, and a second part of the two-part releasable connection arrangement can be an interface patch to be located on a user-facing side of the patient interface. The interface patch can be connected or attached to a user-facing side of the interface, with the user-facing side of the interface patch itself comprising of a part of the two-part releasable connection arrangement which is releasably connectable or attachable to an interface-facing side of the dermal patch, the interface-facing side of the dermal patch comprising the other of the two-part releasable connection arrangement and being receivable of the user-facing side of the interface patch. Accordingly, the two patches (dermal and interface) can be brought together to be releasably fastened or connected together, yet which can be separated from each other to allow for the adjustment or re-positioning as may be desirable (e.g. either from a user comfort perspective or for better or improved or alternative provision of the gases therapy to the user via the patient interface).

One such suitable two-part releasable connection arrangement is that known as the Wigglepad™ securement system as manufactured by Fisher & Paykel Healthcare Limited.

Two such suitable patient interfaces which may be modified to comprising of a sealing system for the nasal interfacing components (e.g. nasal prongs of a nasal cannula), may for example be those known as the Optiflow Junior™ or Optiflow Junior 2™ nasal cannula interfaces.

With respect to the retention system described above relating to a two-part releasable connection arrangement or attachment mechanism, such a retention system may for example be the securement system as described in PCT/NZ2011/000218 (WO2012/053910) or by PCT/NZ2016/050041 (WO2016/148585).

With respect to the patient interface described above, such a patient interface as for example described in PCT/NZ2011/000218 (WO2012/053910), the contents of which are herein incorporated by reference, may be utilised but modified to optionally provide for nasal interfacing components (e.g. nasal prongs) comprising of sealing capabilities. In addition, in another embodiment, such a nasal cannula as described with reference to the document incorporated by reference above, may be modified according to the partition as described herein for control of the fluid communication between the gases flow paths of a first nasal prong and a second nasal prong. Still further, alternatively, such a nasal cannula as described with reference to the document incorporated by reference above, a diverter valve may be provided to selectively determine or control the conduit and a nasal prong which is to receive a source of gases as an inspiratory flow and to selectively determined or control the conduit and a nasal prong which is to receive a gases from the user as an expiratory flow.

In yet further alternative embodiments, the retention system may be a headgear. It will be appreciated a variety of forms of headgear may be provided depending on the form of the patient interface (e.g. whether as a nasal cannula type interface, or other nasal mask type interface). Where headgear is to be used, there may be a variety of form factors or other capabilities, including size adjustment, retention force, user comfort type features provided.

In further alternative embodiments, the patient interface or interfaces, as described herein, may be used with a two-part retention system that may comprise an integrated naso-gastric (NG) tube or oro-gastric (OG) tube or other feeding tube clutching or carrying or accommodating structure or structures. For example, a portion or a piece of the retention system may comprise one or more grooves or cut-outs to accommodate a feeding tube or NG tube or OG tube. In another embodiment, a portion of the retention system may comprise a flap or a foldable section or an extension that can be wrapped about the tube and removably connected back to a portion of the retention system to clutch the feeding tube in an operable position and reduce or minimize chances of dislodging the feeding tube from an in-use or operational position. Likewise, the same two-part retention system or same arrangement or types of structures may also be used to secure medication or medicament tubes, such as a surfactant delivery tube or other medicament delivery tube for connection with a take-off or port of an inspiratory line or conduit or other port for administering or delivering a medicament into the flow of gases being supplied or delivered to a user.

Figure 15A:
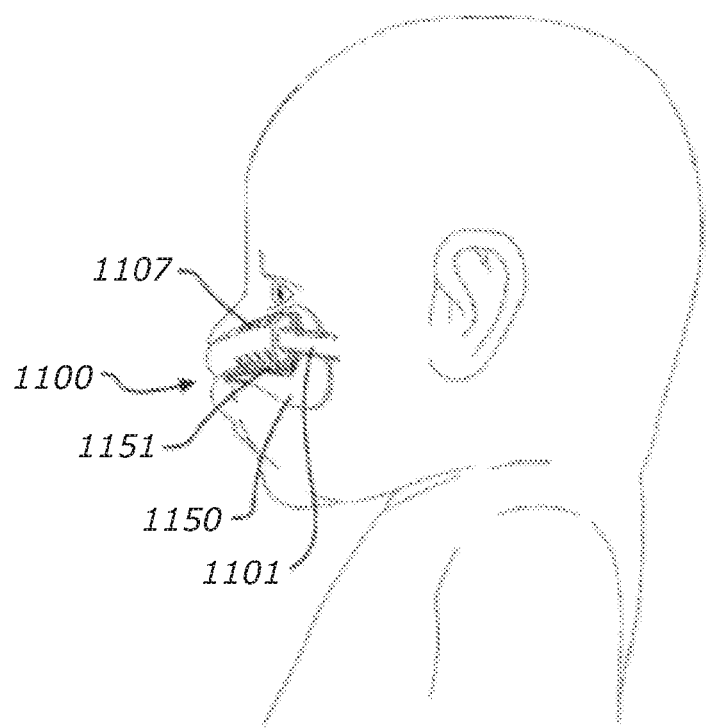
FIGS. 15A-15D illustrate an embodiment of an attachment mechanism for securing a user interface and/or user interface tubing to a patient.

An example of the two-part releasable connection system or attachment mechanism of Applicant's PCT/NZ2017/050109 is hereby reproduced as FIGS. 15A-15D. The two-part releasable connection system or attachment mechanism can be configured for securing a user interface and/or user interface tubing (or conduit or line) to a patient as illustrated in FIG. 15A. The attachment mechanism 1100 is illustrated supporting a nasal cannula on a patient or user face, but can also be adapted to support an adaptor for modifying of a patient or user interface for receipt of a medicament delivery tube or conduit or line using the same principles, for example such as by including an extension portion attachable to a patch instead of by way of clips.

In some embodiments, the attachment mechanism provides for a generally more rapid and improved or simplified ease of installation of a user interface into an operational position on a user. Further, these benefits may also contribute to improved or simplified ease of application of alternative user interfaces or removal of a user interface from a user when cycling a user between different therapies (such as gas treatments, e.g. CPAP or high-flow applications). In various embodiments provided by the two-part releasable connection system or an attachment mechanism, such an attachment mechanism or system may provide for quick location of an interface to a user, and may provide for the secured positioning of the interface.

In some embodiments, the ease with which a user interface may be positioned for a user is particularly useful. Providing a system whereby a carer (e.g. nurse) is able to apply the securement system with a single hand, for example where the interface user is an infant, can be particularly advantageous.

Figure 15B:
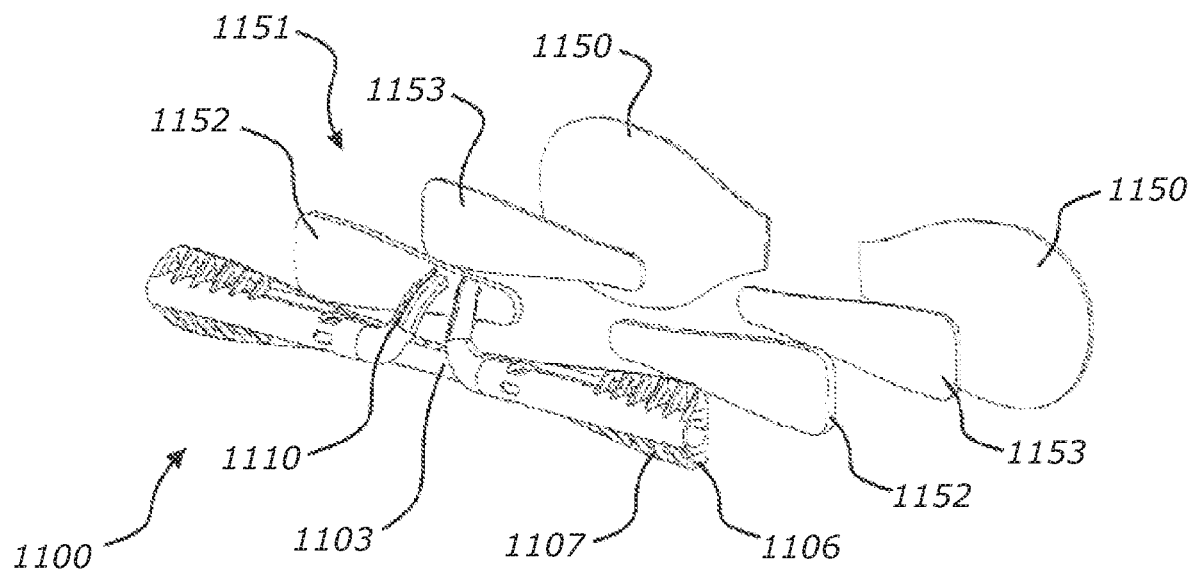

In addition, in another embodiment, the attachment mechanism provides for a first level of securement of a user interface to a user. For example, such a first level of securement may be that as shown by FIGS. 15A-15B. Where a user requires additional or heightened security of user interface positioning or securement, a secondary level of interface securement can be utilized. Such an additional level may include application of an over patch, such as that provided, for example, by patch 1260 illustrated in FIG. 15D Such a patch 1260 may be an adhesive patch and can be installed over the top of the user interface and/or tubing and adhered to a portion of the dermal patch 1150 (FIG. 15B).

The attachment mechanism 1100 comprises a two-part releasable attachment or connection arrangement 1151. The releasable connection arrangement 1151 acts between a pair of patches that are affixed to the patient and the user interface respectively.

The first patch can be a dermal patch 1150 that is adhered or otherwise attached to the patient's skin. The dermal patch can have a user side that faces the user's skin and an interface side that faces the user interface. The user side of the dermal patch 1150 may be attached to the skin of a user by a dermatologically sensitive adhesive, such as a hydrocolloid. The user interface side of the dermal patch can be provided with the first part 1153 of the two-part releasable attachment or connection system 1151.

The second patch can be a user interface patch 1152. The user interface patch 1152 can also have a patient side and an interface side. The patient side of the user interface patch 1152 can be disposed adjacent the dermal patch when the attachment mechanism 1100 is engaged. The complimentary second part of the two-part releasable attachment or connection system 1153 can be affixed to the patient side of the user interface patch 1152, so that the respective parts of the two-part releasable attachment or connection system 1151 are easily engageable when the patches 1150, 1152 are brought together. The interface side of the user interface patch 1152 can be affixed to the user interface. The user interface patch may be integrated with or suitably adhered to the user interface.

In some examples, a part or corner of the user interface patch 1152 may include a region that does not attach to the dermal patch 1150. The general purpose of this can be to allow a region (or tab) that can be more easily gripped by a user or carer for removing or detaching the interface from the dermal patch.

The two-part releasable attachment or connection arrangement 1151 may comprise a hook and loop material (such as Velcro™), a magnet or an array of magnets disposed on the respective patches with the poles suitably arranged, an adhesive arrangement that is activated when the patches are urged together or another suitable releasable suitable coupling. The interface side of the dermal patch 1150 may have one of a hook or a loop material, and the patient side of the user interface patch 1152 may have the other of the hook or loop material, such that the dermal and user interface patches are releasably attachable or connectable to each other.

When a hook and loop material is referenced, a hook and loop material can mean any one of a wide variety of area type mechanical fasteners. For example, the Velcro™ product range can include hook and loop product where the hook component includes upstanding nylon hooks (formed as cut loops through a woven backing web) which engage with any complimentary loop pile material. The Velcro™ range can also include extruded hook products, typically of a smaller size and which mate with "fluffy" non-woven fibre backing materials. These hook materials are designed to work with a range of loop substrates and in some cases, these hook materials act as loop substrates as well. Other similar systems include the Dual-Lock™ reclosable fastener system from 3M of St Paul, Minn. USA. The common feature of these releasable fastening systems is that they engage at any part of the contact between the two parts of the system. Precise alignment of individual connectors is not required because a multitude of connectors are distributed across the area of the product. A wide range of releasable fastener systems within this field may be used in the releasable attachment mechanism for providing releasable attachment between the dermal patch and the user interface.

The first part of the two-part releasable attachment or connection system may be adhered to the user interface side of the dermal patch with a suitable adhesive and occupy up to 100% or less than about 90%, or about 85%, or about 75%, or about 60% or about 50% or about 40% or about 30% or about 20% or about 10% of the interface side surface area of the dermal patch. In some embodiments, the dermal patch 1150 is a generally planar pad having a thickness much less than both its width and its length. In some embodiments, the pad has an overall oval shape, but may take other shapes.

The pad can also include a first part 1153 of the two-part releasable attachment mechanism 1151. In some embodiments, the construction of the dermal patch is such that the first part 553 of the releasable attachment mechanism comprises a substrate and multitude of fastener elements (with effective hooks, effective loops or other elements) provided across the area of the substrate. The substrate is secured to the body of the dermal patch. In some embodiments, the substrate is secured by adhesive or by direct bonding during forming of the dermal patch.

In some embodiments, the substrate can be smaller in area than the dermal patch and is located on the dermal patch so that it does not reach any edge of the dermal patch. In this way, the edge of the substrate can be spread from the edge of the dermal patch all around the perimeter of the substrate.

In some embodiments, the substrate for the first part of the two-part releasable attachment system can be flexible such that the plane of the substrate may bend to follow a surface that is curved in one direction. However, the substrate is typically not also stretchable to be able to follow a surface curved in two orthogonal directions. However, the pad is of the dermal patch may be stretchable and conformable to surfaces curved in more than one direction such as may be required to conform to the contours of the location of placement on the patient. According to some embodiments, this difficulty is alleviated by providing a first part 1153 of the two-part releasable mechanism in a form wherein the portion of substrate is divided by at least one slit or at least one slot into regions such that that different parts of the substrate portion may bend independently and thus the overall form of the substrate portion may deform to substantially match a surface curved in two directions. This will be the case even though the substrate portion is only curved in one direction at any individual location on the substrate portion.

Figure 15C:
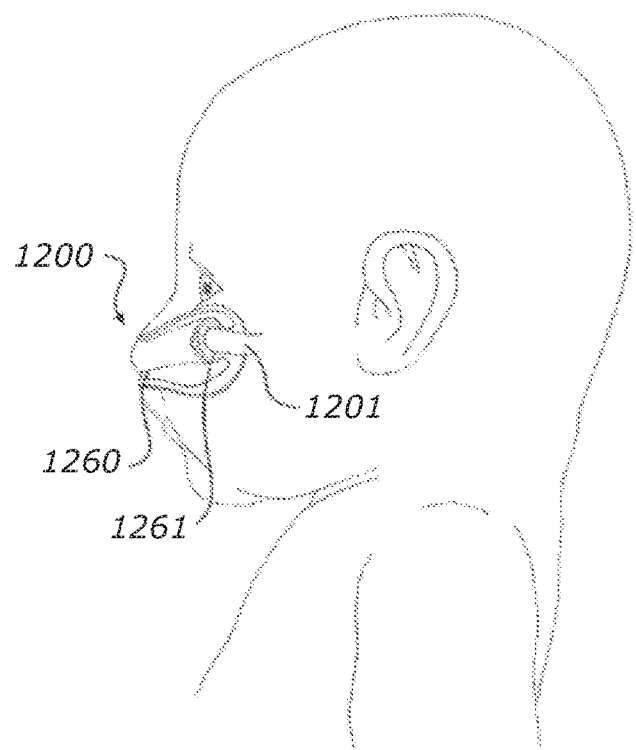
Figure 15D:
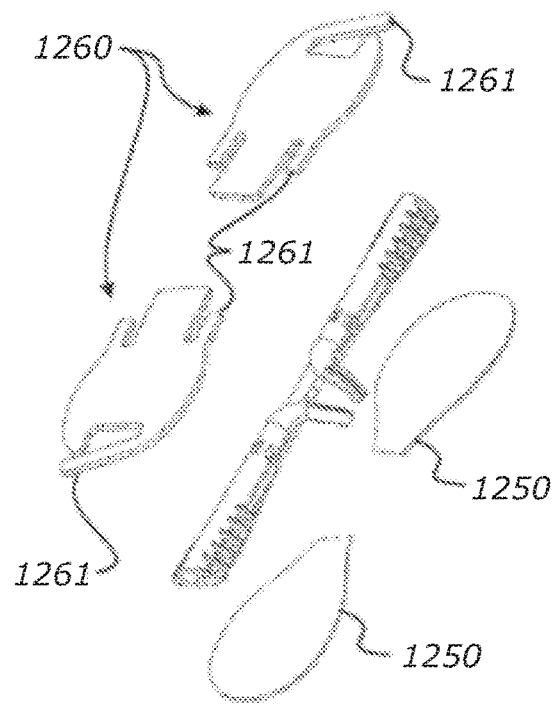

Another embodiment of the attachment mechanism is illustrated in FIGS. 15C-15D. The attachment mechanism 1200 can comprise a dermal patch 1250 and a securing patch 1260. The securing patch 1260 can extend over the user interface and/or tubing and adheres to the dermal patch 1250 to secure the interface and/or tubing to the patient. The dermal patch 1250 can define a securement footprint that is attached to the patient and has a similar configuration to the corresponding dermal patch 1150 in the above described attachment mechanism and two-part releasable connection system. The user side of the dermal patch 1250 is configured to attach or adhere to the user's skin.

The securing patch 1260 can extend over the user interface and/or associated user interface tubing and affixes to the dermal patch 1250 to secure the user interface to the patient. The securing patch 1260 and the dermal patch 1250 can be configured so that the securing patch can be contained within or bounded by the securement footprint of the dermal patch when the securement system is applied to a patient with a suitable or compatible user interface. Containing the securing patch 1260 within the dermal patch 1250 securement footprint can reduce the likelihood of unnecessary contact with the patient's skin and the potential for irritation. Ideally, the dermal patch 1250 can have the same or a greater surface area than the securing patch 1260. The dermal patch 1250 may include one part of a two-part mechanical fastener system across its surface or parts of its surface, with the securing patch 1260 having the other part of the fastening system.

In this manner, the dermal patch can be sized to reduce the likelihood of the taping or any additional taping to extend onto the skin of the user. Avoiding or minimizing the application, or repeated application and removal, of adhesives to a user's skin is preferred. This embodiment beneficially reduces the likelihood of repeated application of adhesive, or adhesive tape, to a user's skin for the installation and placement of a user interface into an operational position. Adhesive tapes or other dermal adhesive patches (when repeatedly applied and remove), particularly for example for infants, create problems. Problems include, but are not limited to, skin irritation from adhesive chemicals (or adhesive removal chemicals, such as solvents) or tape materials (e.g. due to skin sensitivities), damage to user skin due to repeated application and removal of dermal patches or tapes for positioning or re-positioning of the interface for the user. Re-positioning may be required or adjustments may be needed where treatment therapies are being cycled (i.e. changed from one type of treatment to another, and then back again). Advantageously therefore, the described embodiments provide for a system of positioning or locating of a user interface for a user, yet reducing the likelihood of the problems associated with adhesive tapes attached to the users skin.

It should be appreciated there are a number of disadvantages and problems associated with the re-positioning of an interface, particularly an infant interface. Included is "snub nosing", epidermal abrasion, or dermal allergies from traditional taping techniques for application of user interfaces (e.g. nasal cannula) to users. Such problems are also incurred during the cycling of a user between different treatment options and, traditionally, the subsequent removal of headgear or tapes or user interfaces and then the installation of new equipment and user interfaces or interface positioning headgear or other gear. Therefore, provision of a securement system which, when applied to a user, is in a ready-to-receive mode for receiving a user interface is a useful step in progressing toward reducing the problems users have previously been faced with. Further, improving the ease of installation, both in terms of complexity as well as time and effort by a carer (e.g. nurse), is of further benefit.

The securement patch may be shaped or otherwise configured to accommodate geometric or other features of the user interface and/or associated user interface tubing. The illustrated securement patches can have a plurality of wings 1261 that accommodate the user interface tubing and increase the contact surface of the securing patch 1260 exposed to the dermal patch 1250. The securing patches illustrated in FIG. 15D each have a pair of wings arranged at one end of the patch. The wings 1261 can be configured to secure to the dermal patch on either side of a user interface and/or associated user interface tubing and reduce the potential for the securing patch 1260 to bunch about the interface and/or tubing.

The securement patch 1261 illustrated in FIG. 15D can also have a tube end wing 1261. The tube end wing 1261 can be configured to extend under the user interface tubing and affix to the dermal patch 1250 to link the ends of the securing patch 1260.

The above described embodiments of the attachment mechanisms can be used to secure tubing to any part of a patient's body. The embodiments illustrated in FIGS. 15A-15D are configured to attach a user interface to a patient's face, in particular, adjacent the user's upper lip and/or cheek. The illustrated securing systems can be adapted for neonatal applications.

The user side of the dermal patches 1150, 1250 can have a dermatologically sensitive adhesive (such as a hydrocolloid) that adheres the patch to a user's skin, so that application of the respective securing systems causes as little irritation as possible. The dermal patches 1150, 1250 can have sufficient surface areas to distribute the adhesive and interface retention forces over an adequate area of the user's face to reduce localized pressure build up.

In some embodiments, a patient or user face can also be adapted to support an adaptor for modifying of a patient or user interface for receipt of a medicament delivery tube or conduit or line.

Such an adaptor or interface comprising of such an adaptor, can include a securement system for retaining, holding, or securing pressure and/or medicament delivery conduit (e.g. a surfactant delivery lumen) in position on a patient's face. In some embodiments, the pressure lumen is configured to be fluidly connected to the pressure tube and the medicament delivery conduit (e.g. a surfactant lumen) is configured to be fluidly connected to a medicament conduit (e.g. a surfactant tube). In some embodiments, the securement system comprises a two-part releasable attachment or connection arrangement. The releasable connection arrangement acts between a pair of components that are affixed to the patient and the pressure and/or surfactant tube respectively. Several such securement systems are described in PCT/NZ2013/000069 (WO2013/157960) the contents of which are hereby incorporated by reference.

Figure 16:
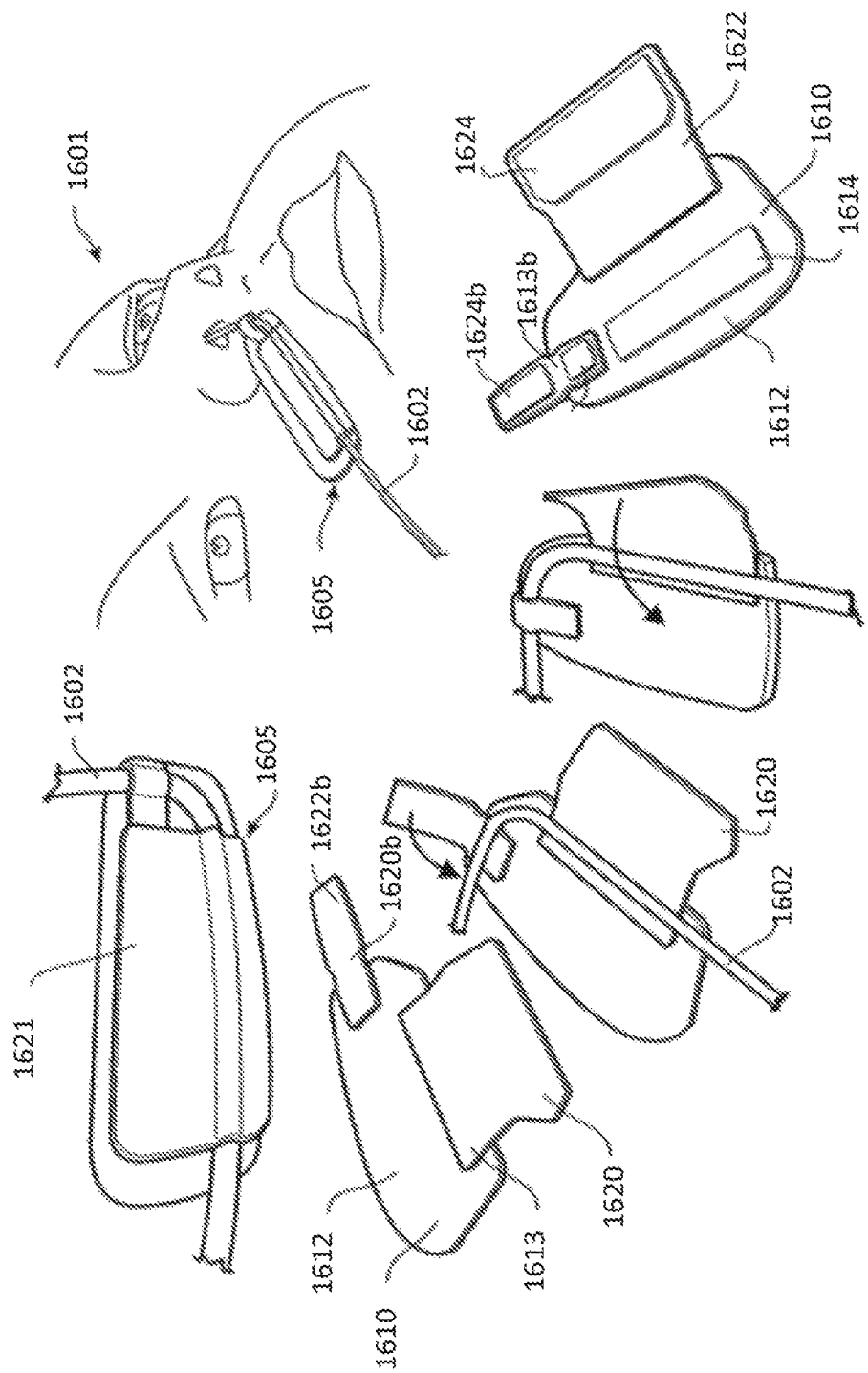
FIG. 16 illustrates an embodiment of a securement system comprising a two-part releasable attachment or connection arrangement.
Figure 17:
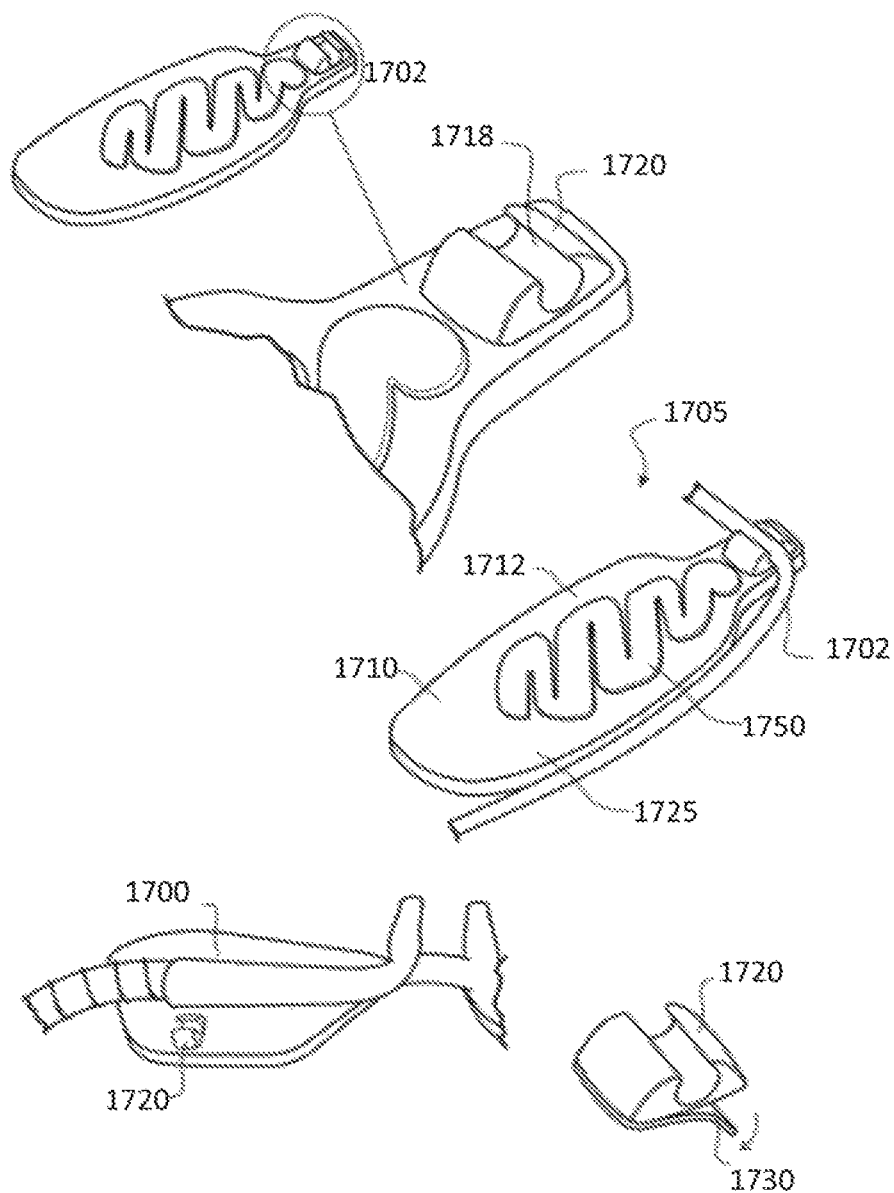
FIG. 17 illustrates another embodiment of the securement system comprising a two-part releasable attachment or connection arrangement.
Figure 18:
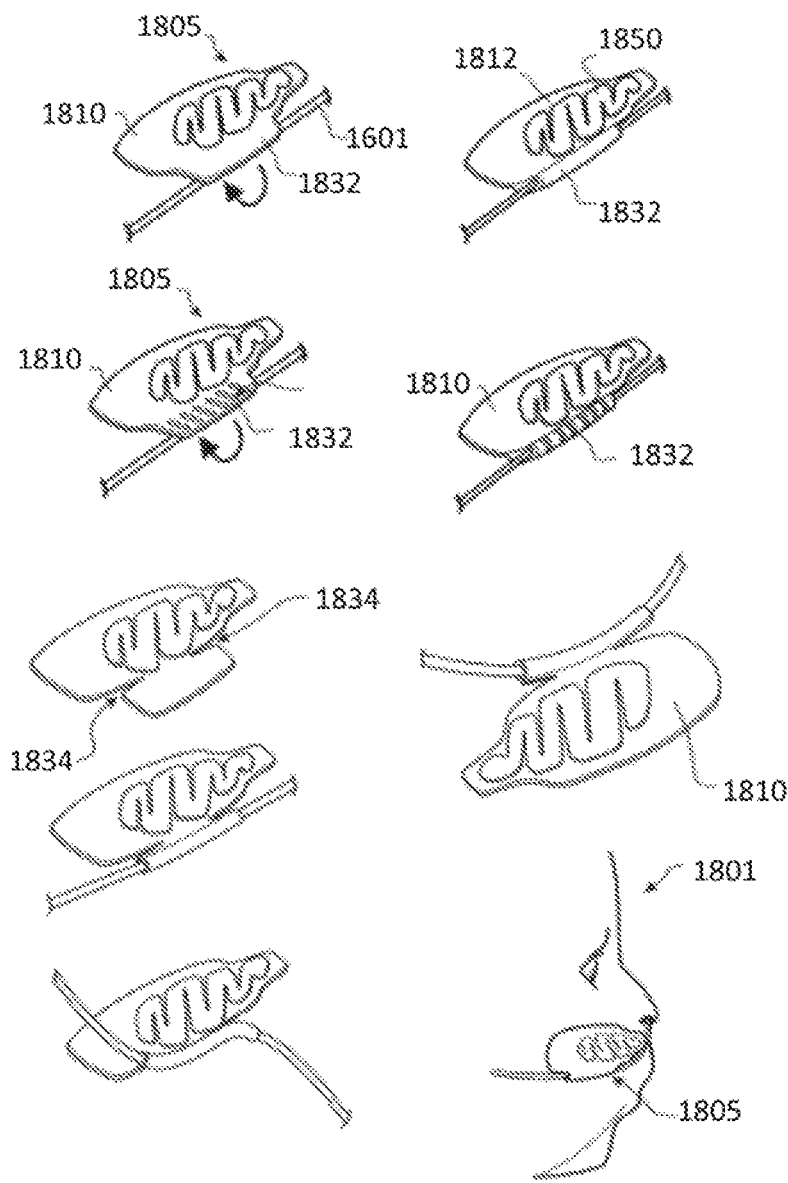
FIG. 18 illustrates another embodiment of the securement system comprising a two-part releasable attachment or connection arrangement.

An example of the attachment mechanism is hereby reproduced as FIGS. 16-18.

In reproduced FIGS. 16-18, the two-part releasable attachment mechanism can further include structures to retain the pressure and/or surfactant tube. In some embodiments, these structures can be holder, clips, flaps, etc.

For example, as illustrated in FIG. 16, the two-part releasable attachment mechanism can include a panel that is configured to be folded onto the dermal patch so as to retain the tube. The dermal patch 1610 and the panel 1620 are coupled together at an edge region 1613. To couple the first and second parts of the two-part releasable attachment system together, the panel is folded onto the dermal patch to bring the patient side 1622 of the panel adjacent to the interface side 1612 of the dermal patch to couple the first and second parts 1614, 1624 of the two-part connection system together to capture or sandwich the tube 1602 there between.

As another example, FIG. 17 illustrates the two-part releasable attachment mechanism further including a clip for securing a pressure and/or surfactant tube. The dermal patch 1710 for adhering to the skin of the patient can include a securement clip 1720 that is attached to or integrally formed with the dermal patch. The securement clip includes a recess or cavity or channel for receiving the tube 1702. The recess is open so that a section of the tube may be pushed in a lateral direction with respect to a longitudinal axis of the tube into the clip. An end of the tube need not be pushed through the clip for securement. The recess can have a lateral dimension similar to or slightly smaller than a diameter of the tube so that the tube is gripped firmly by the clip. In one embodiment, the clip is releasable from the dermal patch. For example, a two-part connection system as described previously may be applied between the clip and the dermal patch. Alternatively, the clip may be releasably attached to a patient interface 1700.

FIG. 18 illustrates the two-part releasable attachment mechanism having a wing portion that is configured to wrap about and secure the pressure and/or surfactant tube. The securement system 1805 can include a dermal patch 910 for attaching to the face of a patient. The dermal patch comprises a wing portion 932 for wrapping about the tube 2 once the tube has been correctly positioned in the patient's nostril.

Figure 19A:
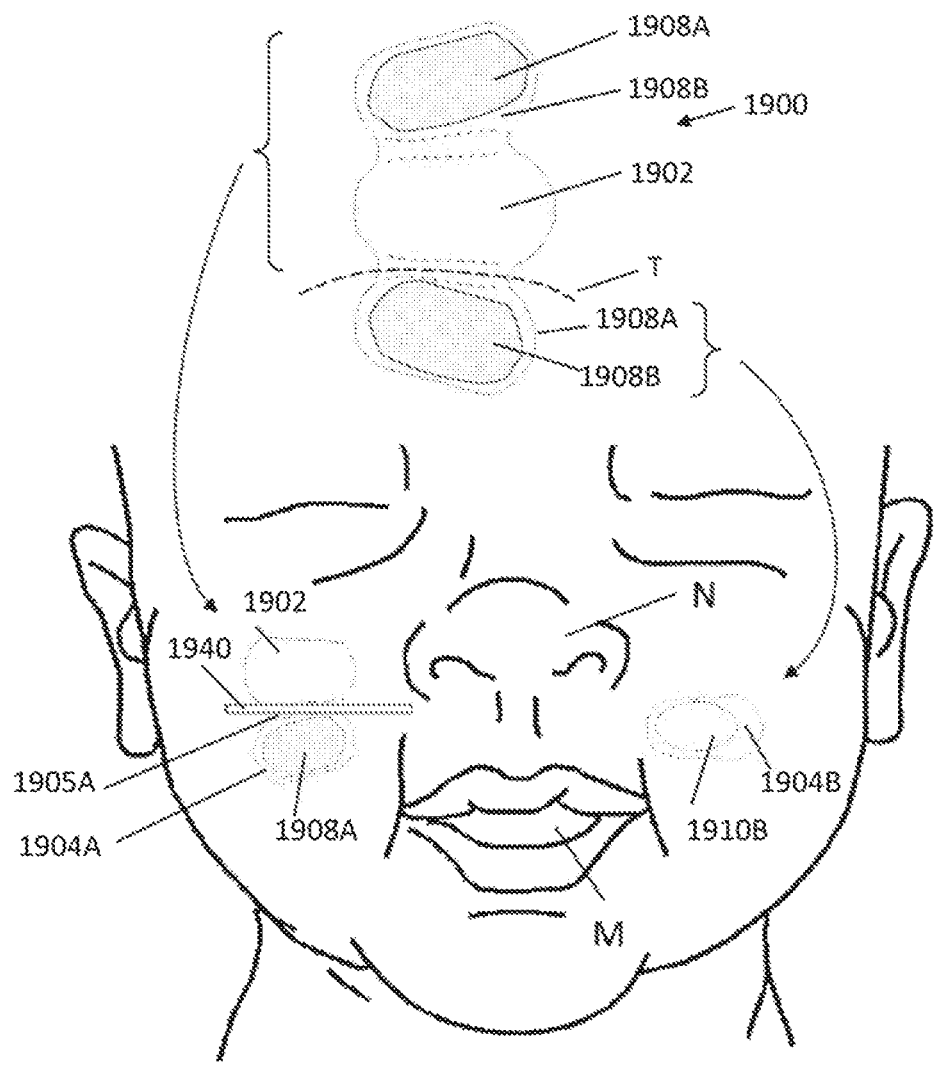
FIGS. 19A-19B illustrate an embodiment of a fixation structure configured to secure the pressure lumen and/or surfactant lumen to the face of the patient.
Figure 19B:
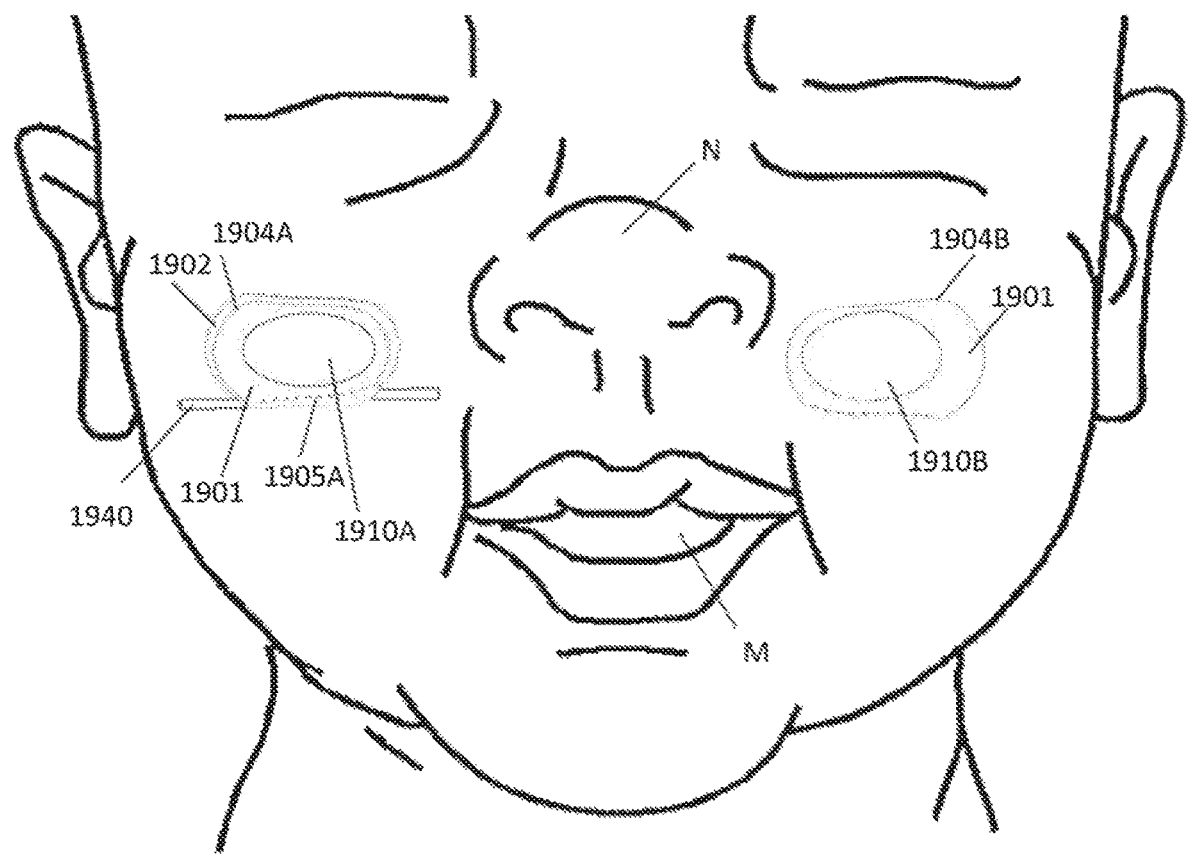

FIGS. 19A-19B illustrates an embodiment of a fixation structure that can be configured to secure the pressure and/or a medicament delivery tube or conduit or line, such as a surfactant tube. FIGS. 19A and 19B illustrate the fixation structure assembly having perforated sections that allow for the removal of the fixation structure from the tube to be secure.

A close-up of a face of a patient is shown, with a nose N and mouth M. The fixation structure assembly 1900 may be torn along tear line T, detaching one of the separable extensions 1904B. In the illustrated embodiment, a pair of perforated sections links the body 1902 with one of the separable extensions 1904A, 1904B. The body 1902 and the separable extension 1904A still attached to the body 1902 may be placed on one side of the face, and the detached separable extension 1904B may be adhered to the other side of the face via use of the adhesive portion 1908B, thus exposing the fixation element 1910B of the detached separable extension 1904B. The tube 1940 can be placed over the body 1902, and the separable extension 1904A attached to the body 1902 can be folded to cover the tube 1940.

As shown in FIGS. 19A-19B, the tube 1940 can be positioned in the perforated area (for example, the first intermediate region 1905 A) or adjacent the perforated area. This can facilitate quick and simple removal of the fixation structure assembly 1900 from the tube 1940. As a result, the tube 1940 does not necessarily have to be removed as the fixation structure is removed, and a healthcare provider is then not required to reinsert the tube 1940 following removal of the fixation structure assembly 1900, reducing the number of steps required. Positioning the tube 1940 in or near the perforated area can aid in enabling the fixation structure assembly 1900 to be folded and/or to stick to itself. For example, this can aid in the separable extension 1904A being folded over the body 1902.

In some examples, the moulding part-line could also be down the central plane of symmetry of the adaptor (instead of splitting along the threaded connectors). In some examples, the threaded connectors can also be arranged with their axes parallel to the plane of symmetry but offset from the centre so as to create space between them. In some examples, this can allow for a more compact arrangement and simpler tooling, with less complex movements. This can also possibly include the pressure port facing longitudinally between them.

The illustrated securement systems are particularly configured to receive and/or secure a patient interface or an adaptor and any necessary tubing, such as medicament delivery tubing or nasogastric tubing. The tubing may extend from one or both side(s) of the user's face. In some embodiments, a patient interface and securement systems can include a dynamic interface to absorb the patient's facial movements. As dynamic interface may be utilised to dampen the effect of the baby's facial movements on the positioning of the patient interface about the patient's nose. An example of the dynamic interface is disclosed in PCT/NZ2014/000217 (WO2015/057083) the contents of which are hereby incorporated by reference.

An example of the attachment mechanism of PCT/NZ2014/000217 (WO2015/057083) is hereby reproduced as FIGS. 20A-20C, 21A-21C, and FIG. 22. In some embodiments, the dynamic interface can incorporate one or more hinges along the device that reacts to facial movements, both natural and forced, and external forces exerted on the interface. The hinges can minimise the effects of the facial movements and external forces on the fitment of the interface on the patient's face, particularly on the placement of the prongs in the patient's nares. As used herein, hinges refers generally to portions on the interface that are configured to bend in one or more directions. The hinges can be configured to bend in a predefined direction or directions, and in some embodiments the hinges can be restricted from bending in certain directions.

Figure 20A:
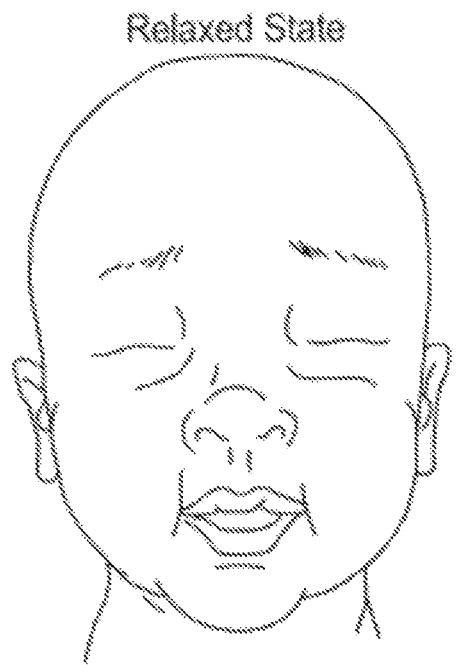
FIGS. 20A-20C illustrate an embodiment of an attachment mechanism comprising a dynamic interface.
Figure 20B:
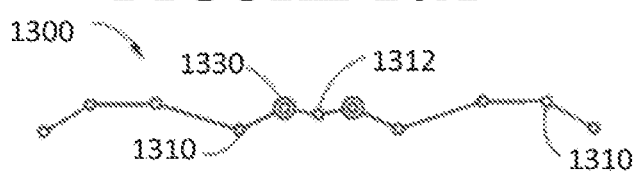
Figure 20C:

FIGS. 20A-20B illustrate an example of a relaxed facial shape of an infant and FIG. 20C illustrates a schematic of the geometric shape of a dynamic interface 1300 on a relaxed face. FIG. 20A is a front view of an infant's face and FIG. 20B is a bottom view of the infant's face. FIG. 20C is a bottom view of a dynamic interface. The dynamic interface 1300 can have one or more hinges 1310. Preferably, the dynamic interface has a centre hinge 1312 disposed between the prongs 1330. The plurality of hinges 1310 on the interface allows the interface 1300 to conform to the general contours of the patient's face.

Figure 21A:
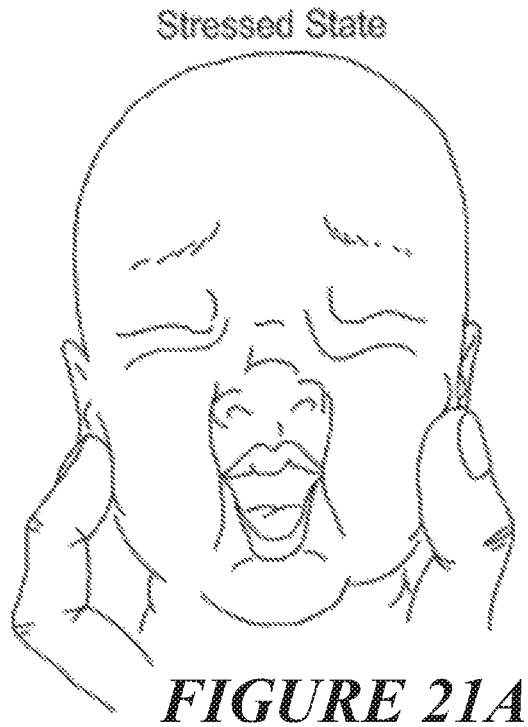
FIGS. 21A-21C illustrate another embodiment of the attachment mechanism comprising a dynamic interface.
Figure 21B:
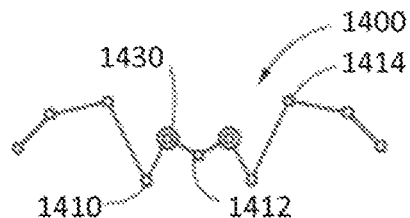
Figure 21C:

FIGS. 21A-B illustrates a front view and a bottom view, respectively, of an example of a stressed or squeezed facial shape of an infant. FIG. 21C illustrates a bottom view schematic of the geometric shape of a dynamic interface 1400 on a squeezed face. The squeezed face approximates, for example, the contortion of the face when patients lie on the side of their faces. As illustrated in FIG. 21C, the hinges 1410 help conform the interface 1400 to the shape of the contorted face and maintain the position of the prongs 1430 in the nares of the patient. The dynamic interface 1400 is particularly helpful in the case of infants or other patients who tend to exhibit exaggerated cheek movement. Prong flicking may be reduced.

Each hinge 1410 can be configured to react to an applied force in a predetermined fashion and different hinges can react differently depending on their position on the interface. For example, a hinge 1412 located in the region between the prongs 1430 may bend downward toward the lips and/or inward toward the face to form a concave shape when viewed from the front, while the hinges 1414 adjacent the cheeks of the patient may bend outward to form a convex shape around the cheeks. The hinge 1412 can resist movement outwards normal to the face and minimize the movement of the prongs 1430 out of the nares due to forces applied laterally on the device. In some situations, the bending of hinge 1412 can be limited by the patient's anatomy. For example, the inward bending of hinge 1412 can be limited by the philtrum of the patient, which can beneficially limit the displacement of the prongs 1430. The forces applied to the interface may act on the other hinges (e.g., hinges 1414 adjacent the cheeks) once the hinge 1412 reaches its limit. Combinations of hinge types and hinge locations can allow the designer to control how an interface will react in a variety of situations. A hinge may be designed to allow for 1, 2 or 3 degrees of motion in any predefined direction depending on its desired function. Advantageously, an inherently stable interface can be developed that keeps the prongs in the patients nares under various loading conditions.

Figure 22:
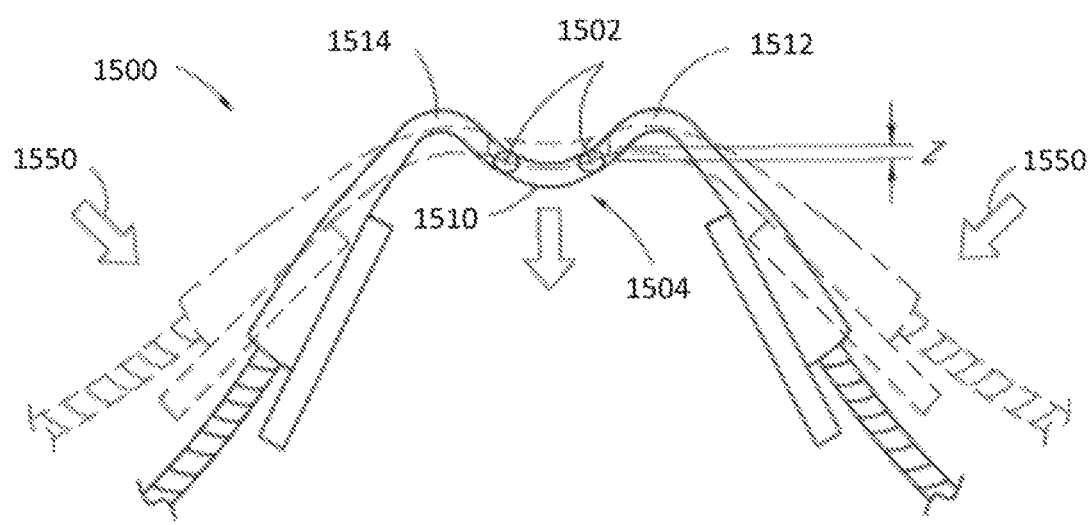
FIG. 22 illustrates another embodiment of the attachment mechanism comprising a dynamic interface.

Another example of a dynamic nasal interface 1500 is illustrated in FIG. 22. Although the pictured interface is a nasal cannula, the hinging portions could be adapted to support the disclosed adaptor of the present application using the same principles, such as by including a hinging extension portion attachable to a patch as discussed above.

For example, FIG. 22 illustrates a nasal interface 1500 having hinges in at least three locations, the bridge hinge 1510 and outer hinges 1512, 1514 on either sides of the prongs. The additional hinges of the nasal interface help stabilize the positions of the prongs 1502 when the cannula is under stress and reduce the displacement distance, helping to keep the prongs in the nares of the patient and reduce the irritation of the nares by the prongs. In some embodiments, the bridge hinge 1510 and outer hinges 1512, 1514 can be configured to be attachable to the aforementioned patch so as to support the disclosed adaptor.

Additional embodiments of dynamic interfaces are further illustrated in PCT/NZ2014/000217 (WO2015/057083) the contents of which are hereby incorporated by reference.

With respect to the various patient interfaces described herein, where for example the patient interface may be a nasal cannula type interface, the nasal cannula may be of the arrangement as described in PCT/NZ2011/000218 (WO2012/053910), or PCT/NZ2014/000217 (WO2015/057083), the contents of which are each herein incorporated by reference. In particular, the nasal cannula as described by these documents provides a nasal cannula system comprising of separated or independent gases flow paths, with the additionally provision of at least one element responsive to force(s) or movement(s), or both, experienced by at least a first region of the patient interface.

In this manner, compensation can be provided by the patient interface to movements translated to the interface by the user, which may otherwise comprise the provision of an intended gases therapy or dislocation of, for example, the nasal interfacing components (e.g. nasal prongs) from a user's nares. In particular for pressure-controlled gases therapies, such compensation can be helpful in minimising the likelihood of a loss of sealing connection of the nasal interfacing components from a user's nares—loss of the sealing would result in a loss of gases therapy being provided to the patient. Accordingly, a patient interface as described herein may be modified according to the functionalities and mechanical modes as set out in the above-referenced document. In particular, the functionalities and mechanisms of a nasal cannula interface referenced by the document above may be provided to a nasal cannula in the regions outside of a bridge region of such a nasal cannula.

According to the documents referenced above, the patient interface as described herein may be modified according to the references, but additionally provide for sealing capabilities of the nasal interfacing components (e.g. nasal prongs of a nasal cannula). In such embodiments, the associated conduit for each nasal interfacing component (e.g. the conduit or tube associated with each) may be of the reinforced type as described in those referenced documents.

With respect to the various patient interfaces described herein, such a patient interface may be modified or comprise those features as described by PCT/NZ2013/000069 (WO2013/157960) and PCT/NZ2016/050050 (WO2016/159783), the contents of which are each herein incorporated by reference. In particular, the contents of these documents provide for a variety of feeding tube retention systems or capabilities which may be integrated into a patient interface as described here, or as part of such a system as described herein.

Such retention systems find applicability to not only feeding tubes, but also other tubes or conduits or devices requiring securement in place. For example, a conduit or supply line or conduit for supplying or delivering a medicament to a take-off or port of an inspiratory conduit or on an inspiratory side of a patient interface may be retained in a position using the retention systems as described by the patent specifications above. For example, a medicament delivery conduit may be fluidly connected to take-off or port 410 as shown in FIGS. 12 and 13. Such a medicament may for example be a surfactant, which may be aerosolized for addition to the gas flow.

In further alternatives, a patient interface may be utilised having a take-off or port for connection with a medicament delivery conduit or line or conduit. Some form of an adapter may be provided or configured for connection with a take-off or port, to enable a medicament delivery conduit or supply line or conduit to be connected to the interface. It will be appreciated that the take-off or port may be in or on the patient interface itself, such as a nasal cannula or a wye piece, or as part of a conduit provided on an inspiratory side of the breathing circuit, for introducing a medicament, which could be an aerosolized medicament, such as surfactant or aerosolized surfactant, into the flow of gases being delivered to a user.

One particular advantage of medicament delivery through a unidirectional interface is the ability to direct all or substantially all of the medicament dose administered into the gas flow to the user. This is achieved through the provision of directing the entirety of an inspiratory flow into the user/patient. This provides for a significant advantage, and helps to solve a major problem of medicament delivery where a significant quantity, and sometimes all, of the medicament delivery is washed out of the interface without being delivered into the user/patient by the bias flow or the patient's expiratory flow impacting on that medicament delivery. If, for example, the gases delivery flow rate being supplied to a user/patient is about 8 L/min and the user/patient's peak inspiratory requirement is only about 500 mL/min, then there is a limited ability for uptake of the medicament by the user/patient and much of the medicament dose which was attempted to be delivered may instead end up passing through to the expiratory conduit or limb. Such a situation may result even if a clinician or medical assistant attempts to time the medication delivery or dose to match the timing of the user/patient's inspiration phase of their breathing cycle.

Accordingly, the ability to provide for a medicament delivery into an inspiratory side of a breathing circuit (e.g. an inspiratory conduit) or an inspiratory side of a patient interface (e.g. an upstream side of a first nasal interfacing component), provides for a simpler and more efficient mode of medicament delivery to a user/patient. Such an administration allows for a more efficacious medicament delivery system, without the complications of trying to match medicament delivery with a user/patient's inspiration phase.

The patient interface as described herein can be configured to receive or provide for the delivery of one or more medicaments to the nare of a user of the interface. For example, a medicament can be delivered to the inspiratory line or conduit or to a nasal interfacing component when provided as part of an inspiratory line or conduit. Medicament can be atomized or nebulized for delivery into the flow of gases in the inspiratory line or conduit or into the gases flow path of a nasal interfacing component (when operable as part of an inspiratory line or conduit). In this manner, a dedicated or sole inspiratory nasal interfacing component can provide for a direct delivery to the user.

With respect to medicament delivery, an adjustable or controllable partition between the nasal interfacing components may be configured to prevent for any fluid communication between the gases flow paths of these two interfacing components during the delivery of the medicament, and therefore unintended loss undelivered medicament to the user. Yet, in such an arrangement, the partition of the interface can be configured after the delivery back to a particular setting. For example, a particular setting for a patient may provide for a desired bias flow between the nasal interfacing components to fine tune the gases therapy being provided to that patient.

The medicament delivery can be utilised in combination with various gases therapies.

The following outlines various gases therapies which may be utilised in combination with the patient interface, system and method as described herein:

Bubble CPAP

The nasal interfacing component provided on the expiratory line or conduit can be provided in fluid communication with an associated conduit (e.g. an expiratory conduit) that leads to a bubbler (which regulates PEEP by forcing gases through water)—same as a traditional bubble CPAP device. The expiratory gases flow forces water down through a "dipstick" (the adjustable tube or pipette inside the bubbler), and then the gases escape to atmosphere as bubbles in the water contained in the bubbler chamber. The deeper the dipstick is below water level, the more pressure required of the gases to force the water through the dipstick.

In operation, if the chamber is bubbling, then there is an indication that the expiratory gases pressure must be at least X cm $H_2O$, where X is the depth in cm that the dipstick is below water level. The absence of bubbles can indicate loss of therapy.

The bubble chamber can also act as a pressure limiter, as once the chamber is bubbling pressure is being relieved, so it is difficult for the pressure to rise higher than the setting on the dipstick. This setting thus determines the PEEP in the patient.

Manual Ventilation/Resuscitation

The nasal interfacing component provided on the expiratory line or conduit can be provided in fluid communication with an associated conduit (e.g. an expiratory conduit) that leads to a PEEP (Positive end expiratory pressure) valve. The pressure (above atmospheric) remaining in the lungs at the end of exhalation Ventilator CPAP/BiPAP/(S)NiPPV The nasal interfacing component provided on the expiratory line or conduit can be provided in fluid communication with an associated conduit (e.g. an expiratory conduit) that leads back to a ventilator.

CPAP is a continuous positive airway pressure, provided for delivery of air at a relatively constant pressure to "splint" the upper airway of the user.

BiPAP is a bi-level positive airway pressure (similar to CPAP but with different pressure levels for inspiration and expiration).

(S)NiPPV—(Synchronized) nasal intermittent positive pressure ventilation, being of a therapy generally similar to CPAP but with the PIP intermittent and substantially synchronized to respiratory rate in order to provide "breaths" to the patient SiPAP (Synchronized Intermittent Positive Airway Pressure, Flow Driver Type CPAP)

The nasal interfacing component provided on the expiratory line or conduit can be provided in fluid communication with an associated vent, such a vent venting directly to atmosphere (for example through a filter).

According to the description herein, a system can be provided which comprises a gases source, a conduit provided as an inspiratory line or conduit, and a patient interface as described above.

The gases source may be a pressurized gases delivered source, such as via blower or ventilator.

The system can provided is a medical breathing circuit, where the circuit is a closed system or circuit, or where the circuit is an open system or circuit.

The system as described herein can provide a CPAP delivery system.

In another example, the system provided includes a component fluidly connected to, or in fluid communication with an expiratory line or conduit or an associated conduit of an expiratory line or conduit.

The expiratory line or conduit can be fluidly coupled to a downstream component or device configured to provide for a pre-determined or an adjustable back-pressure or a PEEP substantially at the opening of said nasal interfacing component provided as the expiratory line or conduit for the user.

As each nasal interfacing component comprises of a fluid pathway, the fluid pathway is connected or connectable at one end by an associated conduit which when selectively utilised (e.g. by adjustment of a diverter valve described above), an independent or dedicated fluid connection can be made by an opening of the nasal interfacing component connected thereto by the associated conduit (e.g. a first associated conduit is provided in fluid communication with a first nasal interfacing component).

According to the embodiments as described above, in a further alternative there may be provided a patient interface comprising a pair of nasal interfacing components, one of the pair configured for sole inspiratory gases delivery to one of a user's nares and the other of the pair configured for sole expiratory gases received from the other of the user's nares; and a valve operable to selectively control which one of the pair of nasal interfacing components is to provide the inspiratory gases to the user and which one of the pair of nasal interfacing components is to receive expiratory gases from the user. Such a patient interface may optionally comprise one or more of the embodiments or features as described above.

Further, according to the patient interface as described above: in a first mode, the valve can be operable to allow for inspiratory gases to be delivered to a first of a pair of nasal interfacing components and to allow for a second of the pair of nasal interfacing components to receive expiratory gases from the user; in a second mode, the valve can be operable to allow for inspiratory gases to be delivered to a second of a pair of nasal interfacing components and to allow for a first of the pair of nasal interfacing components to receive expiratory gases from the user.

According to the embodiments as described above, in a further alternative there may be provided a patient interface comprising a pair of nasal interfacing components, to be provided in fluid communication with the nares of a user; a bridge portion (optionally mechanically) joining the nasal interfacing components; wherein the bridge portion comprises a bridge valve configured to fluidly connect each of the pair of nasal interfacing components.

With respect to the above embodiment, each nasal interfacing component comprises of a gases pathway, at one end of the gases pathway is an opening for fluid communication with the nare of a user, and at the other end of the gases pathway is an associated conduit for extending the gases pathway.

Optionally, the bridge valve is operable to adjust or control a bias flow of gases being delivered to a user via the nasal interfacing components.

Optionally, a valve is operable to selectively control which one of the pair of nasal interfacing components is to provide the inspiratory gases to the user and which one of the pair of nasal interfacing components is to receive expiratory gases from the user. For example, such that: in a first mode, the valve allows inspiratory gases to be delivered to a first of a pair of nasal interfacing components and allows a second of the pair of nasal interfacing components to receive expiratory gases from the user; in a second mode, the valve allows inspiratory gases to be delivered to a second of the pair of nasal interfacing components and allows a first of the pair of nasal interfacing components to receive expiratory gases from the user.

According to the various nasal patient interfaces as described herein, one of the pair of nasal interfacing components is configurable for sole inspiratory gases delivery to one of a user's nares and the other of the pair is configurable for sole expiratory gases received from the other of the user's nares.

According to the embodiments as described above, in a further alternative there may be provided a patient interface comprising a first nasal interface component to provide a fluid connection with a user's first nare, an inspiratory gases pathway in fluid communication between the first nasal interface component and a gases source to provide inspiratory gases to the user's first nare, a second nasal interface component to provide a fluid connection with the user's second nare, and an expiratory gases pathway to receive expiratory gases from the user's second nare. In such a configuration, the inspiratory gases pathway is disconnected from fluid communication with the second nasal component.

According to the embodiments as described above, in a further alternative there may be provided a patient interface comprising a first nasal interface component to provide a substantially sealed fluid connection with a user's first nare, an inspiratory gases pathway in fluid communication between the first nasal interface component and a gases source to provide inspiratory gases to the user's first nare, a second nasal interface component to provide a substantially sealed fluid connection with the user's second nare, and an expiratory gases pathway to receive expiratory gases from the user's second nare, wherein the inspiratory gases pathway is not in fluid communication with the second nasal component.

According to the embodiments as described above, in a further alternative there may be provided a method of delivering a gases flow to a user through a patient interface as described herein, such that a dedicated inlet nasal interfacing component is provided for providing a dedicated inspiratory flow to one of a user's nares and communicating an exhaled or expiratory flow away via from the other of the user's nares via a dedicated outlet nasal interfacing component.

According to the embodiments as described above, in a further alternative there may be provided a method of delivering a unidirectional gases flow through a dedicated inlet nasal interfacing component and communicating an exhaled flow away via a dedicated outlet nasal interfacing structure, such that the gases flow turns or changes direction within a user's nasal passage(s).

According to the methods described above, both of the nasal interfacing components are configured for sealing with a user's nares.

Optionally, the unidirectional gases flow can be selectively directed to either a first nasal interfacing component or a second interfacing component, the nasal interfacing component selected becoming the dedicated inlet nasal interfacing component, and the other of the nasal interfacing components becoming the dedicated outlet nasal interfacing component.

Optionally, a flow diverter is operable to selectively divert the gases flow to either of the first nasal interfacing component or the second interfacing component.

Optionally, a partition or fluid path controller is operable to facilitate a fluid connection between each of the first nasal interfacing component and the second interfacing component. The partition or fluid path controller may be operable to control or adjust a bias flow of the gases flow being delivered to the nasal interfacing components.

According to the embodiments as described above, in a further alternative there may be provided a method of administering a gases therapy to a user comprising: delivering a first flow of gases to a first nasal interfacing component as an inspiratory flow, said first nasal interfacing component provided in fluid communication with a first of a user's nares; receiving a second flow of gases from a second nasal interfacing component as an expiratory flow, said second nasal interfacing component provided in fluid communication with a second of a user's nares; controlling the expiratory flow.

Optionally, the expiratory flow is controlled according to any one or more of the following gases parameters: pressure, flow rate.

Optionally, the expiratory flow is controlled to provide for an upstream parameter according to any one or more of: pressure, flow rate.

Optionally, the parameter to be controlled influences the gases pressure provided to or experienced by a user's airway.

Optionally, the gases therapy delivered to the user is a CPAP gases therapy.

Optionally, the expiratory flow (or optionally the inspiratory flow) is controlled by or directed to one or more of:

a bubbler or a bubble CPAP device or another pressure regulator, for regulation of the pressure provided to a user or experienced by a user's airway;

a ventilation or resuscitation device, such as for provision of any one or more of the following gases therapies for the user, including but not limited to, a continuous positive airway pressure (CPAP), BiPAP, NiPPV;

a flow generation device or flow driver, such as for provision of a desired gases therapy for the user, including but not limited to, a SiPAP.

The various embodiments described above may provide for a patient interface, a system or method which provides one or more of the following advantages:

Elimination of mechanical dead space in the patient interface

"Washing out" (reduction) of anatomical dead space in user's airway

More $CO_2$ flushing out of the patient's airway, reducing re-breathed $CO_2$

More accurate/predictable pressure delivery

All of the pressure produced by the gases source is delivered to the user—do not have to account for indeterminate pressure loss from bias flow through the interface.

The wye-shaped measurement tube may provide for an improvement in accuracy of estimating of naso-pharyngeal pressure compared to a traditional measurement tube that measures only one side Potential reduction in voluntary respiratory rate Potential reduction delivered oxygen percentage, when used with oxygen therapy More efficient delivery of nebulised medication Potential reduction in work of breathing of the user In respect of potential reduction in work of breathing by the user/patient, while it might be considered that the work of breathing would increase due to the user/patient having to breathe out from a single nare, the applicant has surprisingly found that the user/patient's work of breathing is not higher, it is lower, unless there are high bias flows.

Bias flow rates may be such as up to or greater than about 14 L/min, or up to about 15 L/min, or up to about 16 L/min, or up to about 17 L/min, or up to about 18 L/min, or up to about 19 L/min, or up to about 20 L/min, or up to about 21 L/min, or up to about 22 L/min, or up to about 23 L/min, or up to about 24 L/min, or up to about 25 L/min, or up to about 26 L/min, or up to about 27 L/min, or up to about 28 L/min, or up to about 29 L/min, or up to about 30 L/min, or up to about 31 L/min, or up to about 32 L/min, or up to about 33 L/min, or up to about 34 L/min, or up to about 35 L/min, or up to about 36 L/min, or up to about 37 L/min, or up to about 38 L/min, or up to about 39 L/min, or up to about 40 L/min, or up to about 41 L/min, or up to about 42 L/min, or up to about 43 L/min, or up to about 44 L/min, or up to about 45 L/min, or up to about 46 L/min, or up to about 47 L/min, or up to about 48 L/min, or up to about 49 L/min, or up to about 50 L/min, or about 14 L/min to about 50 L/min, or about 14 L/min to about 45 L/min, or about 14 L/min to about 40 L/min, or about 14 L/min to about 35 L/min or about 14 L/min to about 30 L/min, or about 14 L/min to about 25 L/min, or about 14 L/min to about 20 L/min, or less than about 50 L/min, or less than about 45 L/min, or less than about 40 L/min, or less than about 35 L/min, or less than about 30 L/min, or less than about 25 L/min, or less than about 20 L/min.

The foregoing description of the invention includes preferred forms thereof. Modifications may be made thereto without departing from the scope of the invention.

The invention claimed is:

1. A patient interface comprising:
   a first nasal interfacing component to be provided in fluid communication with a user's first nare, and an associated first conduit provided for an independent and/or dedicated fluid connection with the first nasal interfacing component;
   a second nasal interfacing component to be provided in fluid communication with a user's second nare, and an associated second conduit provided for an independent and/or dedicated fluid connection with the second nasal interfacing component;
   wherein one of either:
      the first nasal interfacing component with said associated first conduit, or
      the second nasal interfacing component with said associated second conduit is configured as a sole inspiratory line for delivery of a source of gases to one of the user's first or second nares, and
   wherein the other of the one of the first nasal interfacing component with said associated first conduit or the second nasal interfacing component with said associated second conduit, is configured as a sole expiratory line for receiving gases from the other one of the user's first or second nares, wherein both the first nasal interfacing component and the second nasal interfacing component are operable as either the sole inspiratory line or the sole expiratory line wherein the first nasal interface component is configured for substantially sealingly engaging or interfacing with the user's first nare, and wherein the second nasal interface component is configured for substantially sealingly engaging or interfacing with the user's second nare.

2. The patient interface as claimed in claim 1, wherein said patient interface comprises a partition between the first nasal interfacing component and the second nasal interfacing component.

3. The patient interface as claimed in claim 2, wherein the partition provides for a mechanical fluid disconnection between a fluid flow path of the first nasal interfacing component and a fluid flow path of the second nasal interfacing component.

4. The patient interface as claimed in claim 2, wherein the partition provides for an adjustable or controllable mechanical fluid connection and/or disconnection between a fluid flow path of the first nasal interfacing component and a fluid flow path of the second nasal interfacing component.

5. The patient interface as claimed in claim 2, wherein the partition provides for an adjustment of a bias flow of the source of gases to said first and/or said second nasal interface components.

6. The patient interface as claimed in claim 2, wherein a diverter valve fluidly connects the source of gases to one of: the first conduit and the first nasal interface component, or the second conduit and the second nasal interface component to provide a flow of gases from the sources of gases to the sole inspiratory line; and/or wherein the diverter valve fluidly connects gases received from one of the first or second nasal interface components via the associated first or second conduit to provide the gases received to the sole expiratory line.

7. The patient interface as claimed in claim 1, wherein a diverter valve is operable to divert the source of gases to one of: the first conduit and the first nasal interface component or the second conduit and the second nasal interface component.

8. The patient interface as claimed in claim 1, wherein a diverter valve is operable to allow the alternation of the delivery of the source of gases to one of either the user's first nare or the user's second nare.

9. The patient interface as claimed in claim 1, wherein a diverter valve is operable to allow the delivery of the source of gases in a synchronised manner with a user's nasal cycle.

10. The patient interface as claimed in claim 1, wherein a diverter valve fluidly connects the sole expiratory line with a downstream device, or connects to a return port of the source of gases.

11. The patient interface as claimed in claim 1, wherein a pressure sensor is coupled to the sole expiratory line to provide a signal or indicator of a pressure provided to a user or a user's airway or of the gases in the sole expiratory line.

12. The patient interface as claimed in claim 1, wherein a single pressure sensor is provided for sampling a pressure in one or more of: the sole inspiratory line or the sole expiratory line or from a bias flow substantially at a bridge portion of said interface, said sampled pressure providing for an approximation of a patient airway pressure.

13. The patient interface as claimed in claim 1, wherein a difference in pressure between gases in the sole inspiratory line and gases in the sole expiratory line, or a measure of average pressure across the user's first of second nares, is determined/measured.

14. The patient interface as claimed in claim 1, wherein said patient interface comprises a retention system for retaining said interface upon a user's face.

15. The patient interface as claimed in claim 14, wherein said retention system is an associated two-part releasable connection arrangement, such that said interface can be positioned upon the user's face and removed and re-positioned as needed.

16. The patient interface as claimed in claim 15, wherein a first part of the two-part releasable connection arrangement is a dermal patch to be located upon the user's face, and a second part of the two-part releasable connection arrangement is an interface patch to be located on a user-facing side of the patient interface.

17. The patient interface as claimed in claim 1, wherein a body of said interface comprises at least one element responsive to force(s) or movement(s), or both, experienced by at least a first region of the patient interface.

18. The patient interface as claimed in claim 14, wherein the retention system is a headgear, the headgear being size adjustable for a user's head.

19. The patient interface as claimed in claim 1, wherein one or more medicaments is/are deliverable to the sole inspiratory line or to the first nasal interfacing component or the second nasal interfacing component when provided as part of the sole inspiratory line.

20. The patient interface as claimed in claim 19, wherein said one or more medicaments is/are atomized or nebulized for delivery into a flow of gases in the sole inspiratory line or into a gases flow path of the first nasal interfacing component or the second nasal interfacing component when operable as part of the sole inspiratory line.

* * * * *